(12) United States Patent
Lee

(10) Patent No.: US 11,045,585 B2
(45) Date of Patent: Jun. 29, 2021

(54) SPATIOTEMPORAL DELIVERY SYSTEM EMBEDDED IN 3D-PRINTING

(71) Applicant: The Trustees of Columbia University in the City of New York, New York, NY (US)

(72) Inventor: Chang Hun Lee, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 136 days.

(21) Appl. No.: 15/564,101

(22) PCT Filed: Apr. 7, 2016

(86) PCT No.: PCT/US2016/026419
§ 371 (c)(1),
(2) Date: Oct. 3, 2017

(87) PCT Pub. No.: WO2016/164566
PCT Pub. Date: Oct. 13, 2016

(65) Prior Publication Data
US 2018/0085493 A1    Mar. 29, 2018

Related U.S. Application Data

(60) Provisional application No. 62/303,843, filed on Mar. 4, 2016, provisional application No. 62/174,232, filed on Jun. 11, 2015, provisional application No. 62/148,074, filed on Apr. 15, 2015, provisional application No. 62/144,890, filed on Apr. 8, 2015.

(51) Int. Cl.
| | | |
|---|---|---|
| *A61L 27/44* | (2006.01) | |
| *A61L 27/18* | (2006.01) | |
| *A61L 27/54* | (2006.01) | |
| *A61L 27/56* | (2006.01) | |
| *A61L 27/50* | (2006.01) | |
| *D01D 5/00* | (2006.01) | |
| *B33Y 10/00* | (2015.01) | |
| *B33Y 70/00* | (2020.01) | |
| *B33Y 80/00* | (2015.01) | |
| *B29C 64/112* | (2017.01) | |
| *A61L 27/36* | (2006.01) | |
| *A61L 27/38* | (2006.01) | |
| *B29K 67/00* | (2006.01) | |
| *B29L 31/00* | (2006.01) | |

(52) U.S. Cl.
CPC .............. *A61L 27/44* (2013.01); *A61L 27/18* (2013.01); *A61L 27/3608* (2013.01); *A61L 27/3834* (2013.01); *A61L 27/3847* (2013.01); *A61L 27/50* (2013.01); *A61L 27/54* (2013.01); *A61L 27/56* (2013.01); *B29C 64/112* (2017.08); *B33Y 10/00* (2014.12); *B33Y 70/00* (2014.12); *B33Y 80/00* (2014.12); *D01D 5/0007* (2013.01); *A61L 2300/414* (2013.01); *A61L 2300/602* (2013.01); *A61L 2300/622* (2013.01); *A61L 2430/02* (2013.01); *A61L 2430/06* (2013.01); *A61L 2430/10* (2013.01); *A61L 2430/38* (2013.01); *B29K 2067/04* (2013.01); *B29K 2995/006* (2013.01); *B29K 2995/0056* (2013.01); *B29L 2031/7532* (2013.01)

(58) Field of Classification Search
CPC ................ A61K 47/00; A61K 47/6921; A61K 47/6927; B29C 64/00; D01D 5/0007
See application file for complete search history.

(56) References Cited

U.S. PATENT DOCUMENTS

| | | | |
|---|---|---|---|
| 6,730,252 B1 | 5/2004 | Teoh et al. | |
| 8,093,027 B2 | 1/2012 | Turos et al. | |
| 8,293,531 B1 | 10/2012 | Burg et al. | |
| 2004/0267362 A1* | 12/2004 | Hwang | A61F 2/08 623/13.15 |
| 2005/0161857 A1* | 7/2005 | Coombes | A61K 9/70 264/172.15 |
| 2007/0232169 A1* | 10/2007 | Strickler | A61L 15/225 442/181 |
| 2011/0009949 A1* | 1/2011 | Stankus | A61L 31/14 623/1.15 |
| 2011/0202142 A1 | 8/2011 | Mao et al. | |
| 2012/0093717 A1* | 4/2012 | Mauck | A61L 27/38 424/1.11 |
| 2013/0280318 A1 | 10/2013 | Lu et al. | |
| 2014/0079739 A1 | 3/2014 | Mao et al. | |
| 2015/0037385 A1 | 2/2015 | Shah et al. | |

FOREIGN PATENT DOCUMENTS

| | | |
|---|---|---|
| WO | WO2005/025493 | 3/2005 |
| WO | WO2014/144488 | 9/2014 |
| WO | WO2015/002707 | 1/2015 |

OTHER PUBLICATIONS

Ahtiainen et al., Autologous adipose stem cells and polylactide discs in the replacement of the rabbit temporomandibular joint disc, Journal of the Royal Society, Interface/The Royal Society, 2013, vol. 10, 9 Pages.

(Continued)

*Primary Examiner* — Kyle A Purdy
(74) *Attorney, Agent, or Firm* — Wolter Van Dyke Davis, PLLC; Timothy H. Van Dyke

(57) ABSTRACT

Provided herein is a 3D printing system and related compositions, and method of using such, that can produce a polymeric microfiber having embedded microspheres encapsulating an active agent with micron precision and high spatial and temporal resolution. One aspect of the present disclosure provides a method of forming a biocompatible scaffold. Another aspect provides a method of forming a polymeric fiber having a microencapsulated agent distributed in the polymeric fiber. Another aspect provides a composition including a polymeric microfiber produced by 3D printing.

3 Claims, 33 Drawing Sheets

(56) References Cited

OTHER PUBLICATIONS

Akkineni et al., 3D plotting of growth factor loaded calcium phosphate cement scaffolds, Acta Biomaterialia, 2015, vol. 27, pp. 264-274.

Allen et al., Tissue Engineering of the TMJ disc: a review, Tissue Engineering, 2006, vol. 12, No. 5, pp. 1183-1196.

Allen et al., Viscoelastic characterization of the prince temporomandibular joint disc under unconfined compression, Journal of Biomechanics, 2006, vol. 39, No. 2, pp. 312-322.

Alpaslan et al., Long-term evaluation of recombinant human bone morphogenetic protein-2 induced bone formation with a biologic and synthetic delivery system, British Journal of Oral Maxillofacial Surgery, 1996, vol. 34, No. 5, pp. 414-418.

Bax et al., Bone morphogenetic Protein-2 Increases the rate of callus formation after fracture of the rabbit tibia, Calcified Tissue International, 1999, vol. 65, No. 1, pp. 83-89.

Bose et al., A. Bone tissue engineering using 3D printing, Materials Today, 2013, vol. 16, pp. 496-502.

Brown et al., Inductive, scaffold-based, regenerative medicine approach to reconstruction of the temporomandibular joint disk, Journal of Oral and Maxillofacial Surgery: Official Journal of the American Association of Oral and Maxillofacial Surgeons, 2012, vol. 70, No. 11, pp. 2656-2668.

Castro et al., Integrating biologically inspired nanomaterials and table top stereolithography for 3D printed biomimetic osteochondral scaffolds, Nanoscale, 2015; vol. 7, No. 33, pp. 14010-14022.

Detamore et al., Cell type and distribution in the porcine temporomandibular joint disc, Journal of Oral and Maxillofacial Surgery: Official Journal of the American Association or Oral and Maxillofacial Surgeons, 2006, vol. 64, No. 2, pp. 243-248.

Dimitroulis, A critical review of interpositional grafts following temporomandibular joint discectomy with an overview of the dermis-fat graft, International Journal of Oral and Maxillofacial Surgery, 2011, vol. 40, No. 6, pp. 561-568.

Elhai et al., Conjugal transfer of DNA to cyanobacteria, Methods in Enzymology, 1988, vol. 167, pp. 747-754.

Embree et al., Soft tissue ossification and condylar cartilage degeneration following TMJ disc perforation in a rabbit pilot study, Osteoarthritis and Cartilage/OARS, Osteoarthritis Research Society, 2015, vol. 23, No. 4, pp. 629-639.

Estabrooks et al., A retrospective evaluation of 301 TMJ Proplast-Teflon implants, Oral Surgery, Oral Medicine, and Oral Pathology, 1990, vol. 70, No. 3, pp. 381-386.

Hagandora et al., TMJ disc removal: comparison between preclinical studies and clinical findings, Journal of Dental Research, 2012, vol. 91, No. 8, pp. 745-752.

Hagandora et al., Poly (glycerol sebacate): a novel scaffold material for temporomandibular joint disc engineering, Tissue Engineering Part A, 2013, vol. 19, No. 5-6, pp. 729-737.

Henry et al., Treatment outcomes for temporomandibular joint reconstruction after Proplast-Teflon implant failure, Journal of Oral and Maxillofacial Surgery : Official Journal of the American Association of Oral and Maxillofacial Surgeons, 1993, vol. 51, pp. 352-358.

International Search Report and Written Opinion dated Jul. 8, 2016 in related Application No. PCT/US2016/026419 filed Apr. 7, 2016, 14 pages.

Isobe et al., Bone regeneration produced in rat femur defects by polymer capsules containing recombinant human bone morphogenetic protein-2, Journal of Oral Maxillofacacial Surgery, 1999, vol. 57, No. 6, pp. 695-698.

Jeong, 3D Printing and Biofabrication for Load Bearing Tissue Engineering, Advances in Experimental Medicine and Biology, 2015, vol. 881, pp. 3-14.

Jin et al., Platelet-derived growth factor delivery via nanofibrous scaffolds for soft-tissue repair, Advanced Skin Wound Care, 2010, vol. 1, pp. 375-381.

Kalpakci et al., An interspecies comparison of the temporomandibular joint disc, Journal of Dental Research, 2011, vol. 90, pp. 193-198.

Kamath et al., Polycaprolactone scaffold engineered for sustained release of resveratrol: therapeutic enhancement in bone tissue engineering Scaffolds with microspheres, Int. J. Nanomed., 2014, vol. 9, No. 1, pp. 183-195.

Kuboki et al., Two Distinctive BMP-carriers induce zonal chrondrogenesis and membranous ossification, respectively; geometrical factors of matrices for cell-differentiation, Connective Tissue Research, 1995, vol. 32, Nos. 1-4, pp. 219-226.

Lai et al., Histological analysis of regeneration of temporomandibular joint discs in rabbits by using a reconstituted collagen template, International Journal of Oral and Maxillofacial Surgery, 2005, vol. 34, No. 3, pp. 311-320.

Lam et al., Dynamics of in vitro polymer degradation of polycaprolactone-based scaffolds: accelerated versus simulated physiological conditions, Biomedical Materials, 2008, vol. 3, 15 Pages.

Lee et al., Tissue formation and vascularization in anatomically shaped human joint condyle ectopically in vivo, Tissue Engineering Part A, 2009, vol. 15, pp. 3923-3930.

Lee et al., Regeneration of the articular surface of the rabbit synovial joint by cell homing: a proof of concept study, Lancet, 2010, vol. 376, No. 9739, pp. 440-448.

Lee et al., CTGF directs fibroblast differentiation from human mesenchymal stem/stromal cells and defines connective tissue healing in a rodent injury model, The Journal of Clinical Investigation, 2010, vol. 120, No. 9, pp. 3340-3349.

Lee et al, Three-dimensional printed multiphase scaffolds for regeneration of periodontium complex. Tissue engineering Part A, 2014, vol. 20, pp. 1342-1351.

Lee et al., Protein-releasing polymeric scaffolds induce fibrochondrocytic differentiation of endogenous cells for knee meniscus regeneration in sheep, Science Translational Medicine, 2014, vol. 6, No. 266, p. 266ra171.

Li et al., Nanofiber scaffolds with gradations in mineral content for mimicking the tendon-to-bone insertion site, Nano Lett, 2009, vol. 9, No. 7, pp. 2763-2768.

Li et al., 3D-Printed Biopolymers for Tissue Engineering Application, International Journal of Polymer Science, 2014, 13 Pages.

Lu et al., Functional attachment of soft tissues to bone: development, healing, and tissue engineering, Annual Review of Biomedical Engineering, 2013, vol. 15, pp. 201-226.

Lumpkins et al., Regional variations in the viscoelastic compressive properties of the temporomandibular joint disc and implications toward tissue engineering; Journal of Biomedical Materials Research Part A, 2008, vol. 90, No. 3, pp. 784-791.

Macbarb et al., Engineering functional anisotropy in fibrocartilage neotissues, Biomaterials, 2013, vol. 34, No. 38, pp. 9980-9989.

Moioli et al., Sustained release of TGFbeta3 from PLGA microspheres and its effect on early osteogenic differentiation of human mesenchymal stem cells, Tissue Engineering, 2006, vol. 12, No. 3, pp. 537-546.

Murata et al., Carrier-dependency of cellular differentiation induced by bone morphogenetic protein in ectopic sites, International Journal of Oral Maxillofacial Surgery, 1998, vol. 27, No. 5, pp. 391-396.

Pan et al., Poly (lactide-co-glycolid) porous scaffolds for tissue engineering and regenerative medicine, Interface Focus, 2012, vol. 2, No. 3, pp. 366-377.

Poldervaart et al., Sustained release of BMP-2 in bioprinted alginate for osteogenicity in mice and rats, PloS One, 2013, vol. 8, No. 8, p. e72610. 9 Pages.

Qian et al., Fabrication and characterization of controlled release poly(D,L-lactide-co-glycolide) millirods, Journal of Biomedical Materials Research, 2001, vol. 55, pp. 512-522.

Richardson et al., Polymeric system for dual growth factor delivery, Nat Biotech, 2001, vol. 19, pp. 1029-1034.

Saito et al., New synthetic biodegradable polymers as BMP carriers for bone tissue engineering, Biomaterials, 2003, vol. 24, No. 13, pp. 2287-2293.

Santos et al., Si—Ca—P xerogels and bone morphogenetic protein act synergistically on rat stromal marrow cell differentiation in vitro, Journal of Biomedical Materials Research, 1998, vol. 41, No. 1, pp. 87-94.

(56) References Cited

OTHER PUBLICATIONS

Scapino et al., The behaviour of collagen fibres in stress relaxation and stress distribution in the jaw-joint disc of rabbits, Archives of Oral Biology, 1996, vol. 41, No. 11, pp. 1039-1052.

Shim et al., Three-dimensional printing of rhBMP-2-loaded scaffolds with long-term delivery for enhanced bone regeneration in a rabbit diaphyseal defect, Tissue Engineering Part A, 2014, vol. 20, Nos. 13 and 14, pp. 1980-1992.

Shim et al., Efficacy of rhBMP-2 loaded PCL/PLGA/beta-TCP guided bone regeneration membrane fabricated by 3D printing technology for reconstruction of calvaria defects in rabbit, Biomedical Materials, 2014, vol. 9, No. 6, p. 065006.

Shin et al., Rotator cuff regeneration using a bioabsorbable material with bone marrow-derived mesenchymal stem cells in a rabbit model, The American Journal of Sports Medicine, 2012, vol. 40, No. 6, pp. 1259-1268.

Singh et al., Microsphere-based scaffolds for cartilage tissue engineering: using subcritical CO(2) as a sintering agent, Acta Biomater, 2010, vol. 6, No. 1, pp. 137-143.

Stankovic et al., Morphological and biomechanical features of the temporomandibular joint disc: an overview of recent findings, Archives of Oral Biology, 2013, vol. 58, No. 10, pp. 1475-1482.

Studier, Protein production by auto-induction in high-density shaking cultures, Protein Expression and Purification, 2005, vol. 41, No. 1, pp. 207-234.

Sweeney et al., Repair of critical size rat calvarial defects using extracellular matric protein gels, Journal of Neurosurgery, 1995, vol. 83, No. 4, pp. 710-715.

Tanaka et al., Biomechanical behavior of the temporomandibular joint disc, Critical Reviews in Oral Biology and Medicine : An Official Publication of the American Association of Oral Biologists, 2003, vol. 14, pp. 138-150.

Tarafder et al., Spatiotemporal Delivery of Multiple Growth Factors in 3D Printed Scaffolds for Engineering Integrated Soft Tissue-To-Bone Interfaces From Stem/Progenitor Cells, Orthopaedic Research Society 2016 Annual Meeting Paper No. 0065 (1 page).

Varde et al., Microspheres for controlled release drug delivery, Expert Opinion Biological Therapy, 2004, vol. 4, No. 1, pp. 35-51.

Viljanen et al., Low dosage of native allogeneic bone morphogenetic protein in repair of sheet calvarial defects, International Journal of Oral Maxillofacial Surgery, 1997, vol. 26, No. 5, pp. 389-393.

Willard et al., The regional contribution of glycosaminoglycans to temporomandibular joint disc compressive properties, Journal of Biomechanical Engineering, 2012, vol. 134, p. 011011-1-011011-8.

Yilgor et al., Sequential BMP-2/BMP-7 delivery from polyester nanocapsules, Journal of Biomedical Materials Research Part A, Jul. 2009, vol. 93, pp. 528-536.

* cited by examiner

FIG. 1C–FIG. 1E
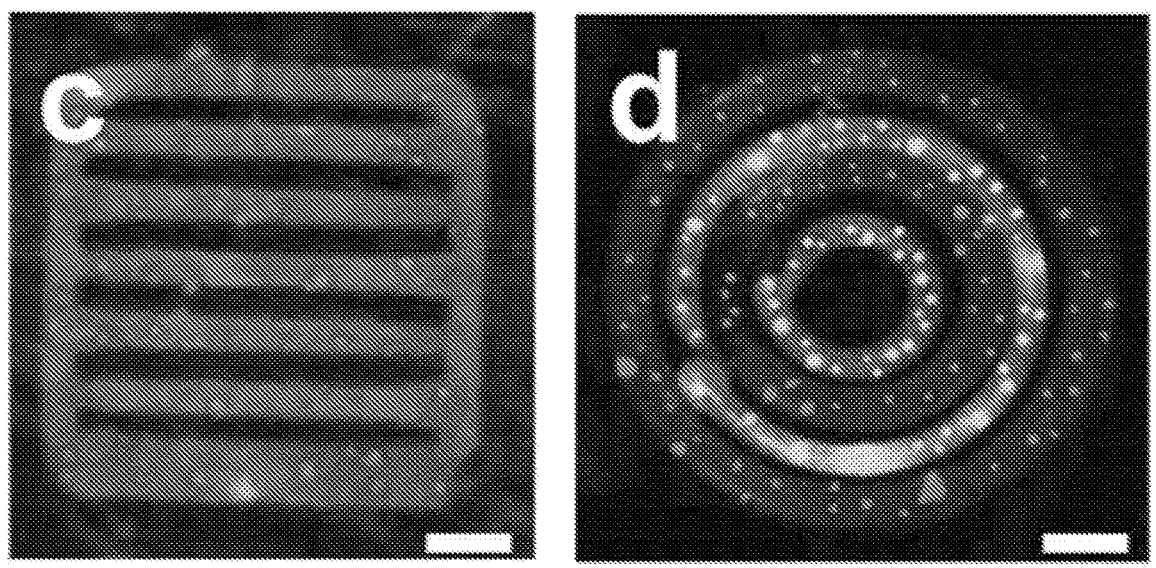
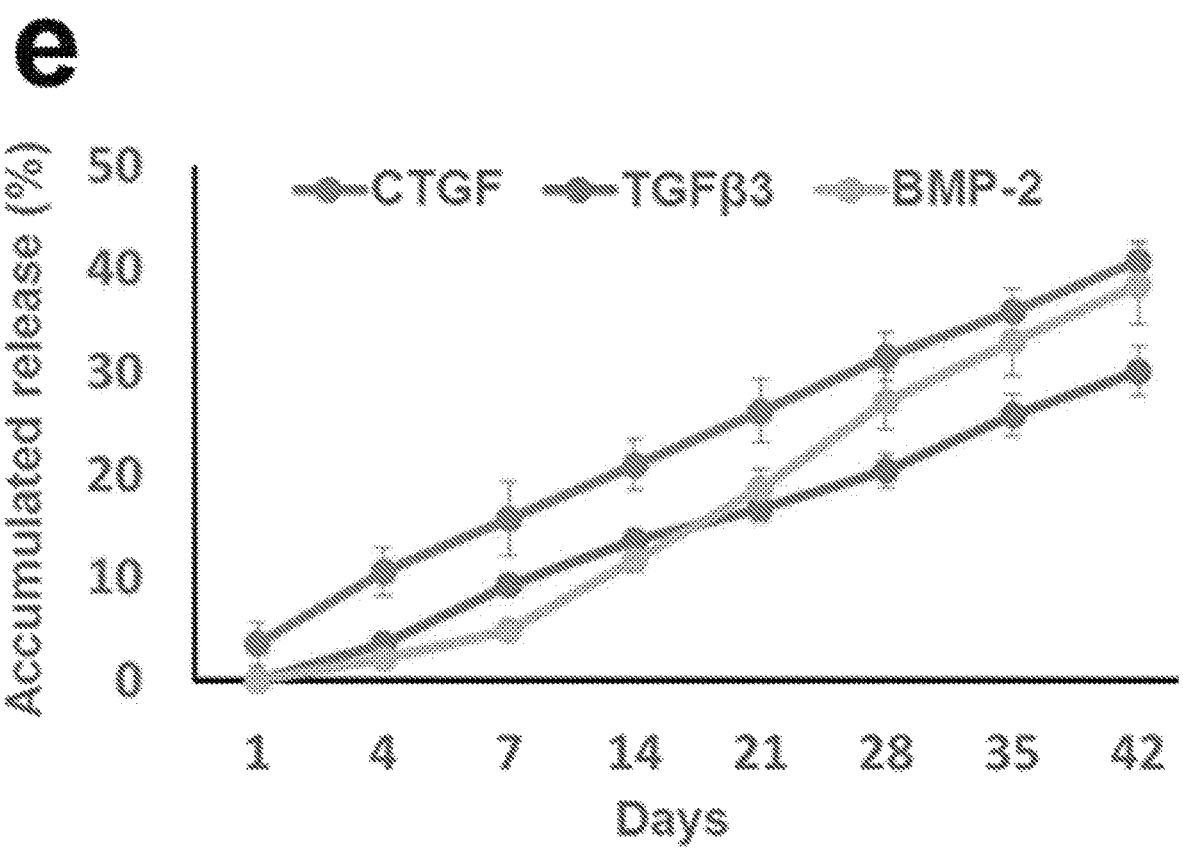

FIG. 4A
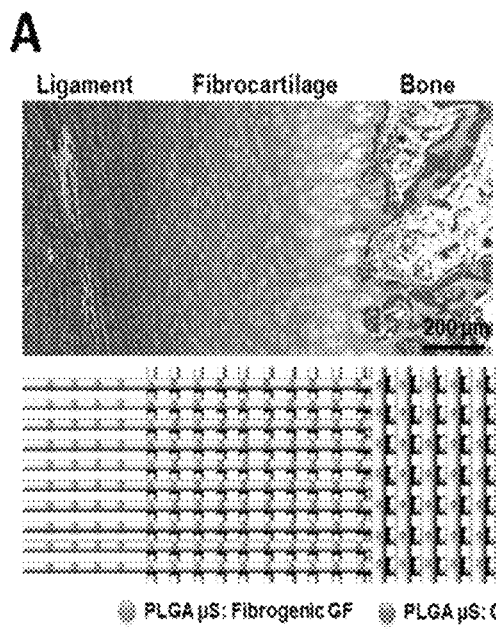
FIG. 4B
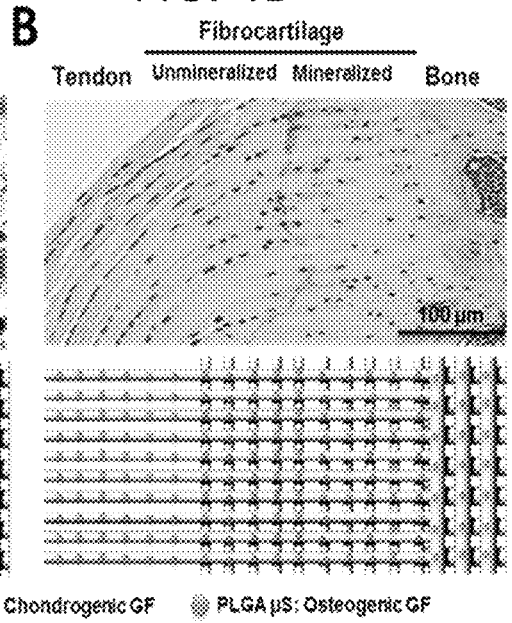
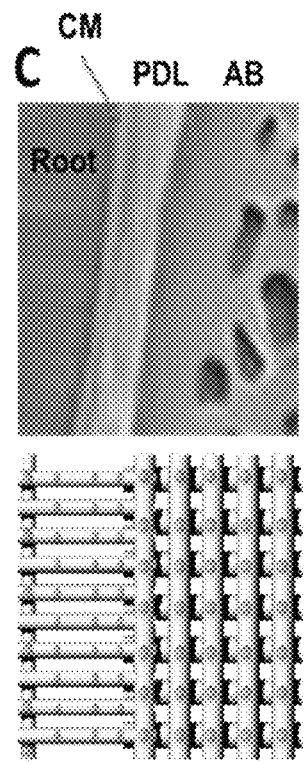
FIG. 4C
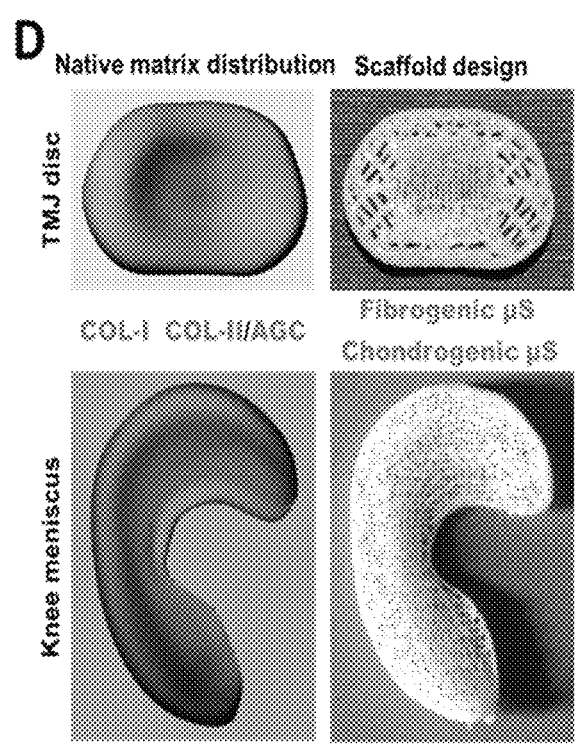
FIG. 4D

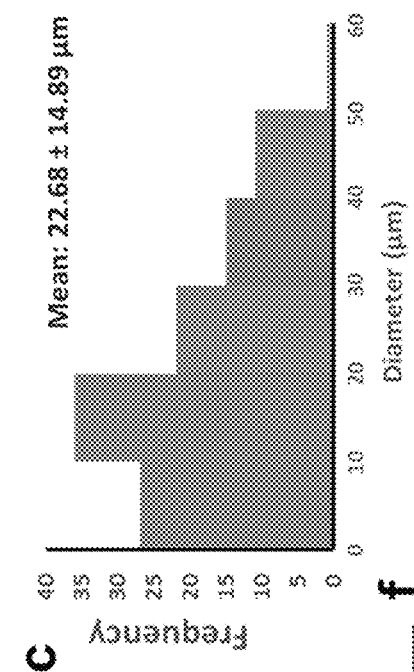
FIG. 7A
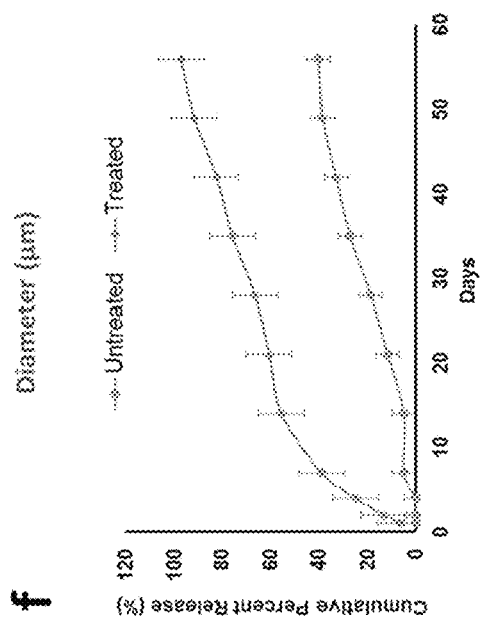
FIG. 7B
FIG. 7C
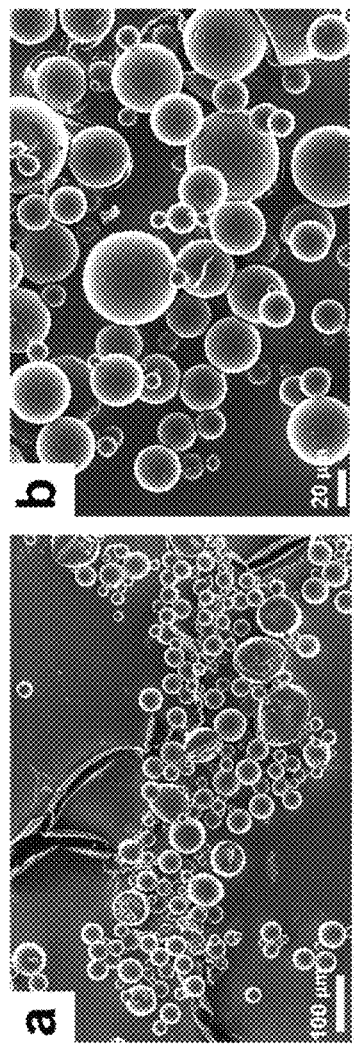
FIG. 7D
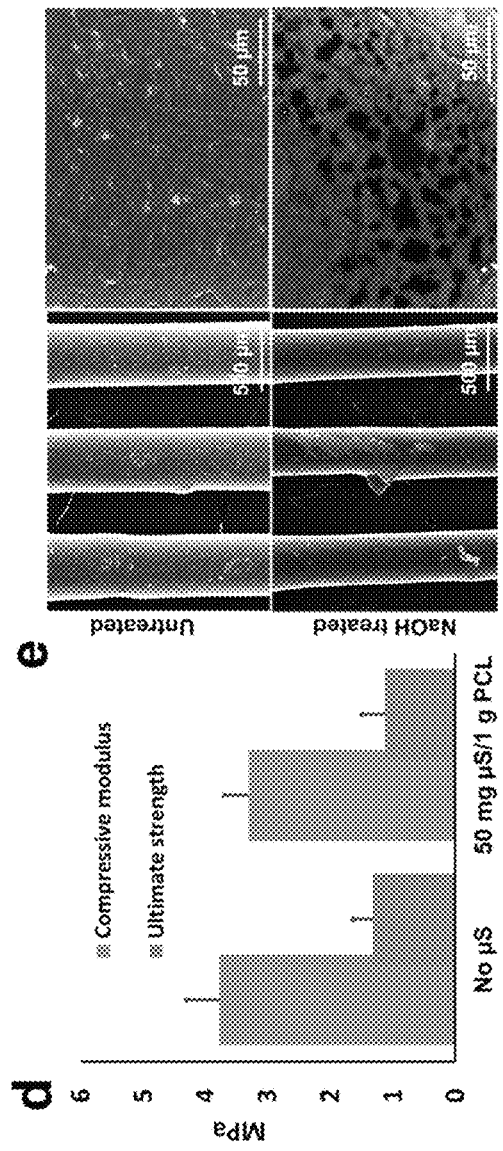
FIG. 7E
FIG. 7F

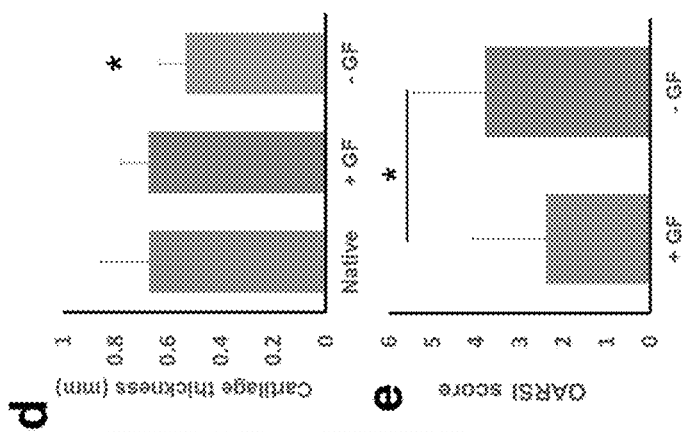
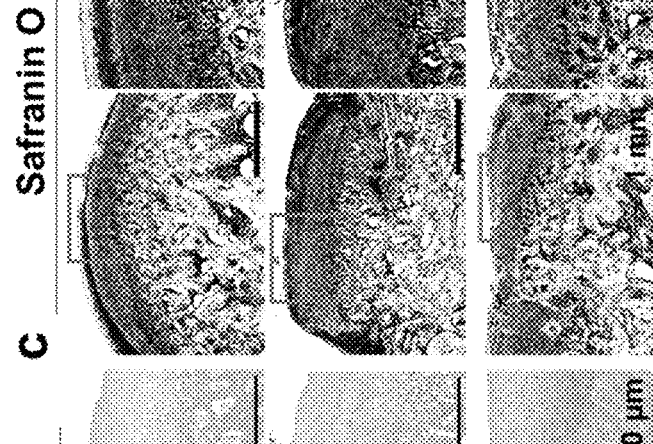
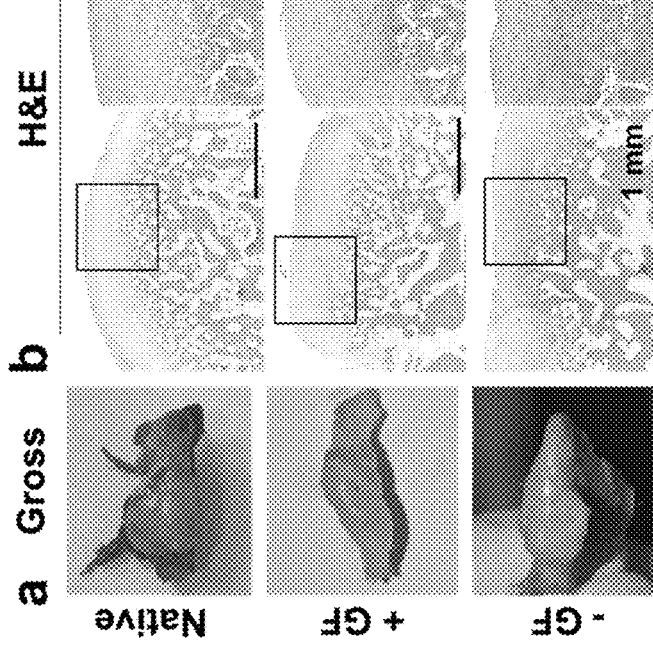
FIG. 12A  FIG. 12B  FIG. 12C  FIG. 12D  FIG. 12E

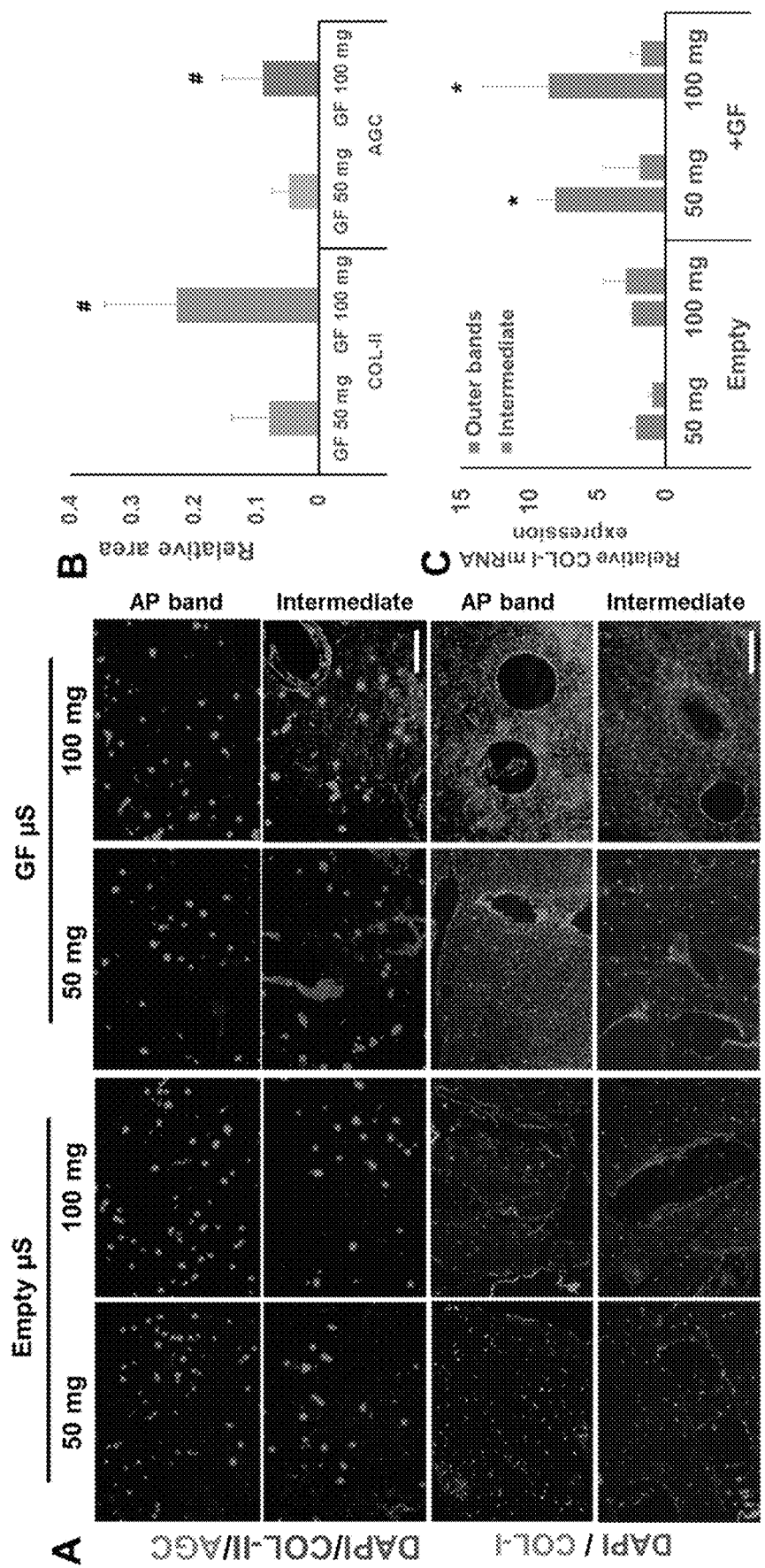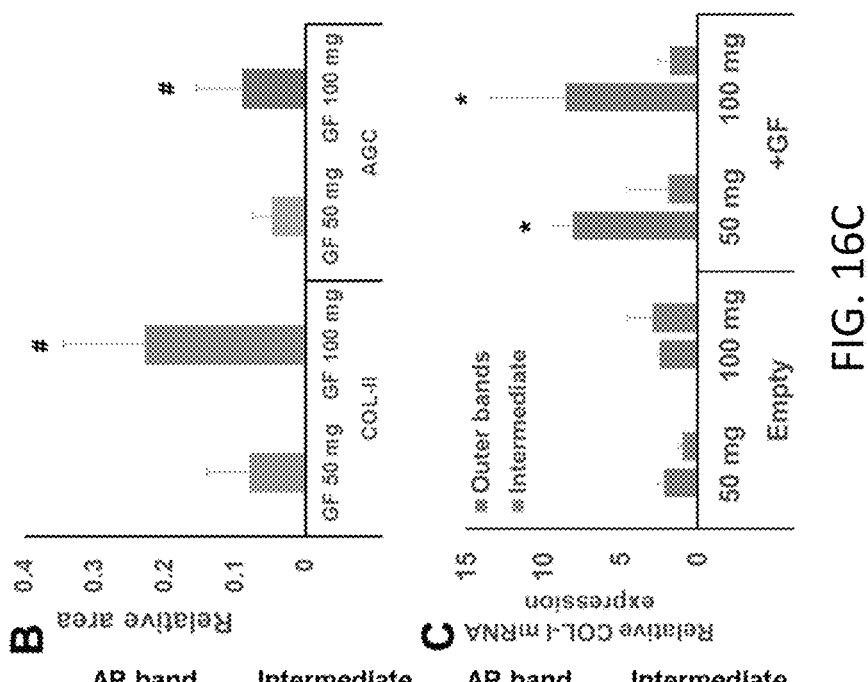

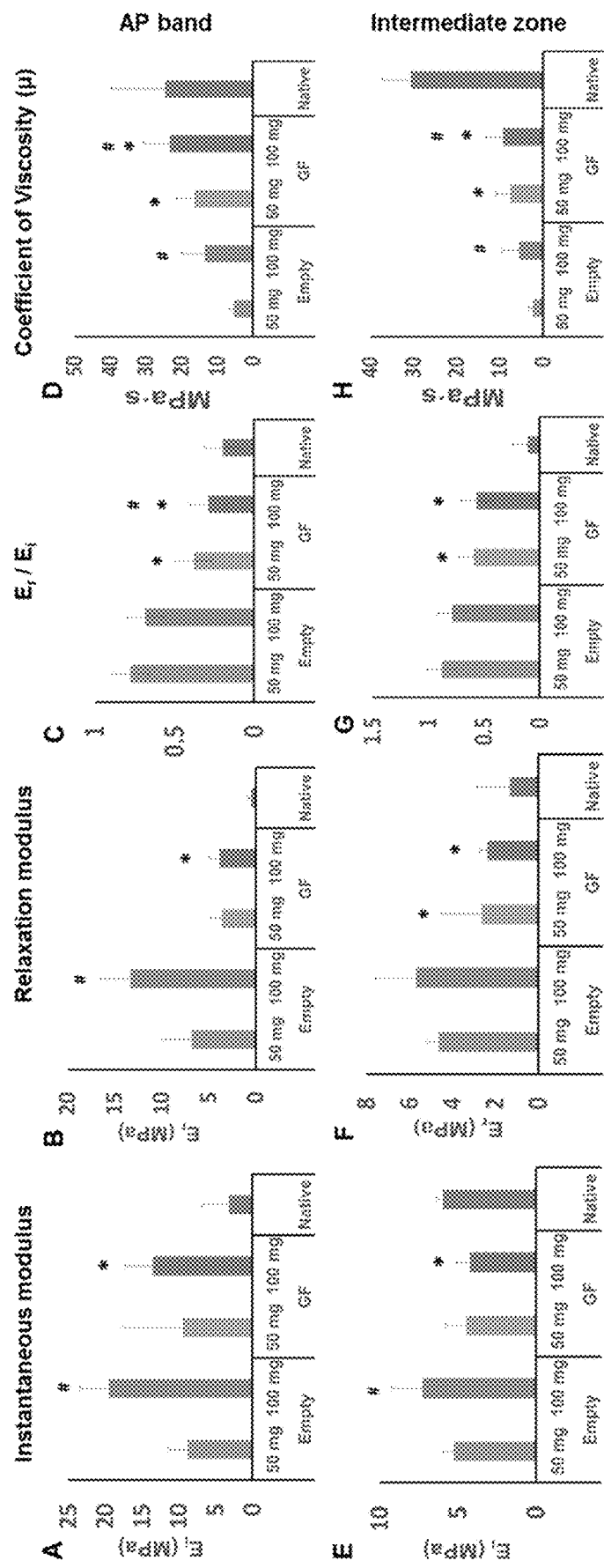

FIG. 20
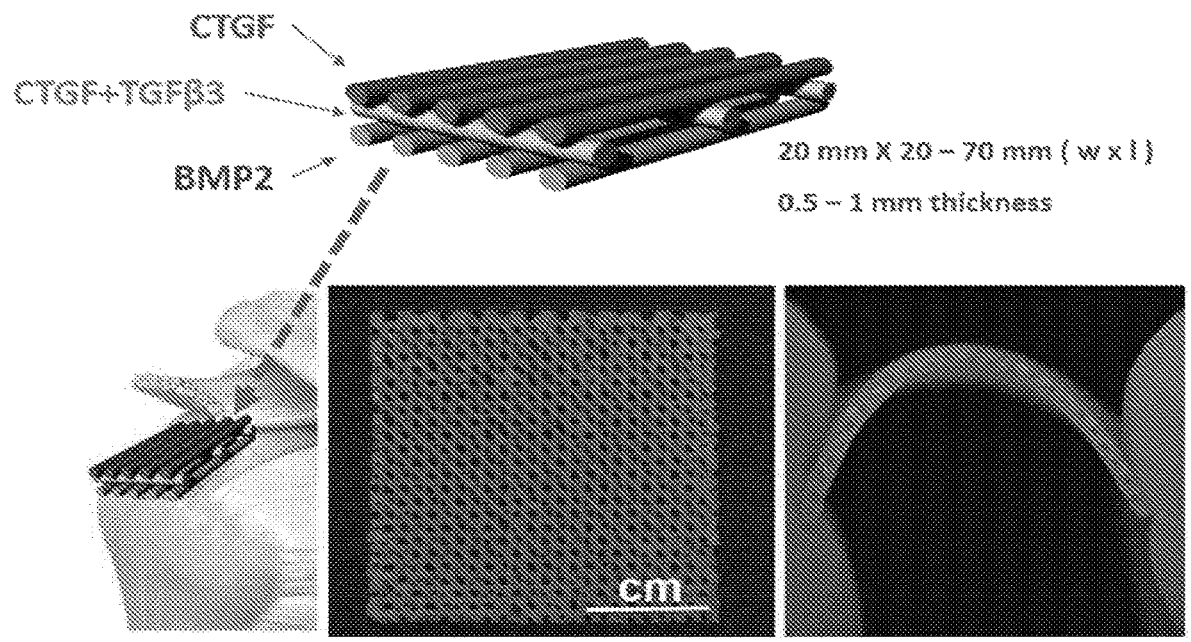
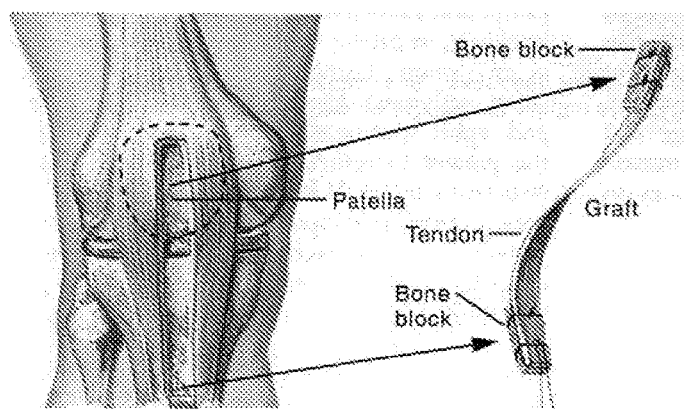
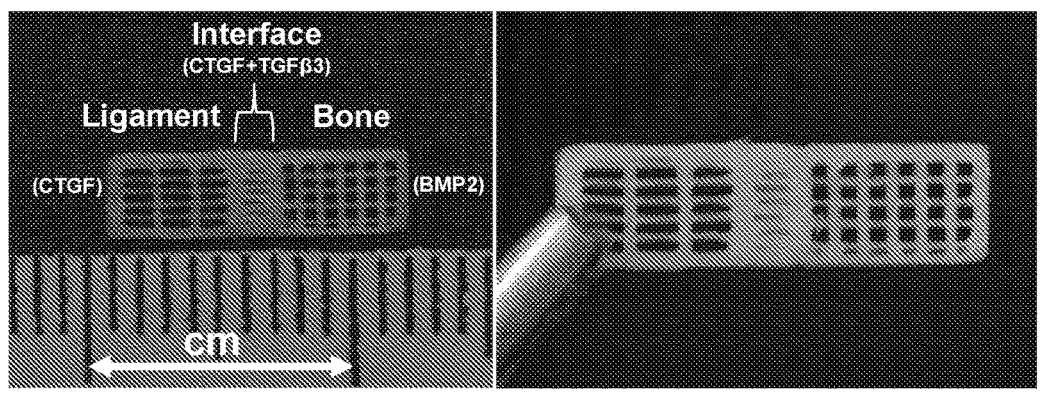

H&E

Trichrome

FIG. 25
Alizarin Red
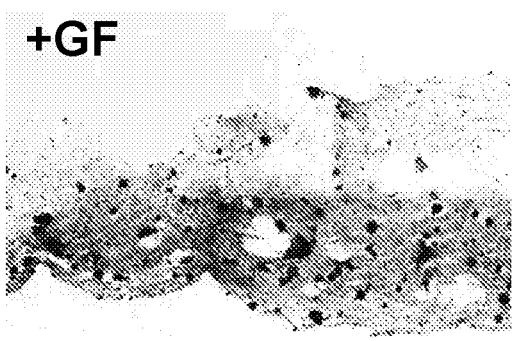
+GF
-GF

Native tendon-bone interface

Smith et al., Connective Tissue Research, 53(2): 95–105, (2012)

Col-I/Col-II/AGC/OC/DAPI

SPATIOTEMPORAL DELIVERY SYSTEM EMBEDDED IN 3D-PRINTING

CROSS-REFERENCE TO RELATED APPLICATIONS

The present application claims the benefit of priority to PCT International Application No. PCT/US16/26419 filed 7 Apr. 2016, which claims the benefit of U.S. Provisional Application Ser. No. 62/303,843 filed 4 Mar. 2016; U.S. Provisional Application Ser. No. 62/174,232 filed 11 Jun. 2015; U.S. Provisional Application Ser. No. 62/148,074 filed 15 Apr. 2015; and U.S. Provisional Application Ser. No. 62/144,890 filed 8 Apr. 2015; each of which are incorporated herein by reference in their entireties.

STATEMENT REGARDING FEDERALLY SPONSORED RESEARCH OR DEVELOPMENT

This invention was made with government support under grant DE023583 awarded by the National Institutes of Health. The government has certain rights in the invention.

MATERIAL INCORPORATED-BY-REFERENCE

Not Applicable.

BACKGROUND OF THE INVENTION

Tissue engineering provides for medical applications, biosensors, experimental drug testing, or other non-therapeutic applications. Biocompatible scaffolds are generally necessary to support growth for tissue generation to occur. While conventional scaffolds can include transplanted cells from a subject (which can reduce immunologic complications), commercialization of these cell-seeded scaffolds can be problematic with respect to ex vivo cell culture, packing and shipping, contamination, or pathogen transmission. Biomaterials that are made without cell transplantation may overcome these commercialization issues, but presently the design and engineering of conventional scaffolds may not perform as well.

Various methods for conventional 3D printed scaffolds in tissue engineering and regenerative medicine can be found in, for example, Jeong 2015; Lee 2010a; Lee 2014a; Lee 2009; and Lee 2014b. As another example, 3D printing processes can include selective laser sintering (SLS), stereolithography (SLA), fused deposition modeling (FDM) and bioplotting (see e.g., Bose 2013). As another example, methods for 3D printing scaffolds with highly porous and interconnected micro-architecture and reconstructing anatomical shape and dimension can be found in, for example, Lee 2010a; Lee 2014a; Lee 2009; and Lee 2014b; and Bose 2013. Methods for 3D printed scaffolds further incorporating delivery of agents, growth factors, or other bioactive cues to improve tissue regeneration can be found in, for example, Lee 2010a; Akkineni 2015; Moioli 2006; Poldervaart 2013; and Shim 2014a. For example, a composite of polycaprolactone (PCL), poly(lactic-co-glycolic acid) (PLGA) and β tricalcium phosphate (β-TCP) can be constructed into a membrane by 3D printing, and bone morphogenetic protein 2 (BMP-2) can be loaded in collagen gel and delivered into the membrane's pores according to Shim 2014b. As another example, BMP-2 adsorbed PCL/PLGA/β-TCP membrane can be implanted in rabbit calvaria defects and result in improved bone healing according to Shim 2014b. Similarly, hollow cylindrical PCL/PLGA scaffolds can be fabricated by 3D printing and BMP-2 can be delivered into the hollow space via collagen or gelatin for healing of bone segmental defect according to Shim 2014b. As another example, SLA can be utilized to construct nanocomposite osteochondral scaffolds consisting of a subchondral bone layer with nanocrystalline hydroxyapatite (nHA) and a cartilage layer with transforming growth factor β1 (TGFβ1) encapsulated in PLGA microspheres (μS) according to Castro 2015. As another example, gelatin microparticles encapsulated with BMP-2 can be blended with alginate, followed by bioprinting into a 3D porous scaffold that in turn promotes osteogenic differentiation of MSCs according to Poldervaart 2013. As another example, bioplotted, anatomically correct PCL-HA scaffolds with TGFβ3-collagen delivery into cartilage portion can replace entire synovial joint condyles in rabbits, followed by functional regeneration according to Lee 2010a. As another example, PLGA μS encapsulated with a growth factor or various growth factors can be incorporated on the surface of 3D printed PCL microstrands in different regions by applying μS-suspended ethanol through the scaffold's microchannels. Various types of cells, biomaterial scaffolds, and/or biochemical/physical stimulations can be utilized to replace or regenerate TMJ discs as in Ahtiainen 2013; Allen 2006a; Brown 2012; Hagandora 2013; Lai 2005; and MacBarb 2013. Biological material alone without cells, including reconstituted type I collagen templates and porcine ECM-derived scaffold can partially replace TMJ disc in animal models but only resulted in modest improvement (Brown 2012; Lai 2005). Polylactide (PLA) scaffold seeded with adipose derived stem/progenitor cells (ADSCs) supported rabbit TMJ disc healing thus preventing condylar degeneration (Ahtiainen 2013). Anisotropic disc-shaped fibrocartilage in a biconcave hydrogel with fibrochondrocytes and chondrocytes can be engineered, stimulated by chondroitinase-ABC and TGFβ1 and axial compression (MacBarb 2013). But, despite the formation of anisotropic collagen alignment, it achieved neither the mechanical properties nor heterogeneous cartilaginous matrix similar to those of native tissues (MacBarb 2013).

SUMMARY OF THE INVENTION

Among the various aspects of the present disclosure is the provision of a 3D-Printing delivery system and related compositions, and method of using such, with micron precision and high spatial and temporal resolution.

One aspect of the present disclosure provides a method of forming a biocompatible scaffold.

One embodiment provides a method of forming a biocompatible scaffold. In some embodiments, the method includes encapsulating at least one agent in a plurality of microspheres; combining the plurality of microspheres and a matrix material, the matrix material being suitable for forming a scaffold via 3D printing; introducing the combination of microspheres and matrix material into a first cartridge of a 3D printing device; heating the combination of microspheres and matrix material in the first cartridge sufficiently to allow dispensing of the combination while preventing substantial degradation of the microsphere or the at least one agent encapsulated in the microsphere; dispensing the heated combination of microspheres and matrix material from the first cartridge through a printing needle to form a polymeric microfiber, wherein the microspheres are distributed through the polymeric microfiber; or forming a scaffold comprising a plurality of the polymeric microfibers, wherein the microspheres are distributed through the scaffold by way of the polymeric microfibers.

Method features discussed above can be combined with other features discussed below.

Another aspect provides a method of forming a polymeric fiber having a microencapsulated agent distributed in the polymeric fiber.

One embodiment provides a method of forming a polymeric fiber having a microencapsulated agent distributed in the polymeric fiber including encapsulating at least one agent in a plurality of microspheres; combining the plurality of microspheres and a matrix material, the matrix material being suitable for forming a scaffold via 3D printing; introducing the combination of microspheres and matrix material into a first cartridge of a 3D printing device; heating the combination of microspheres and matrix material in the first cartridge sufficiently to allow dispensing of the combination of microspheres and matrix material while preventing substantial degradation of the microsphere or the agent encapsulated in the microsphere; or dispensing the heated combination of microspheres and matrix material from the cartridge through a printing needle to form a polymeric microfiber, wherein the microspheres are distributed through the polymeric microfiber.

Method features discussed above can be combined with other features discussed above and below.

Another aspect provides a composition including a polymeric microfiber produced by 3D printing.

One embodiment provides a composition including a polymeric microfiber produced by 3D printing or a plurality of microspheres encapsulating at least one agent; wherein the microsphere encapsulated agent is distributed through the polymeric microfiber.

Features related to the composition can be combined with other features discussed above with respect to above methods of forming a scaffold or polymeric fiber. Composition features discussed above can be combined with other features discussed below.

In some embodiments, the microspheres include at least a first group of microspheres and a second group of microspheres. For example, the first group of microspheres and the second group of microspheres can include at least one agent. As another example, the first group of microspheres and the second group of microspheres comprise at least one different agent. Features related to microspheres can be combined with other features discussed above and below In some embodiments, the method or composition includes introducing the combination of microspheres and matrix material into a second cartridge of a 3D printing device. In some embodiments, the method or composition includes heating the combination of microspheres and matrix material in the second cartridge sufficiently to allow dispensing of the combination of microspheres and matrix material while preventing substantial degradation of the microsphere or the agent encapsulated in the microsphere. In some embodiments, the method or composition includes interchanging the first cartridge and the second cartridge during a printing process. Features related to the combination of microspheres and matrix material can be combined with other features discussed above and below.

In some embodiments, the method or composition includes at least one agent, wherein the at least one agent includes a growth factor. Features related to the agents and growth factors can be combined with other features discussed above and below.

In some embodiments, the method or composition includes progenitor cells, such as stem cells, wherein the growth factor stimulates fibroblastic, chondrogenic, or osteogenic differentiation of the stem cells. Features related to progenitor cells can be combined with other features discussed above and below In some embodiments, the method or composition includes a first growth factor and a second growth factor alternately embedded in the microfibers. In some embodiments, the method or composition includes at least one agent, wherein the at least one agent includes a growth factor selected from the group consisting of CTGF, TGFβ, TGFβ3, CTGF, BMPs, SDF, bFGF, IGF, GDF, PDGF, VEGF, or EGF, or an isoform thereof. Features related to the growth factors can be combined with other features discussed above and below.

In some embodiments, the method or composition includes a matrix material and a polymeric microfiber, wherein the matrix material comprises polycaprolactone (PCL) and the polymeric microfiber comprises PCL. Features related to matrix material can be combined with other features discussed above and below.

In some embodiments, the method or composition includes heating the combination of microspheres and matrix material to less than the melting point of the microsphere. In some embodiments, the method or composition includes heating the combination of microspheres and matrix material to about 60° C., about 65° C., about 70° C., about 75° C., about 80° C., about 85° C., about 90° C., about 95° C., about 100° C., about 105° C., about 110° C., about 120° C., about 130° C., about 140° C., about 150° C., about 160° C., about 170° C., about 180° C., or about 190° C. Features related to heating can be combined with other features discussed above and below.

In some embodiments, the method or composition includes encapsulated growth factors, wherein the bioactivity of the encapsulated growth factors is substantially maintained. Features related to encapsulation can be combined with other features discussed above and below.

In some embodiments, the method or composition includes a printing needle, wherein the printing needle can have an inner diameter of about 20 μm to about 750 μm. For example, the printing needle can an inner diameter of about 50 μm to about 400 μm. Features related to the printing needle can be combined with other features discussed above and below.

In some embodiments, the method or composition includes a 3D printed scaffold including microstrands having a microstrand diameter of about 100 μm to about 400 μm. In some embodiments, the 3D printed scaffold comprises microstrands having an inter-microstrand spacing or microchannel width of about 100 μm to about 600 μm. Features related to the microstrand diameter can be combined with other features discussed above and below.

In some embodiments, the method or composition includes a growth factor encapsulated microsphere. In some embodiments, the growth factor encapsulated microsphere has a diameter of about 10 μm to about 600 μm. In some embodiments, the growth factor encapsulated microsphere is embedded at about 10 mg to about 100 mg μS per about 1 g of matrix material. In some embodiments, the growth factor encapsulated microsphere has sustained release of growth factor for at least 42 days. In some embodiments, the growth factor encapsulated microsphere is about 50 mg μS per 1 g matrix material. Features related to microspheres can be combined with other features discussed above and below.

In some embodiments, the method or composition includes treating the scaffold, composition, or polymeric fiber with NaOH to create micro-pores. Features related to NaOH treatment or micro-pores can be combined with other features discussed above and below.

In some embodiments, the method or composition includes the formation of a multi-tissue complex and the mechanical properties or composition of the resulting regenerated multi-tissue complex have substantially similar mechanical properties or composition of a corresponding native multi-tissue complex. Features related to multi-tissue complex or mechanical properties can be combined with other features discussed above and below.

In some embodiments, the method or composition further includes dispensing a plurality of heated matrix materials or a plurality of combinations heated matrix materials or microspheres from a plurality of cartridges, the contents of each cartridge independently selected. In some embodiments, each cartridge of the plurality of cartridges includes a printing needle or a heating element. In some embodiments, each cartridge of the plurality of cartridges shares a printing needle or a heating element. In some embodiments, a first portion of cartridges each includes a printing needle or a heating element and a second portion of cartridges shares a printing needle or a heating element.

In some embodiments, the plurality of cartridges includes one or more active cartridges dispensing matrix material, microspheres, or a combination thereof. In some embodiments, the one or more active cartridges can be switched among the plurality of cartridges before, during, or after dispensing the heated combination.

Features related to cartridges, plurality of cartridges, or switching of cartridges can be combined with other features discussed above and below.

In some embodiments, the heating temperature is about the melting temperature of the matrix material and the combination of the matrix material and microencapsulated active agent is heated such that 90%, 80%, 70%, 60%, 50%, 40%, 30%, 20%, or 10% of the total volume of microspheres do not reach more than 60° C. for more than about 10-40 minutes (e.g., about 30 minutes). In some embodiments, the combination of the matrix material and microencapsulated active agent is heated such that 80% of the total volume of microspheres do not reach more than 45° C. for more than about 30 minutes. In some embodiments, a first printing cartridge comprising the combination of the matrix material and microencapsulated active agent is switched for a second printing cartridge comprising the combination of the matrix material and microencapsulated active agent before 80% of the total volume of microspheres do reach more than 45° C. for more than about 30 minutes.

Features related to heating temperature, melting point, temperature threshold for percentage of total volume of microspheres, or heating can be combined with other features discussed above and below.

Another aspect provides for a method of treating a tissue defect with the composition or scaffold produced according to the features discussed above. In some embodiments, the method includes implanting the scaffold into a subject in need thereof. For example, the tissue defect can be associated with a multi-tissue interface selected from the group consisting of musculoskeletal system; craniofacial system; periodontium; cementum (CM)-periodontal ligament (PDL)-alveolar bone (AB) complex; ligament-to-bone insertion; tendon-to-bone insertion; rotator cuff; supraspinatus tendon-to-bone interface; interface between tendon, fibrocartilage, or bone; supraspinatus tendon-fibrocartilage-bone interface; articular cartilage-to-bone junction; anterior cruciate ligament (ACL)-to-bone complex; anterior cruciate ligament-fibrocartilage-bone interface; intervertebral disc; nucleus pulposus-annulus fibrosus-endplates; cementum-periodontal ligament-alveolar bone; muscle-to-tendon; inhomogeneous or anisotropic tissues; knee meniscus; temporomandibular joint disc; periodontium; root-periodontium complex; synovial joints; or fibrocartilaginous tissues. Features related to methods of treatment can be combined with other features discussed above.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1F are a series of illustrations, images, and a plot showing a spatiotemporal delivery system embedded in 3D-printed scaffold. Selected growth factors (GF) are encapsulated in poly(lactic-co-glycolic acids) (PLGA) microspheres (µS) for controlled release. Further details regarding methodology and results are provided in Example 1, Example 5, Example 6, and Example 7. Scale=100 µm. Further details regarding methodology and results are provided in Example 1 and Example 5.

FIG. 1A shows a two cartridge spatiotemporal delivery system where growth factors (GFs) are encapsulated in PLGA microspheres (µS) for controlled release. PCL and GF-encapsulated µS are mixed in dispensing cartridges of 3D Bioplotter® and heated up to 120° C.

FIG. 1B shows use of use of fluorescent dextran/µS to confirm that PLGA µS were successfully embedded in the 3D-deposited PCL microstrands (see e.g., FIG. 1B). Further details regarding methodology and results are provided in Example 1 and Example 5.

FIG. 1C is a fluorescence image of whole scaffolds showing evenly distributed microspheres in the 3D printed structure. Further details regarding methodology and results are provided in Example 1 and Example 5.

FIG. 1D is a fluorescence image of whole scaffolds showing evenly distributed microspheres in the 3D printed structure. Using fluorescent dextran/µS, it was confirmed that PLGA µS were successfully embedded in the 3D-deposited PCL microstrands, with custom designed scaffold structure/pattern. Further details regarding methodology and results are provided in Example 5.

FIG. 1E is a plot of CTGF, TGFβ3, and BMP-2 delivered in PCL scaffolds via µS embedding showing a sustained release up to 42 days in vitro. The encapsulated CTGF, TGFβ3, and BMP-2 in µS embedded PCL scaffold shows sustained release over 42 days incubation in vitro. Further details regarding methodology and results are provided in Example 5.

FIG. 1F shows the encapsulated growth factor in µS-embedded PCL scaffold had sustained release over 42 days incubation in vitro as shown in a representative data. Further details regarding methodology and results are provided in Example 1 and Example 5.

Given the average fabrication time for a scaffold (~30 mins), temperature over 80% of total volume of microspheres is lower than 45° C., which can preserve bioactivity of encapsulated growth factors. Further details regarding methodology and results are provided in Example 1 and Example 7.

Figures 3A, 3B, 3C:
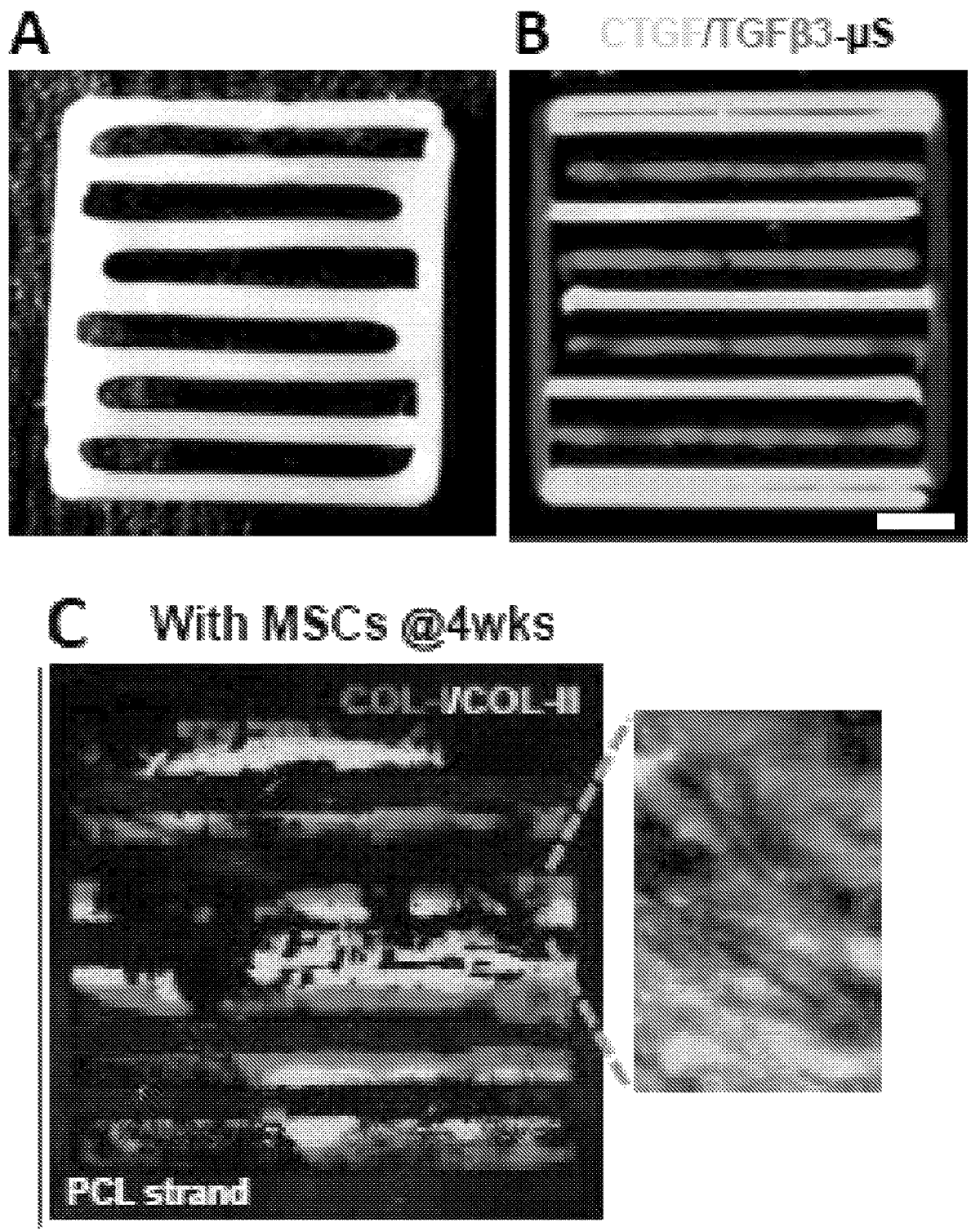

FIG. 3 is a series of images showing formation of multi-tissue interfaces in 3D-printed scaffold with spatiotemporal delivered CTGF and TGFβ3 via PLGA microspheres. FIG. 3A shows a single layered rectangular structure. FIG. 3B shows a single layered rectangular structure constructed with alternative PCL microfibers-embedding CTGF-μS and TGF TGFβ3-μS. The size of microfibers and interfibers space was 100 μm. FIG. 3C shows integrated interface between COL-I+ and COL-II+ matrices was successfully formed within the ~100 μm spaces. Alternative depositions of COL-I+ and COL-II+ matrices were formed after 4 weeks in vitro culture of hMSCs matching the pattern of GF delivery within ~100 μm spaces. Scale=200 μm. Further details regarding methodology and results are provided in Example 1, Example 2, and Example 7.

FIG. 4 shows projected scaffold design with spatiotemporal delivery of growth factors. FIG. 4A shows projected reconstruction of anterior cruciate ligament-fibrocartilage-bone interfaces. FIG. 4B shows projected reconstruction of (supraspinatus tendon-fibrocartilage (unmineralized and mineralized)—bone interfaces. FIG. 4C shows projected reconstruction of cementum (CM)-periodontal ligament (PDL)-alveolar bone (AB) complex. FIG. 4D shows projected recapitulating the gradient matrix distribution and organization in inhomogeneous multiphase tissues, such as TMJ disc and knee meniscus. Histology was adopted from Lu and Thomopoulos 2013 Annu Rev Biomed Eng. 15, 201-226. Further details regarding methodology and results are provided in Example 3.

Figure 5A:
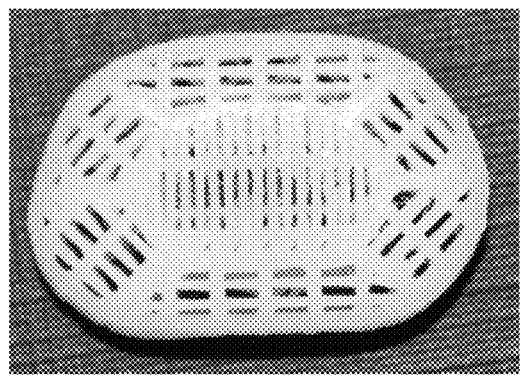
Figure 5B:
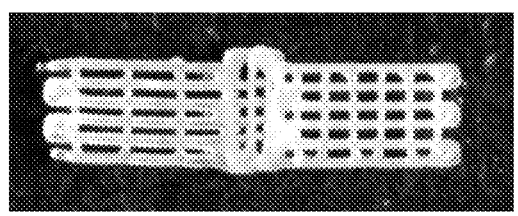
Figure 5C:
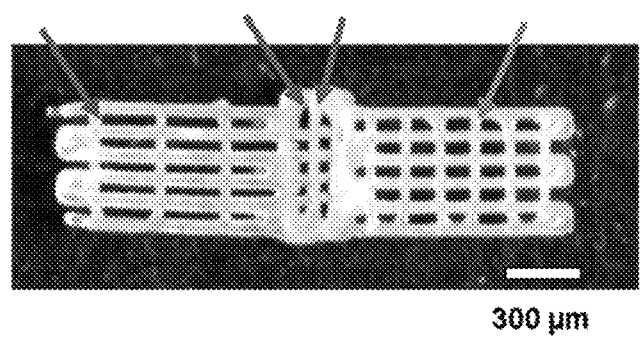

FIG. 5 is a pair of photographs showing a series of images of a TMJ disk scaffold. FIG. 5A and FIG. 5B show views of the TMJ disk scaffold. FIG. 5C shows the TMJ disk scaffold annotated for location in which CTGF, CTGF+TGFβ3, and BMP-2 was embedded.

Figure 6:
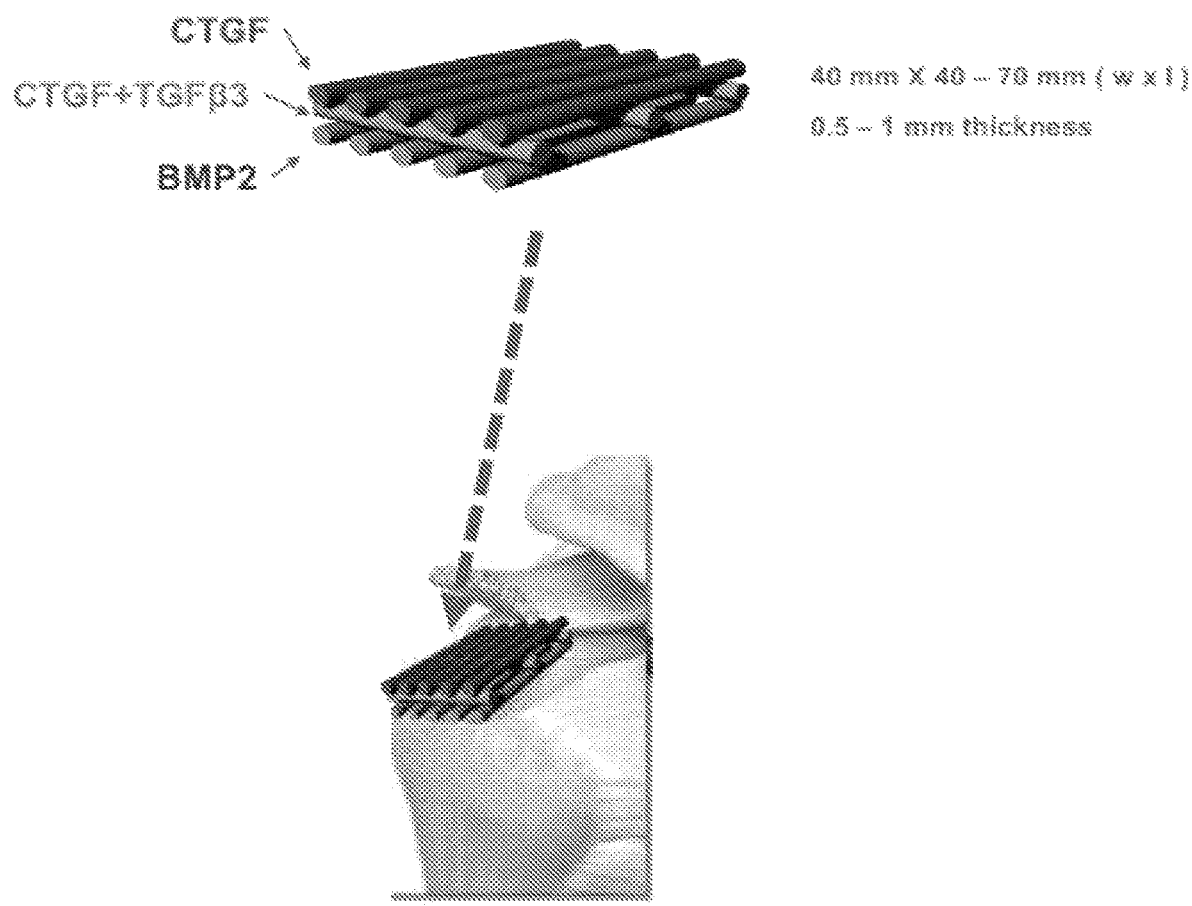

FIG. 6 is an illustration showing a rotator cuff scaffold fabricated with strands having embedded CTGF, CTGF+TGFβ3, and BMP-2 along with location for implantation.

FIG. 7A-FIG. 7F are a series of images and graphs showing preparation of PLGA μS and characterization of GF/μS-embedded PCL scaffold and effects of NaOH treatment on GF release. Further details regarding methodology and results are provided in Example 5.

FIG. 7A is an SEM image of PLGA microspheres (μS).
FIG. 7B is an SEM image of PLGA microspheres (μS).
FIG. 7C is a histogram showing the μS diameter size distribution (mean: 22.68±14.89 μm).
FIG. 7D is a graph showing the mechanical properties of the 3D printed scaffolds, including compressive modulus and ultimate strength, were not significantly altered by embedding 50 mg PLGA μS per 1 g in PCL.
FIG. 7E is an image showing effect of NaOH treatment and effect on growth factor (GF) release behavior.
FIG. 7F is graph showing effect of NaOH treatment and effect on growth factor (GF) release behavior.

FIG. 8A-FIG. 8L are a series of images showing fibrogenic, chondrogenic, and osteogenic differentiation of MSCs in GF/μS embedded 3D printed PCL scaffolds. Further details regarding methodology and results are provided in Example 5.

Figures 8A, 8B, 8C, 8D, 8E, 8F, 8G, 8H, 8I, 8J, 8K, 8L:
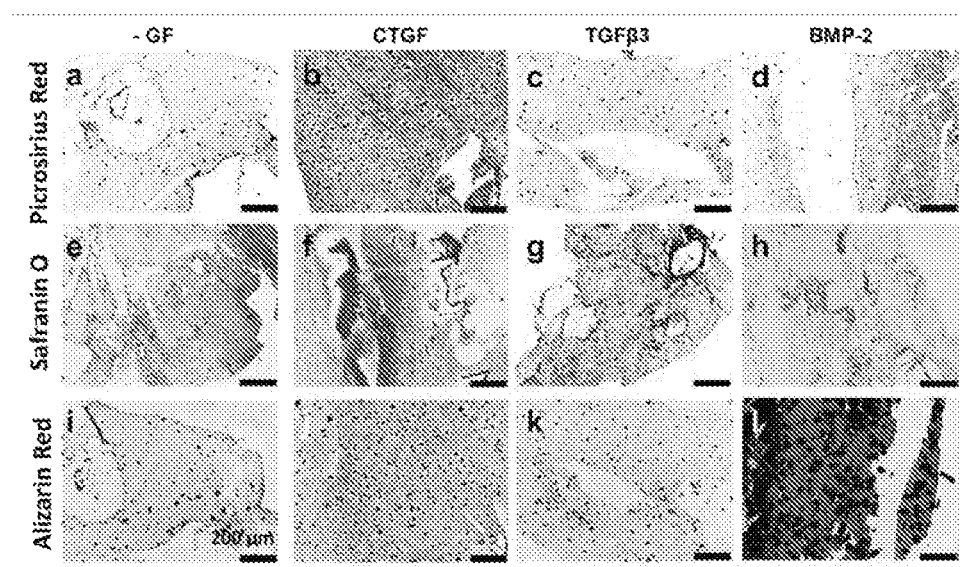

FIG. 8A is a Picrosirius Red (PR) stained section of the 3D printed PCL scaffold after 4 weeks culture with MSCs (−GF).

FIG. 8B is a Picrosirius Red (PR) stained section of the 3D printed PCL scaffold after 4 weeks culture with MSCs (+CTGF).
FIG. 8C is a Picrosirius Red (PR) stained section of the 3D printed PCL scaffold after 4 weeks culture with MSCs (+TGFβ3).
FIG. 8D is a Picrosirius Red (PR) stained section of the 3D printed PCL scaffold after 4 weeks culture with MSCs (+BMP2).
FIG. 8E is a Safranin O (Saf O) stained section of the 3D printed PCL scaffold after 4 weeks culture with MSCs (−GF).
FIG. 8F is a Safranin O (Saf O) stained section of the 3D printed PCL scaffold after 4 weeks culture with MSCs (+CTGF).
FIG. 8G is a Safranin O (Saf O) stained section of the 3D printed PCL scaffold after 4 weeks culture with MSCs (+TGFβ3).
FIG. 8H is a Safranin O (Saf O) stained section of the 3D printed PCL scaffold after 4 weeks culture with MSCs (+BMP2).
FIG. 8I is a Alizarin Red stained section of the 3D printed PCL scaffold after 4 weeks culture with MSCs (−GF).
FIG. 8J is a Alizarin Red stained section of the 3D printed PCL scaffold after 4 weeks culture with MSCs (+CTGF).
FIG. 8K is a Alizarin Red stained section of the 3D printed PCL scaffold after 4 weeks culture with MSCs (+TGFβ3).
FIG. 8L is a Alizarin Red stained section of the 3D printed PCL scaffold after 4 weeks culture with MSCs (+BMP2).

FIG. 9A-FIG. 9E are a series of images showing the formation of multi-tissue interfaces in a 3D-printed scaffold with spatiotemporal delivery of CTGF and TGFβ3 via PLGA microspheres. Further details regarding methodology and results are provided in Example 5.

Figures 9A, 9B, 9C, 9D, 9E:
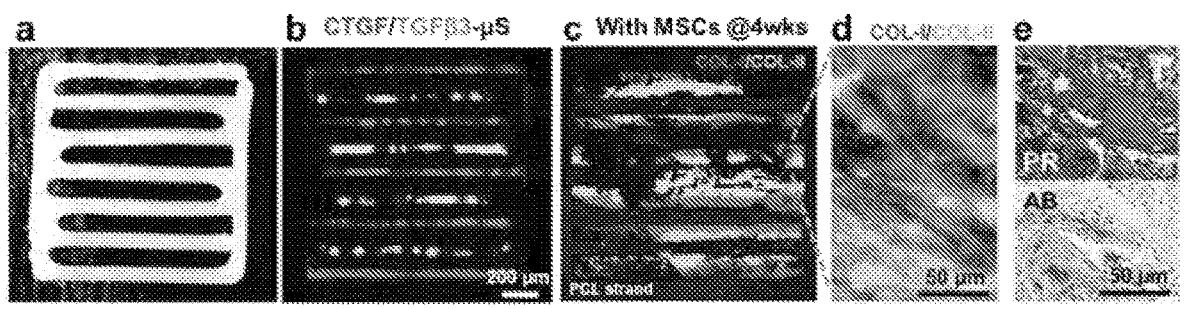

FIG. 9A is an image of a single layered rectangular scaffold (1.5×1.5 mm) fabricated with parallel oriented PCL microfibers (100 μm) and inter-fibers channels (100 μm).

FIG. 9B is an image showing the PCL microfibers alternatingly embedded with CTGF and TGFβ3 μS.

FIG. 9C is an immunofluorescence image showing integrated interfaces of COL-I+ and COL-II+ matrices within the 100 μm microchannels with MSCs at weeks corresponding to the alternatingly located CTGF and TGFβ3 in FIG. 9B.

FIG. 9D is an enlarged section of FIG. 9C showing integrated interfaces of COL-I+ and COL-II+ matrices within the 100 μm microchannels with MSCs at weeks corresponding to the alternatingly located CTGF and TGFβ3 in FIG. 9B.

FIG. 9E is a series of histology images showing integrated interfaces of COL-I+ and COL-II+ matrices within the 100 μm microchannels with MSCs at weeks corresponding to the alternatingly located CTGF and TGFβ3 in FIG. 9B.

Figures 10A, 10B, 10C:
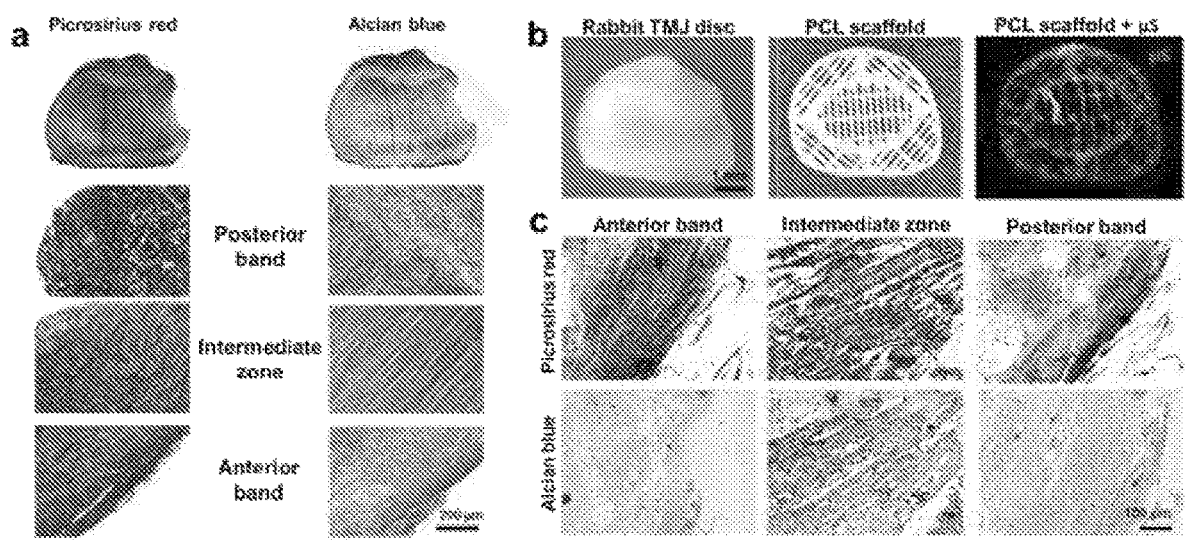

FIG. 10A-FIG. 10C are a series of images showing in vitro tissue engineering of rabbit TMJ disc. Picrosirius red (PR) and Alcian blue (AB) staining of whole sections of rabbit TMJ disc show anisotropic collagen orientation and regionally distributed cartilaginous matrix (see e.g., FIG. 10A). Collagen was distributed throughout the disc with a circumferential orientation in the posterior and anterior bands, and an anteroposterior orientation 556 in the intermediate zone. AB+ cartilaginous matrix was predominantly located in the intermediate zone with rounded chondrocyte-like cells (see e.g., FIG. 10A). From the anatomical contour of native rabbit TMJ disc, 3D printed scaffolds were fabricated with the anisotropic alignment of microstrands and delivery of CTGF and TGFβ3 μS mimicking the regionally distributed fibrocartilaginous matrix (see e.g., FIG. 10B). After 6 weeks culture with MSCs, CTGF/TGFβ3 μS-embedded scaffolds formed densely oriented fibrous tissue in the posterior and anterior bands, whereas fibrocartilaginous tissue in the intermediate zone, reminiscent of native tissue (see e.g., FIG. 10C). Further details regarding methodology and results are provided in Example 5.

FIG. 10A is a series of images showing Picrosirius red (PR) and Alcian blue (AB) stained sections demonstrating the anisotropic collagen orientation and regionally variant fibrocartilaginous matrix in native rabbit TMJ discs.

FIG. 10B is an image of an anatomically correct rabbit TMJ disc scaffold fabricated with 100 μm PCL strands and inter-strands microchannels.

FIG. 10C is a series of images showing Picrosirius red (PR) and Alcian blue (AB) stained sections after 6 weeks culture with MSCs either from human bone marrow or rabbit TMJ synovium. Multiphase fibrocartilaginous tissue with densely aligned fibrous matrix was observed in the anterior and posterior bands and fibrocartilaginous matrix in the intermediate zone.

Figures 11A, 11B:
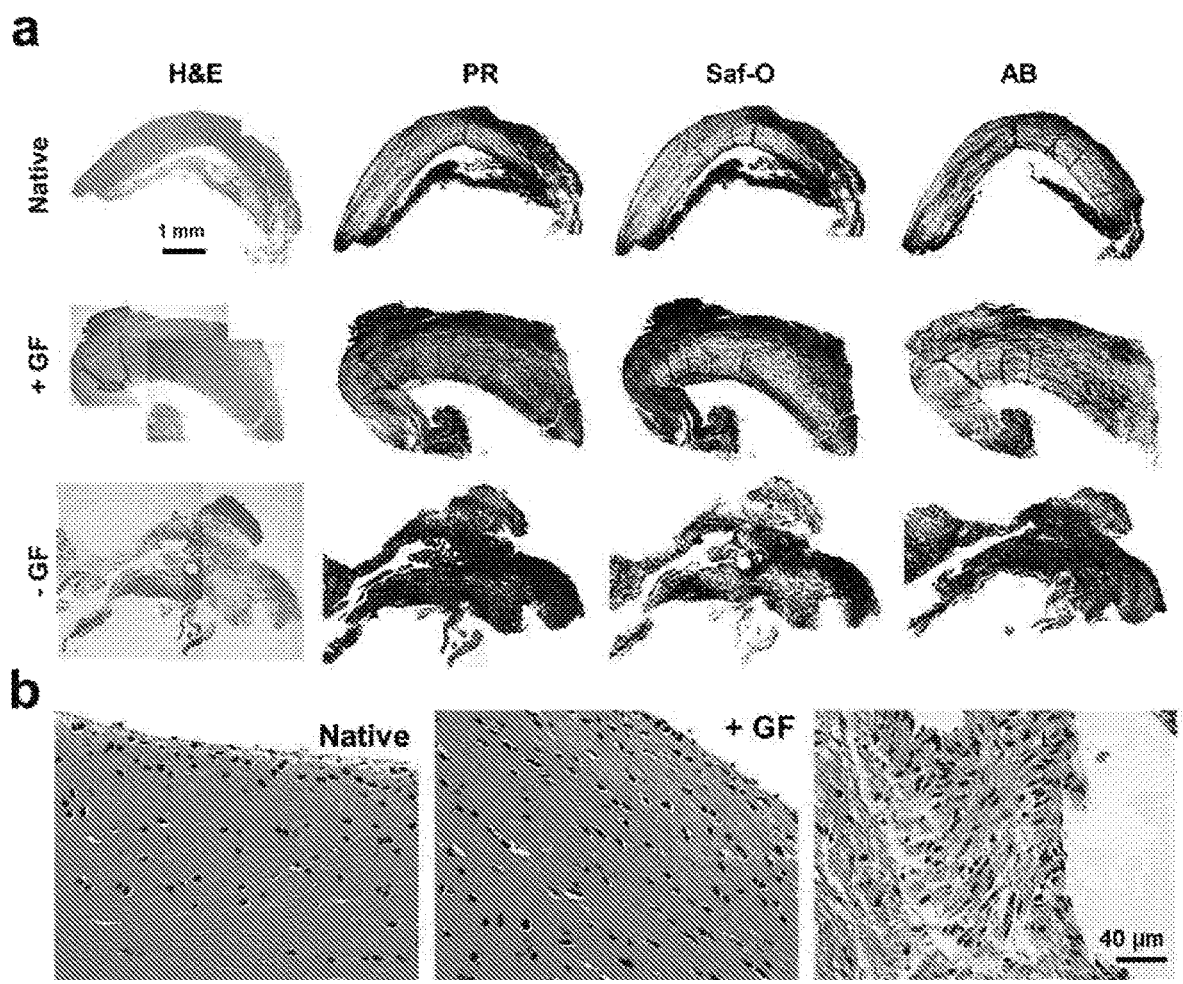

FIG. 11A-FIG. 11B are a series of images showing in vivo healing of rabbit TMJ disc by 3D printed scaffolds. Upon performing 2.5 mm disc perforation, 3D printed scaffolds (with or without GFs) were implanted. After 4 weeks, vertical tissue sections with H&E, PR, Saf-O, and AB staining showed that CTGF/TGFβ3 μS-embedded scaffolds led to a full recovery of perforated disc with multiphase fibrocartilaginous tissue similar to native TMJ disc, whereas empty μS-embedded scaffolds resulted in severe disc degeneration with loss of fibrocartilage (see e.g., FIG. 11A). In addition, healed TMJ disc with CTGF/TGFβ3 μS-embedded scaffolds restored rounded chondrocyte-like cell phenotype on the disc surface, reminiscent of native (see e.g., FIG. 11B). In contrast, degenerating disc with empty μS show a loss of chondrocyte-like cells (see e.g., FIG. 11B). Further details regarding methodology and results are provided in Example 5.

FIG. 11A is a series of images showing H&E, Picrosirius red (PR), Saf-O, and Alcian blue (AB) stained sections of 3D printed μS-embedded TMJ scaffold, in vivo, after 6 weeks implantation in Native TMJ, μS-embedded scaffold +GF, and μS-embedded scaffold -GF.

FIG. 11B is an image of high magnification histology showing the rounded chondrocyte-like cell population on the surface of after 6 weeks implantation in Native TMJ, μS-embedded scaffold +GF, and μS-embedded scaffold -GF.

FIG. 12A-FIG. 12E are a series of images and bar graphs evaluating arthritic changes on mandibular condyle. Gross images showed no noticeable damage or structural changes on the articular cartilage of mandibular condyle (see e.g., FIG. 12A). No sign of cartilage defects on the articular surface of TMJ condyle were observed after 4 weeks implantation of GF/μS-embedded scaffolds, whereas scaffold without growth factor resulted in some vertical erosions in cartilage, as compared to native articular cartilage (see e.g., FIG. 12B-FIG. 12C). Quantitatively, the cartilage thickness without GF was significantly thinner than native and the GF/μS-embedded scaffolds (see e.g., FIG. 12D) (*: $p<0.05$; n=5 per group). Consistently, OARSI osteoarthritis score was significantly lower with GF/μS-em bedded scaffolds than scaffolds without GF (see e.g., FIG. 12E) (*: $p<0.05$; n=5 per group). Further details regarding methodology and results are provided in Example 5.

FIG. 12A is a series of images of resected native TMJ condyle, μS-embedded scaffold +GF TMJ condyle, and μS-embedded scaffold -GF TMJ condyle.

FIG. 12B is a series of images showing H&E stained sections of native TMJ condyle, μS-embedded scaffold +GF TMJ condyle, and μS-embedded scaffold -GF TMJ condyle.

FIG. 12C is a series of images showing Safranin-O stained sections of native TMJ condyle, μS-embedded scaffold +GF TMJ condyle, and μS-embedded scaffold -GF TMJ condyle.

FIG. 12D is a bar graph showing cartilage thickness with no growth factor (-GF) was significantly thinner than native and the GF/μS-embedded scaffolds.

FIG. 12E is a bar graph showing OARSI osteoarthritis score was significantly lower with GF/μS-embedded scaffolds than scaffolds without GF.

Figures 13A, 13B, 13C:
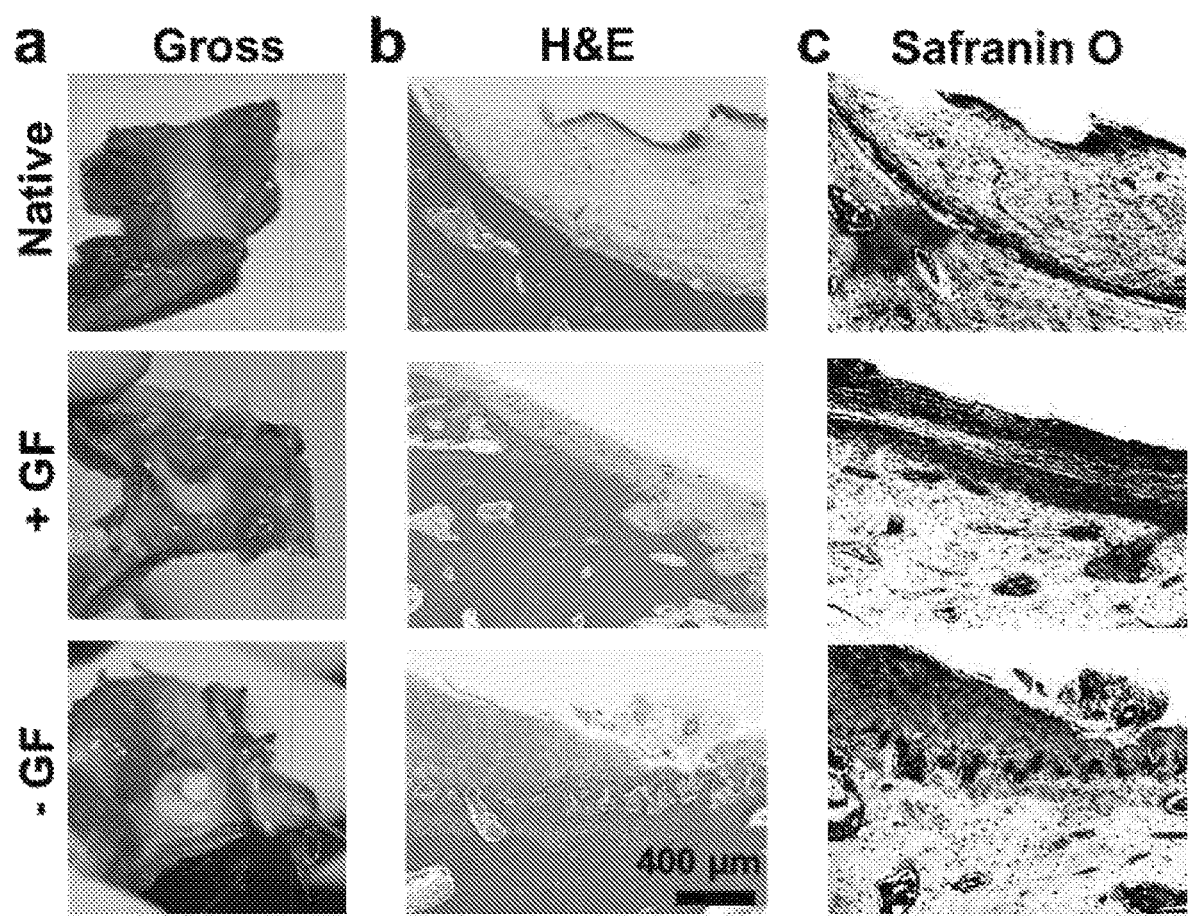

FIG. 13A-FIG. 13C are a series of images showing the glenoid fossa after 4 weeks scaffold implantation. Gross images show no noticeable cartilage defect or structural changes in the glenoid fossa (see e.g., FIG. 13A). Histologically, a denser Saf-O positive cartilage layer was observed with GF/μS-embedded scaffolds as compared to the native with no noticeable sign of cartilage defects (see e.g., FIG. 13B-FIG. 13C). Further details regarding methodology and results are provided in Example 5.

FIG. 13A is a series of images of the of the native glenoid fossa, μS-embedded scaffold +GF glenoid fossa, and μS-embedded scaffold -GF glenoid fossa of the TMJ condyle.

FIG. 13B is a series of images of H&E stained sections of the native glenoid fossa, μS-embedded scaffold +GF glenoid fossa, and μS-embedded scaffold -GF glenoid fossa of the TMJ condyle.

FIG. 13C is a series of images of Safranin-O stained sections of the native glenoid fossa, μS-embedded scaffold +GF glenoid fossa, and μS-em bedded scaffold -GF glenoid fossa of the TMJ condyle.

FIG. 14A-FIG. 14I are a series of images and graphs characterizing a TMJ disc scaffold. Further details regarding methodology and results are provided in Example 6.

Figures 14A, 14B, 14C:
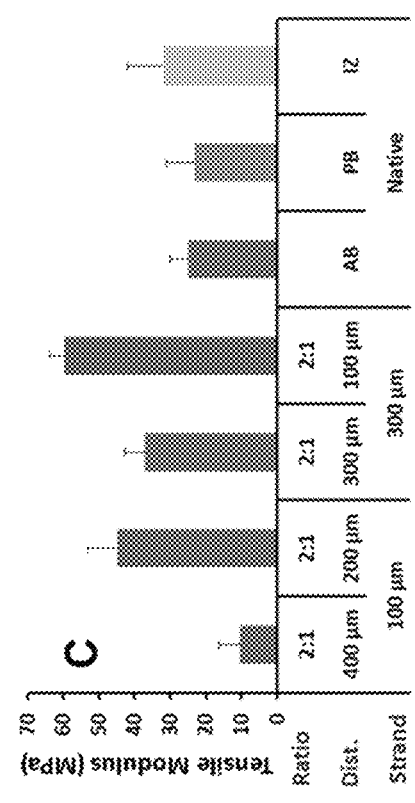

FIG. 14A is an image of the 3D model for a 3D-printed TMJ disc scaffold.

FIG. 14B is an image of a TMJ disc scaffold constructed with repeating microstrands and interstrand microchannels with their orientation predominantly in the circumferential and anteroposterior directions in the peripheral ring and intermediate zone, respectively mimicking native anisotropic collagen alignment.

FIG. 14C is a bar graph showing the size of PCL microstrands (300 μm) and microchannels (300 μm) and the relative density of microstrands parallel to versus perpendicular to the alignment direction (2:1) and were determined to closely approximate the tensile properties of those of native disc in the circumferential and anteroposterior directions, respectively.

Figures 14D, 14E:
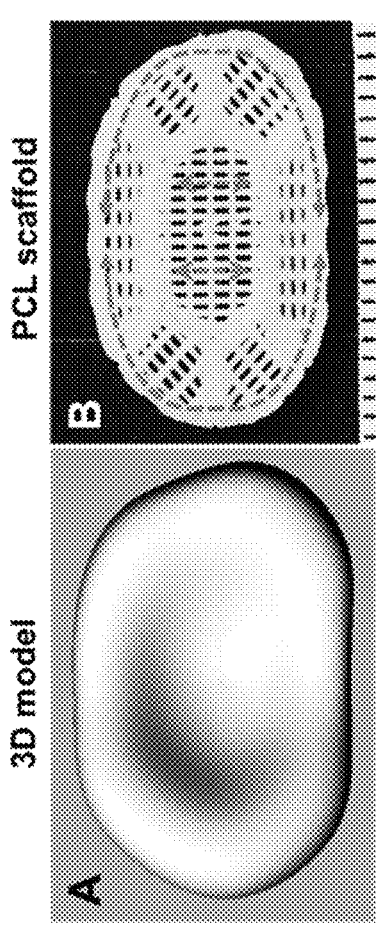

FIG. 14D is a representative fluorescence image with μS-encapsulating Alex Fluora® 488 and 546 demonstrating that CTGF is delivered throughout the scaffolds whereas CTGF and TGFβ3 are delivered in the intermediate zone of the TMJ disc scaffolds.

FIG. 14E is a graph showing CTGF and TGFβ3 delivered in the scaffold showed a sustained release up to 42 days in vitro.

Figures 14F, 14G:
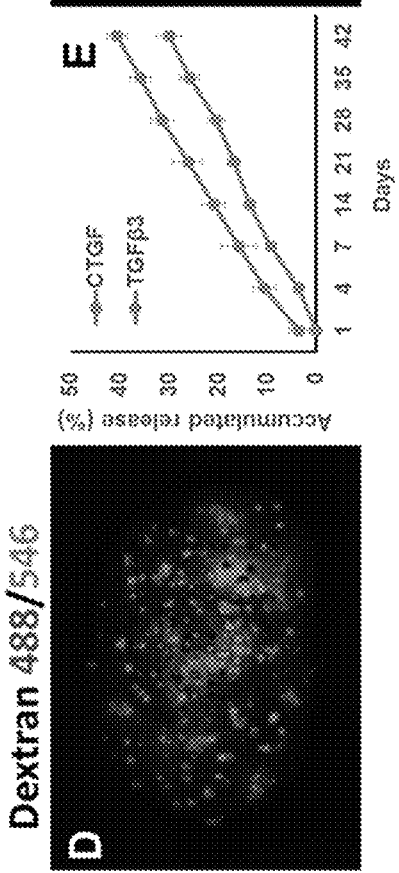

FIG. 14F is an image of a TMJ disc scaffold cultured with MSCs (2 M/mL) for 6 weeks without μS.

FIG. 14G is an image of a TMJ disc scaffold cultured with MSCs (2 M/mL) for 6 weeks with spatiotemporal delivery of CTGF and TGFβ3 in μS.

Figures 14H, 14I:
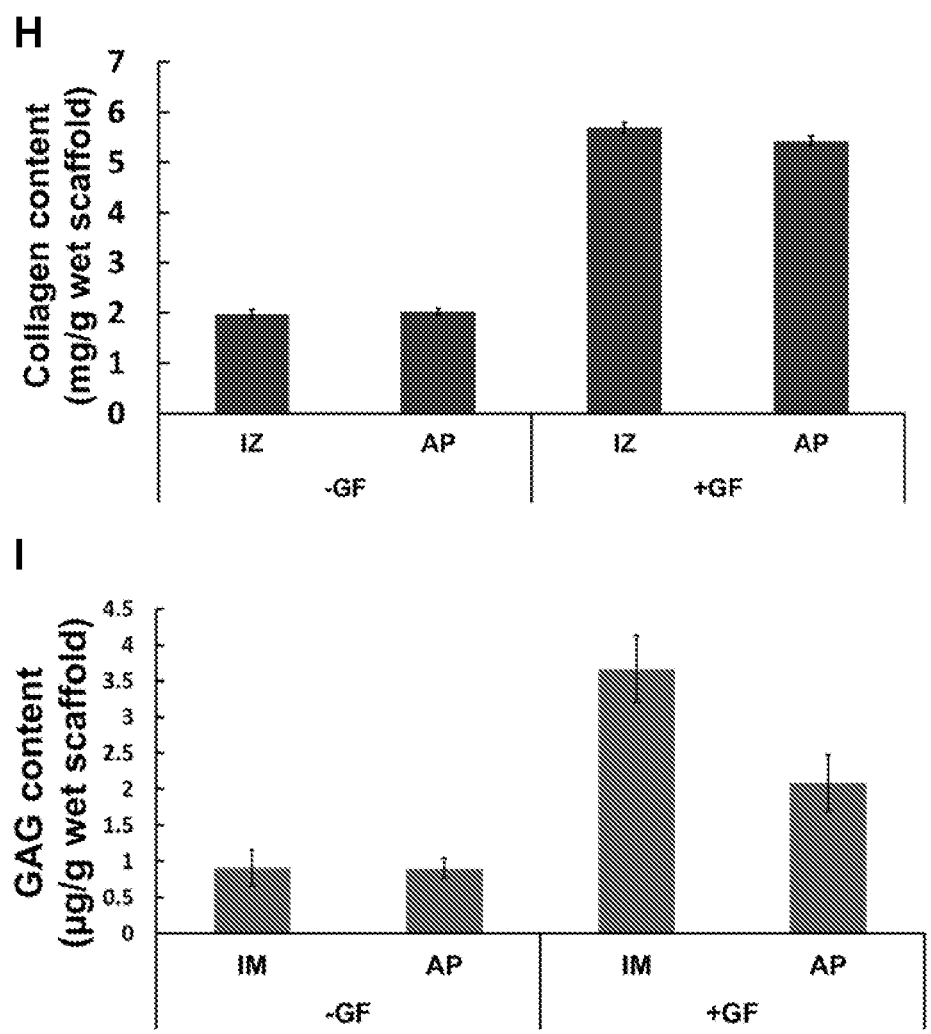

FIG. 14H is a bar graph showing collagen content per wet weight was significantly higher both in the intermediate zone (IZ) and the anterior/posterior band (AP) with GF delivery as compared to control without GF ($p<0.05$; $n=5$ per group).

FIG. 14I is a bar graph showing GAGs content was significantly higher with GF delivery as compared to control (see e.g., FIG. 14I) ($p<0.05$; $n=5$ per group). IZ showed significantly higher GAGs content than AP ($p<0.05$; $n=5$ per group).

Figures 15A, 15B:
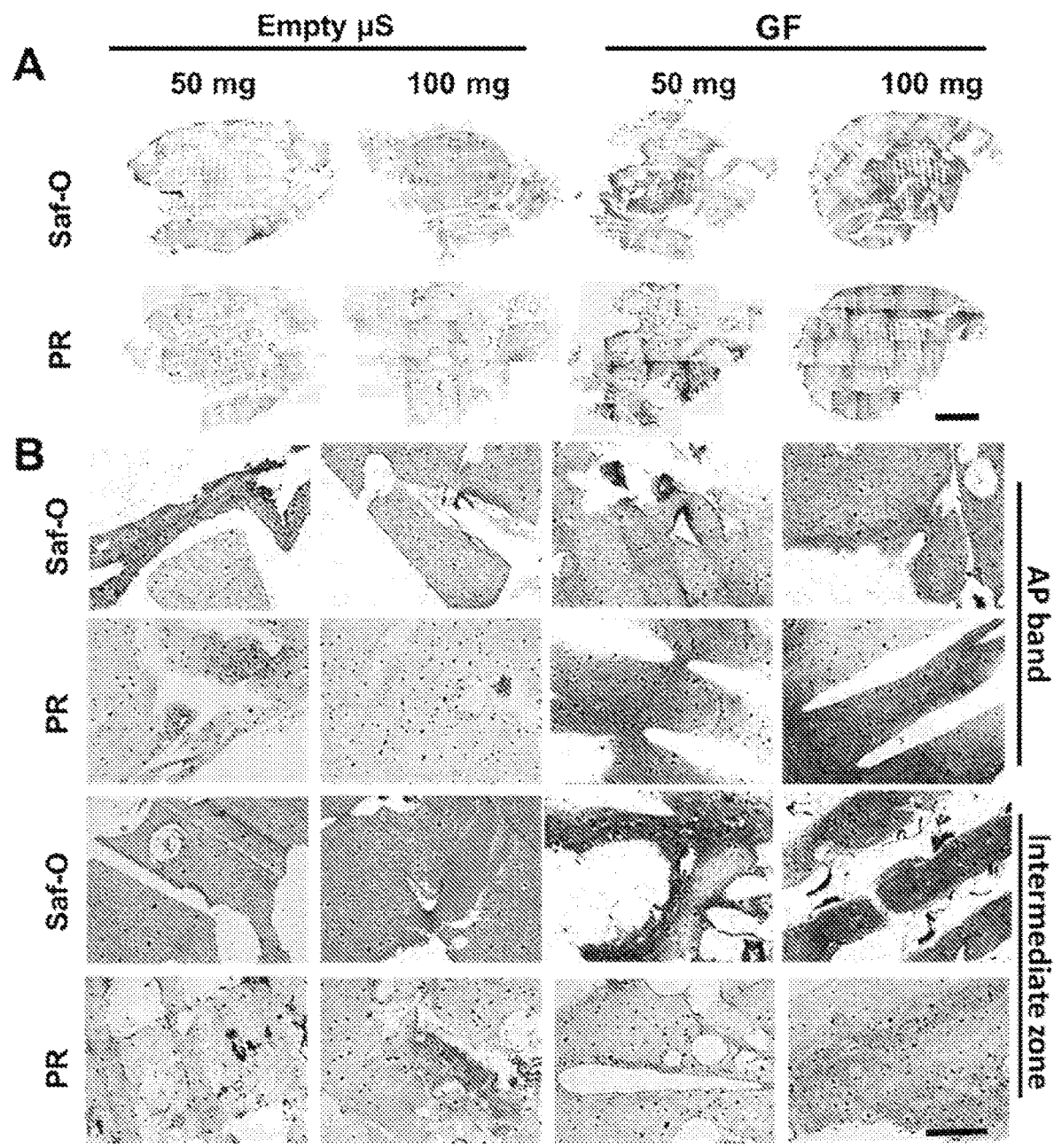

FIG. 15A is a series of PR and Saf-O stained sections of TMJ disc showing, after 6 weeks culture with MSCs, growth factor (GF; CTGF and TGFβ3) encapsulated μS-embedded scaffolds formed heterogeneous fibrocartilage featured by Saf-O-positive cartilaginous matrix in the intermediate zone and PR-positive denser collagenous tissue in the AP bands. The high dose (100 mg μS/g PCL) showed likely denser cartilaginous matrix in the intermediate zone as compared to low dose (50 mg μS/g PCL). Further details regarding methodology and results are provided in Example 6.

FIG. 15B is a series of higher magnification images of PR and Saf-O stained sections of the AP band and intermediate zone with and without GF showing higher density of collagenous tissue in the AP bands and fibrocartilaginous tissue in the intermediate zone with GF/μS-embedded scaffolds, in comparison to empty μS-embedded scaffolds.

Figure 15C:
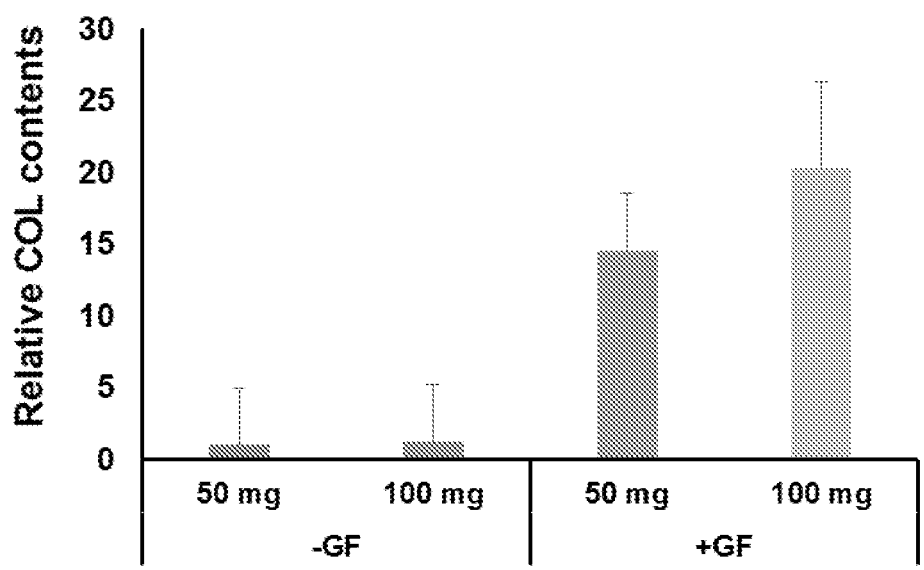

FIG. 15C is a bar graph showing total collagen content in the AP bands were significantly higher with the high dose as compared to low dose of GF/μS and empty/μS ($p<0.05$; $n=5$ per group).

Figure 15D:
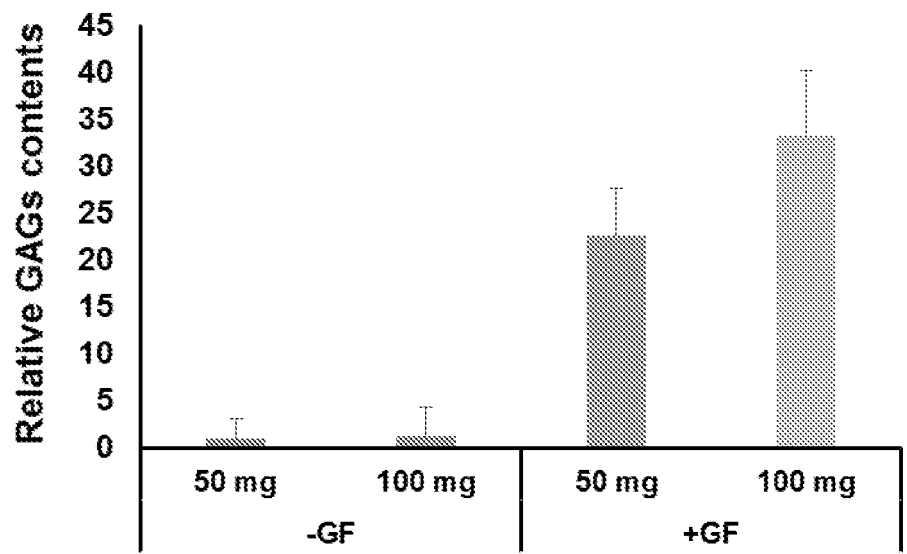

FIG. 15D is a bar graph showing total GAGs content in the IZ were significantly higher with the high dose as compared to the low dose of GF/μS and empty/μS.

FIG. 16A is a series of immunofluorescence images showing that both high and low doses of GF/μS resulted in COL-II+/AGC+ fibrocartilaginous tissue in the intermediate zone, not in the AP bands. No COL-II and AGC were found with the empty μS. Consistently, denser COL-I+ matrix was formed with GF/μS both in high and low doses in the AP bands, in comparison with the empty μS. Further details regarding methodology and results are provided in Example 6.

FIG. 16B is a bar graph showing relative areas positive for COL-II and AGC were significantly wider in for the high dose as compared to the low dose. Further details regarding methodology and results are provided in Example 6.

FIG. 16C is a bar graph showing qRT-PCR showed significantly more COL-I mRNA expression with the GF/μS for high and low doses as compared to empty μS. Further details regarding methodology and results are provided in Example 6.

Figure 17C:
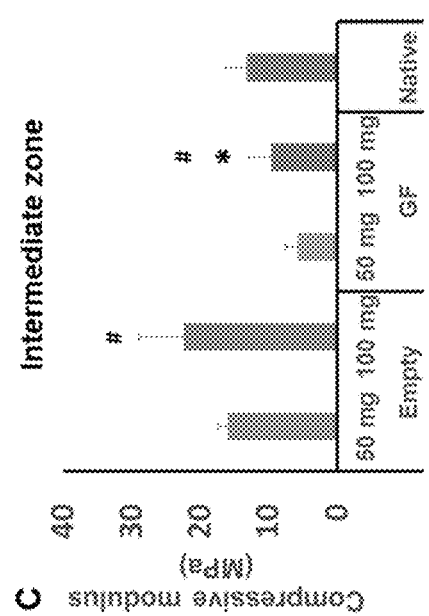
Figure 17B:
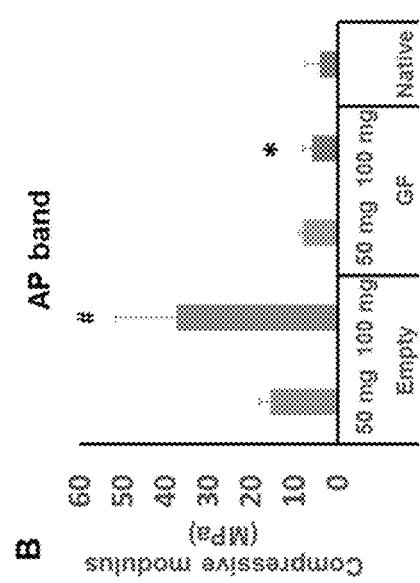
Figure 17A:
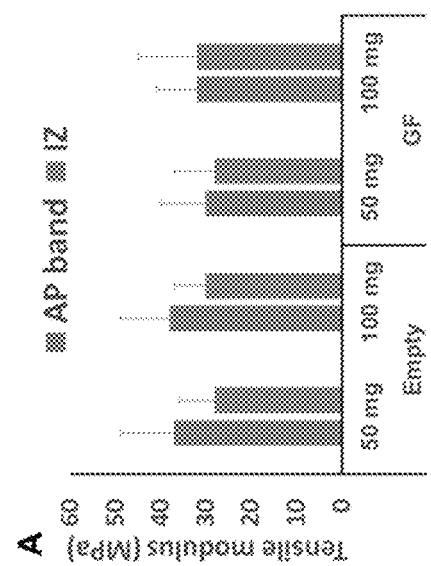

FIG. 17A is a bar graph showing no statistically significant difference in the tensile modulus to the direction of PCL microstrand alignment between GF/μS and empty μS after 6 weeks culture with MSCs. Further details regarding methodology and results are provided in Example 6.

FIG. 17B is a bar graph showing the compressive modulus was significantly higher in the high dose (100 mg μS/g PCL) empty μS than the low dose (50 mg μS/g PCL) in the AP bands. Further details regarding methodology and results are provided in Example 6.

FIG. 17C is a bar graph showing the compressive modulus was significantly higher in the high dose (100 mg μS/g PCL) empty μS than the low dose (50 mg μS/g PCL) in the Intermediate Zone (IZ). Further details regarding methodology and results are provided in Example 6.

FIG. 18A is a bar graph showing instantaneous (Ei) were significantly lower in high dose GF/μS than empty μS in the AP band. Further details regarding methodology and results are provided in Example 6.

FIG. 18B is a bar graph showing relaxation moduli (Er) were significantly lower in high dose GF/μS than empty μS both in the AP band. Further details regarding methodology and results are provided in Example 6.

FIG. 18C is a bar graph showing the ratio of Er to Ei was significantly smaller in the high dose GF/μS as compared to all the other groups, more approximating the native property. Further details regarding methodology and results are provided in Example 6.

FIG. 18D is a bar graph showing the coefficient of viscosity (μ) was significantly higher with GF/μS as compared to empty μS both in AP bands. Further details regarding methodology and results are provided in Example 6.

FIG. 18E is a bar graph showing is a bar graph showing instantaneous (Ei) were significantly lower in high dose GF/μS than empty μS in the intermediate zone. Further details regarding methodology and results are provided in Example 6.

FIG. 18F is a bar graph showing is a bar graph showing relaxation moduli (Er) were significantly lower in high dose GF/μS than empty μS both in the intermediate zone. Further details regarding methodology and results are provided in Example 6.

FIG. 18G is a bar graph showing is a bar graph showing the ratio of Er to Ei was significantly smaller in the high dose GF/μS as compared to all the other groups, more approximating the native property. Further details regarding methodology and results are provided in Example 6.

FIG. 18H is a bar graph showing is a bar graph showing the coefficient of viscosity (μ) was significantly higher with GF/μS as compared to empty μS both in the intermediate zone. Further details regarding methodology and results are provided in Example 6.

Figure 19A:
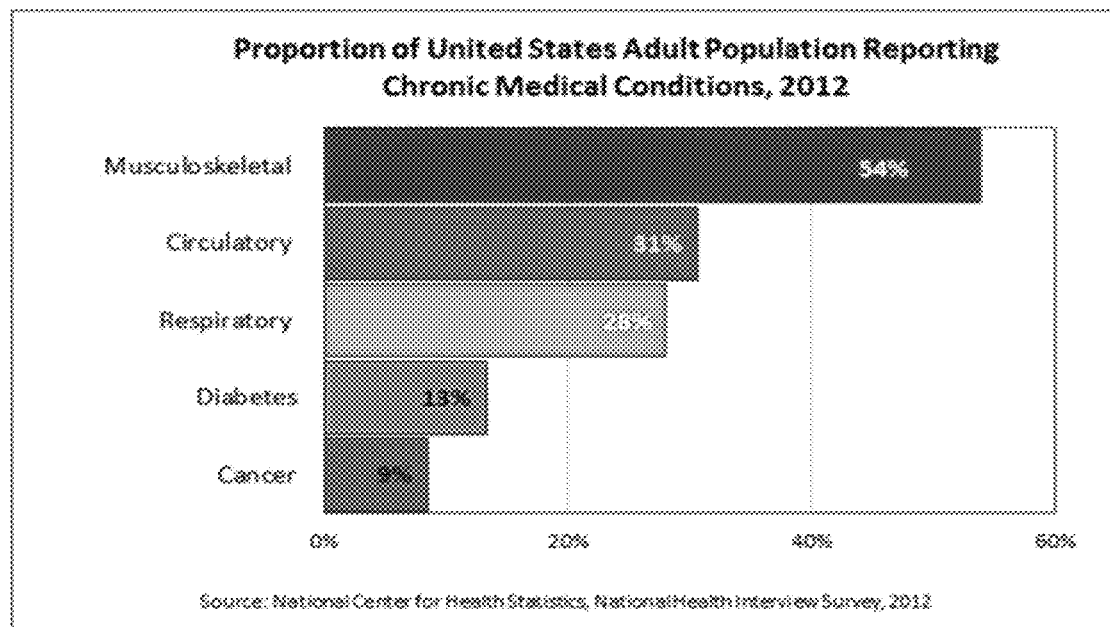

FIG. 19A is a bar graph showing that on an age-adjusted basis, musculoskeletal conditions are reported by 54 persons per every 100 in the population in US.

Figure 19B:
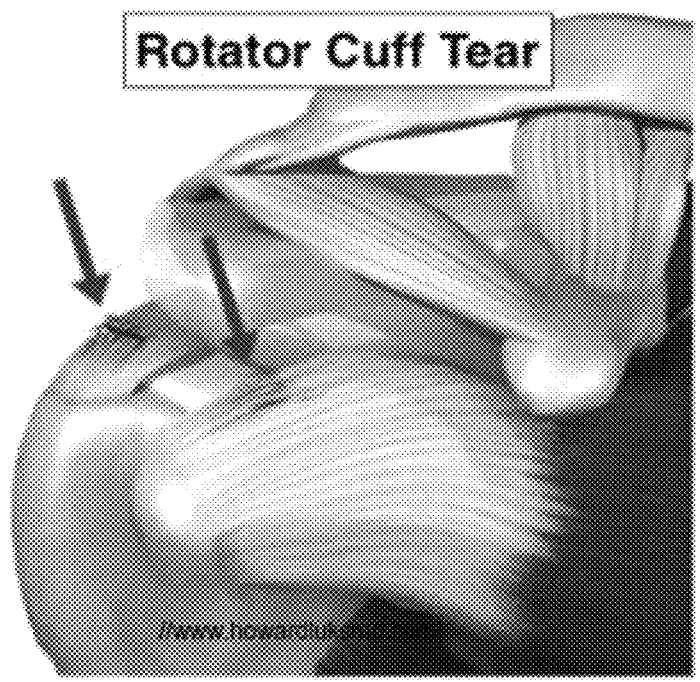

FIG. 19B is an illustration of a rotator cuff tear.

FIG. 20 is a series of illustrations and images showing rotator cuff and ligament-bone scaffolds. Scaffold design for bone to tendon integrated multi-tissue formation. Application for rotator cuff repair graft with three layers 3D printed PCL/PGLA μS: PCUCTGF+TGFβ3 μS layer sandwiched between PCL/CTGF μS and PCL/BMP2 μS. Further details regarding methodology and results are provided in Example 4 and Example 7.

Figure 21:
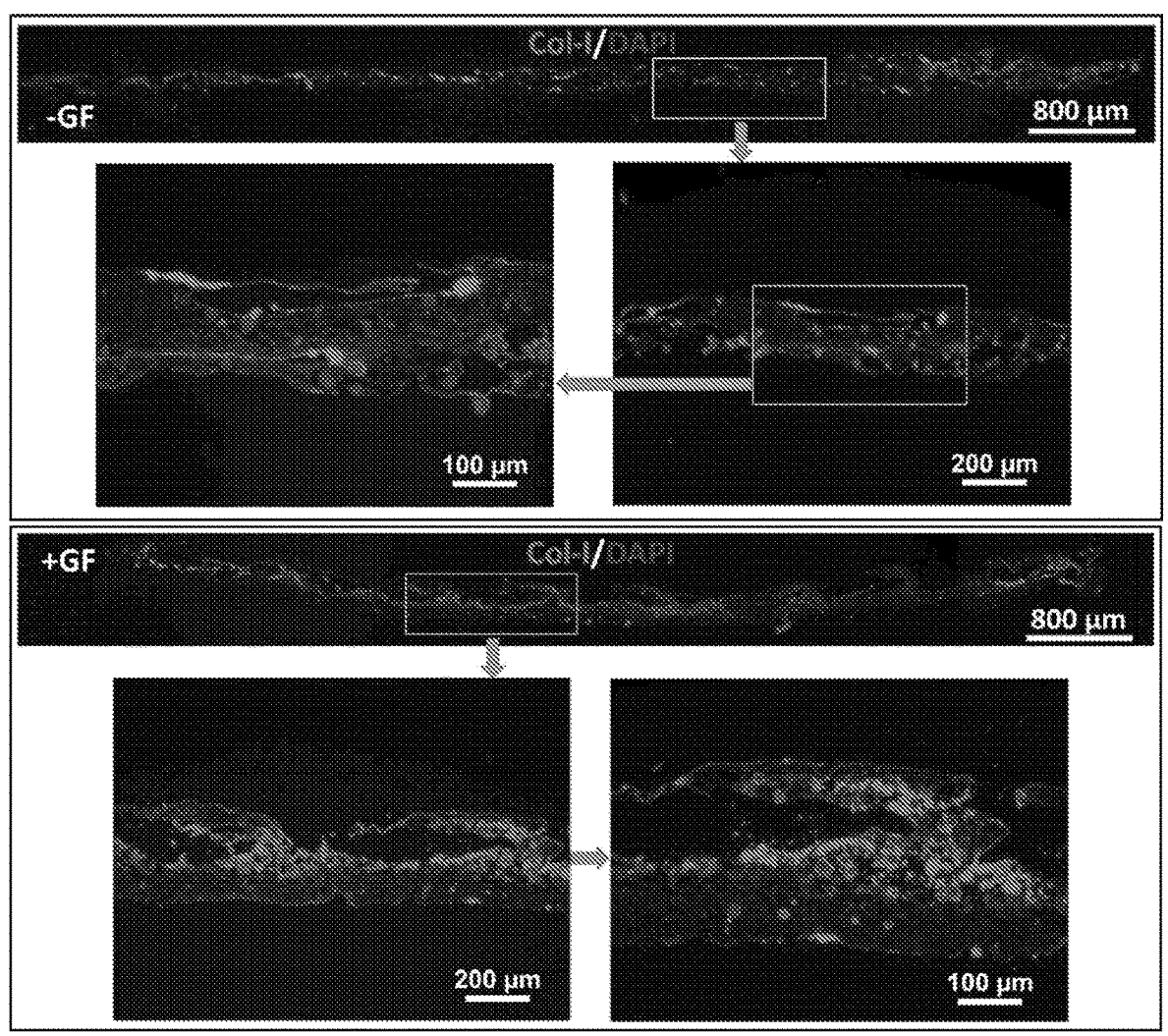

FIG. 21 is a series of fluorescence images of tendon-bone scaffolds at 6 weeks with hMSCs (2 M/mL). +GF group induced higher collagen I expression than the −GF group. Further details regarding methodology and results are provided in Example 7.

Figure 22A:
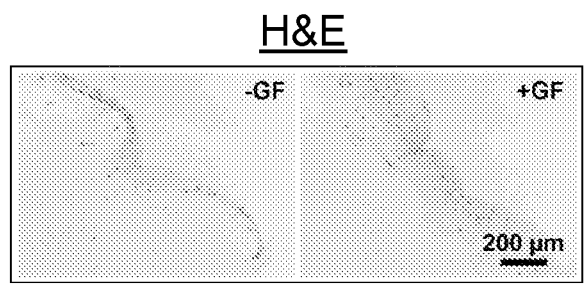
Figure 22B:
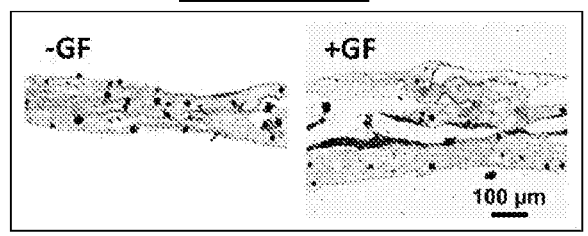
Figure 22C:
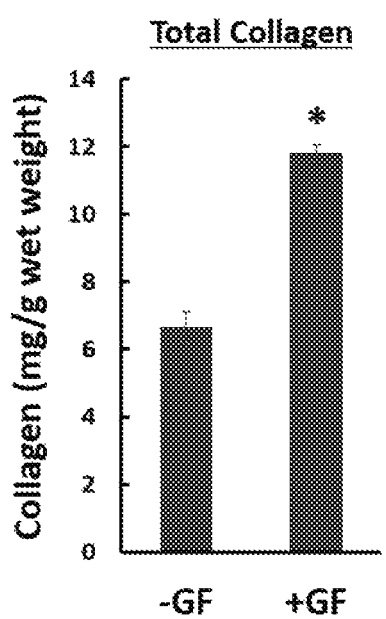

FIG. 22A-FIG. 22C are a series of microscopy images of tendon-bone scaffolds at 6 weeks with hMSCs (2 M/mL) with and without GF and a bar graph of total collagen of tendon-bone scaffolds at 6 weeks with hMSCs (2 M/mL) with and without GF. +GF group induced higher collagen I expression than the −GF group. Further details regarding methodology and results are provided in Example 7.

FIG. 22A is an H&E stained section of tendon-bone scaffolds at 6 weeks with hMSCs (2 M/mL) with and without GF.

FIG. 22B is a Trichrome Blue stained section of tendon-bone scaffolds at 6 weeks with hMSCs (2 M/mL) with and without GF.

FIG. 22C shows +GF group induced higher collagen I expression than the −GF group.

Figure 23:
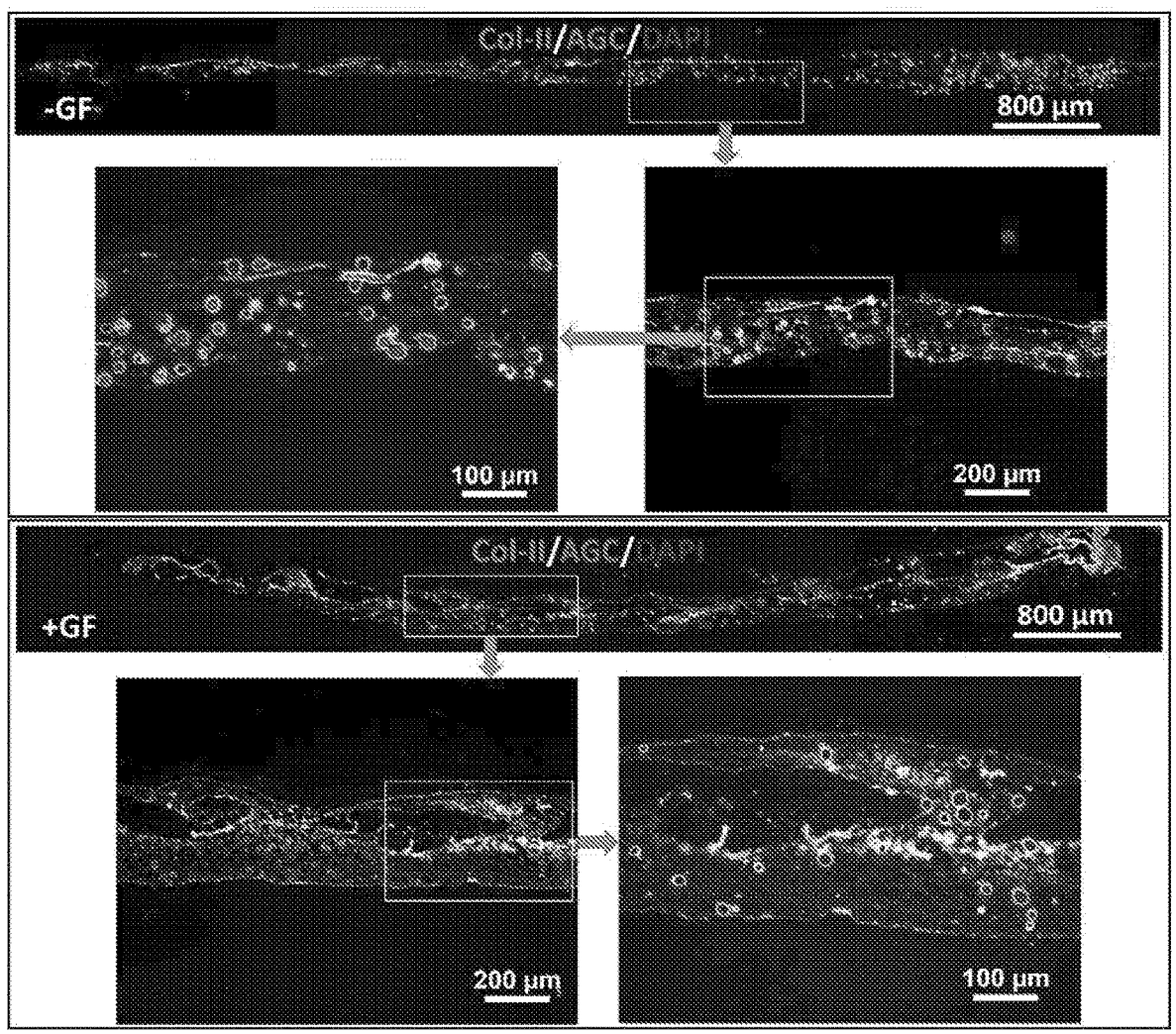

FIG. 23 is a series of fluorescence images of Col-II & Aggrecan at 6 weeks with hMSCs. −GF group did not show any aggrecan (AGC) expression in the ECM. Further details regarding methodology and results are provided in Example 7.

Figure 24:
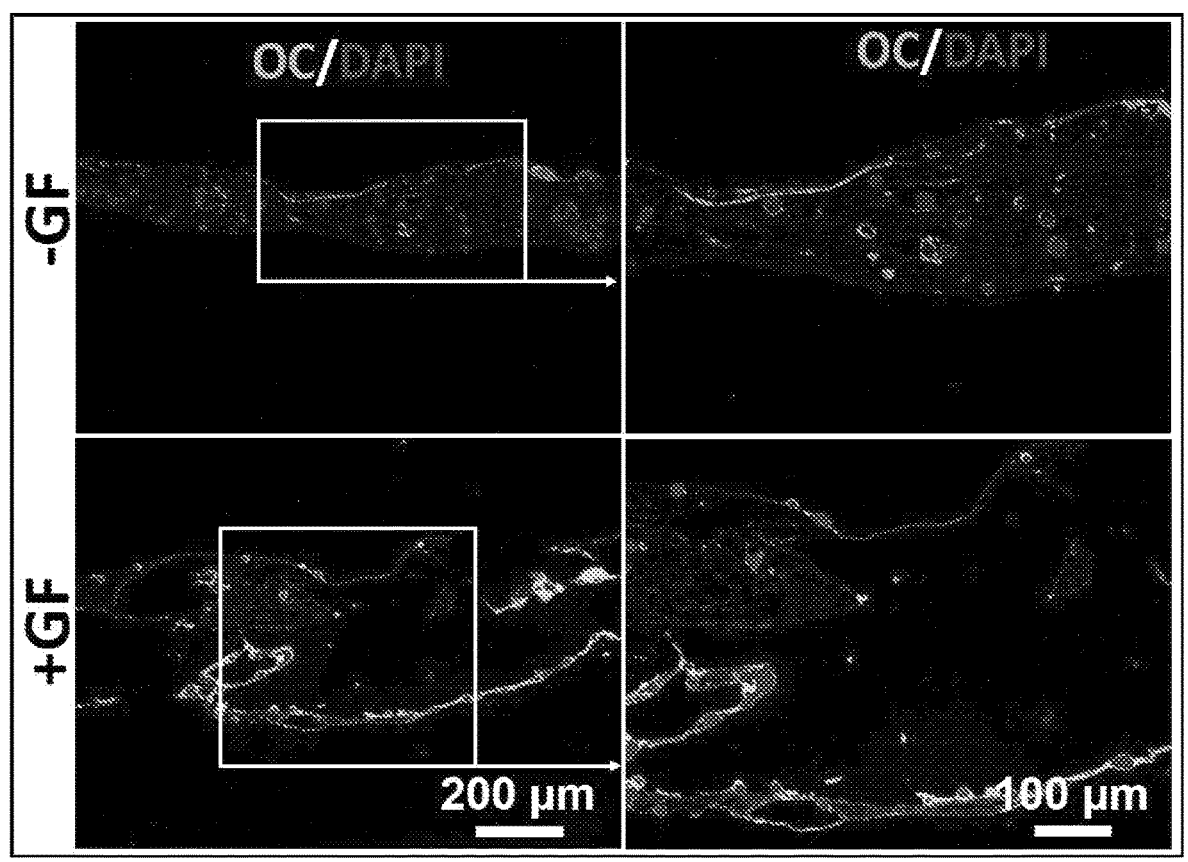

FIG. 24 is a series of fluorescence images of osteocalcin expression at 6 weeks with hMSCs with and without GF. Only the BMP2 layer in the +GF group showed osteocalcin (OC) expression. Further details regarding methodology and results are provided in Example 7.

FIG. 25 is a series of microscopy images of Alizarin Red stained sections of osteocalcin expression at 6 weeks with hMSCs with and without GF. Only the BMP2 layer in the +GF group showed osteocalcin (OC) expression. Further details regarding methodology and results are provided in Example 7.

Figure 26A:
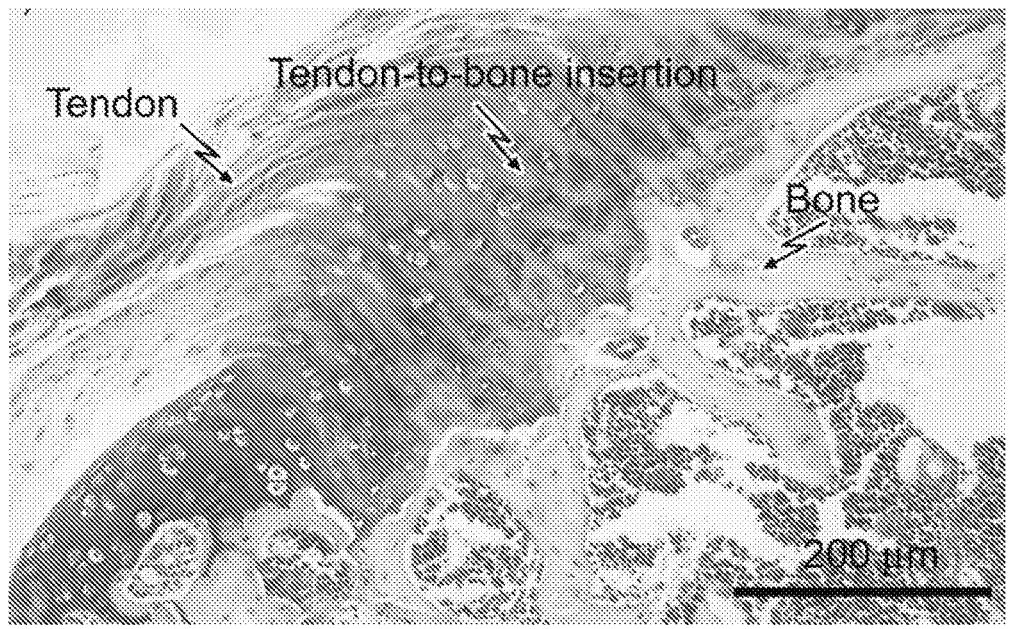

FIG. 26A is an image showing engineered tendon-bone interface (Smith et al., Connective Tissue Research, 53(2): 95-105, (2012)). Further details regarding methodology and results are provided in Example 7.

Figure 26B:
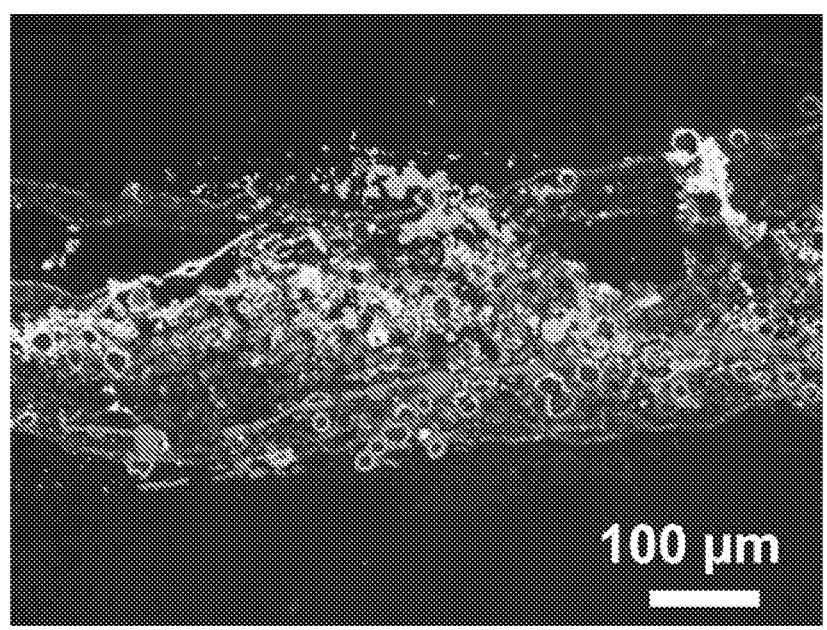

FIG. 26B is an immunofluorescence image showing region specific expression of OC, Col-I, Col-II, and AGC showing the spatiotemporal delivery system for engineering tendon-bone interfaces with native like fibrocartilaginous gradient matrix. Further details regarding methodology and results are provided in Example 7.

Figure 27A:
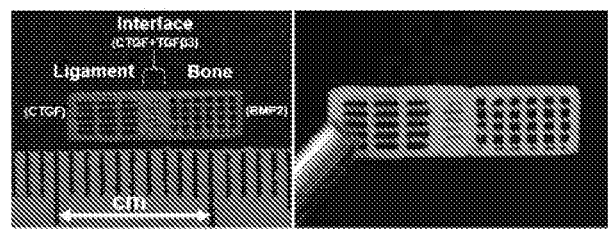

FIG. 27A is an image of a 3D printed ligament-bone scaffold. Further details regarding methodology and results are provided in Example 7.

Figure 27B:
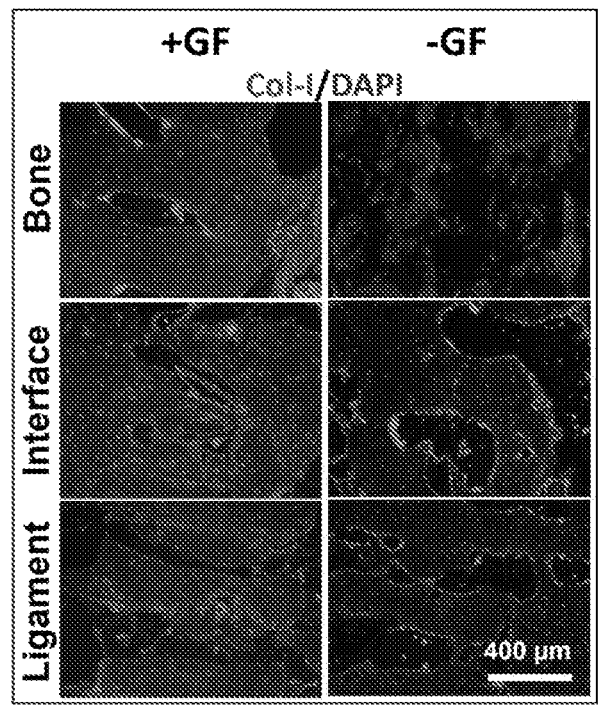

FIG. 27B is a series of fluorescence images of ligament-bone scaffold at 6 weeks. Dense collagenous tissue formed in the +GF groups.

Figure 27C:
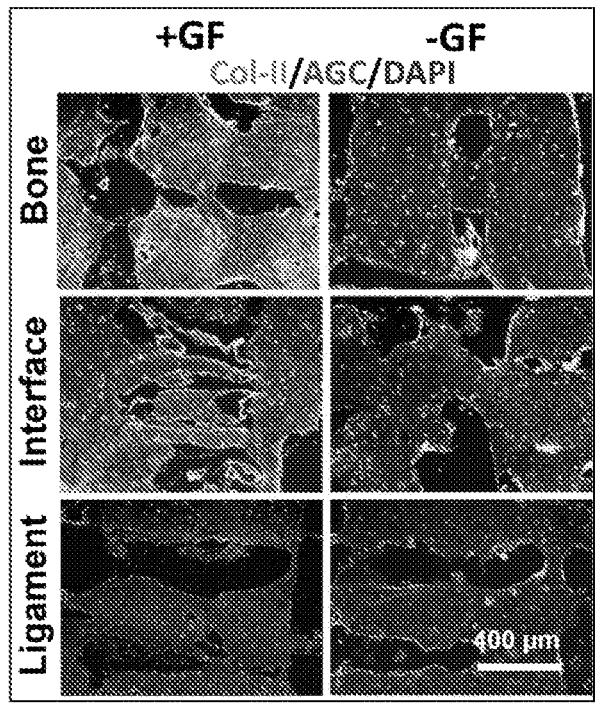

FIG. 27C is a series of fluorescence images of ligament-bone scaffold at 6 weeks. Dense collagenous tissue formed in the +GF groups.

Figure 27D:
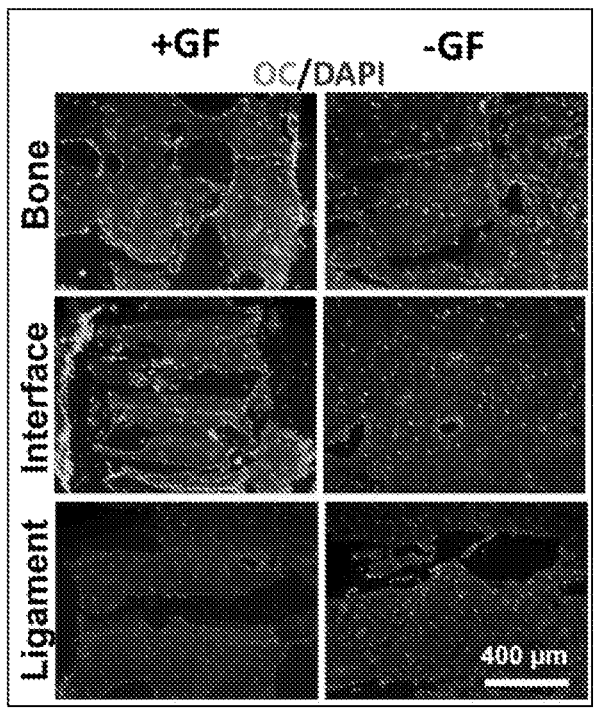

FIG. 27D is a series of images and fluorescence images of ligament-bone scaffold at 6 weeks. OC was expressed in the bone and interface regions of the +GF groups.

Figure 28A:
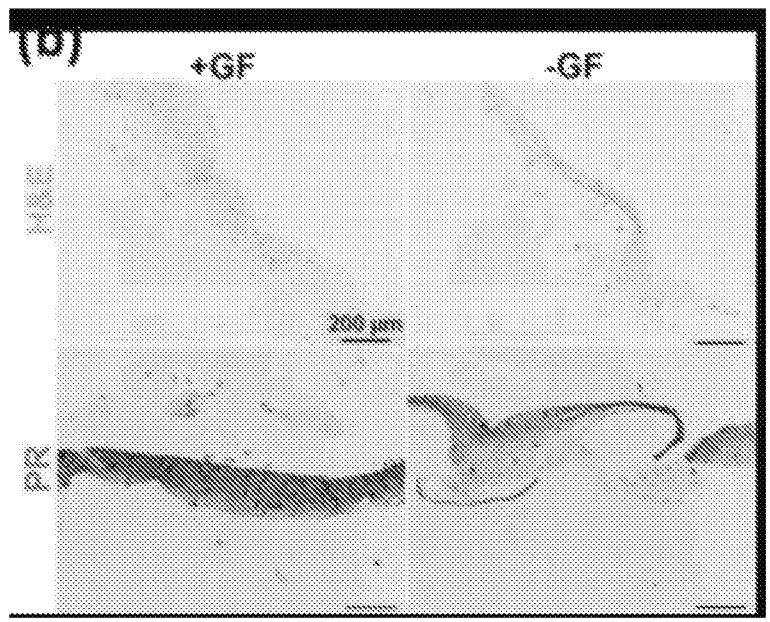

FIG. 28A is a series of images showing H&E and Picrosirius Red staining of the scaffolds after 6 weeks in vitro culture of hMSCs showing tissue formation in the scaffolds for rotator cuff repair. Further details regarding methodology and results are provided in Example 7.

Figure 28B:
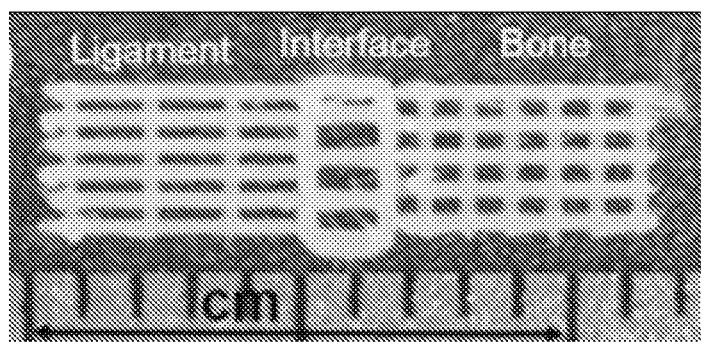

FIG. 28B is an image of a scaffold design for bone-tendon multi-tissue formation with defined interface. Further details regarding methodology and results are provided in Example 7.

Figure 28C:
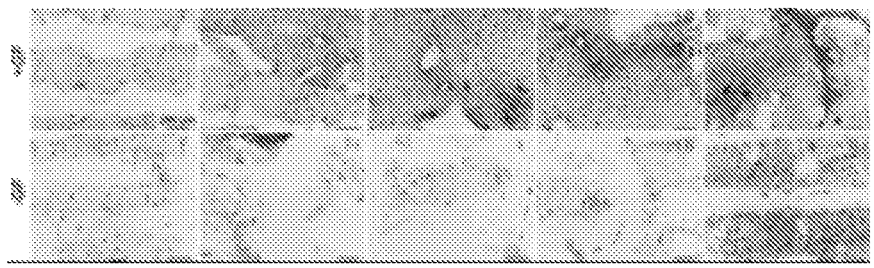

FIG. 28C is an Alizarin Red staining showing mineralized tissue formation in the bone region (having BMP2 μS). −GF group was fabricated with empty PLGA μS embedded in the PCL microstrands. Further details regarding methodology and results are provided in Example 7.

DETAILED DESCRIPTION OF THE INVENTION

The present disclosure is based, at least in part, on the discovery that microspheres encapsulating an active agent (e.g., a growth factor) can be mixed within a molten polymer (e.g., PCL) and dispensed (e.g., through a needle), creating biocompatible scaffold of micro-sized growth fibers that can provide for tissue formation or regeneration. Such biocompatible scaffold can be of an anatomical dimension and shape. A biocompatible scaffold described herein can have fully integrated microchannels, mechanical stability supporting initial loadbearing, or growth factor delivery (e.g., via microspheres) to guide regeneration by (e.g., endogenous) progenitor cells (e.g., stem cells).

It is believed that the present disclosure is the first to achieve tissue formation by micro-precise spatiotemporal delivery of multiple growth factors in an integrated 3D printed scaffold in vitro and in vivo. Furthermore, such materials and techniques can avoid use of harmful organic solvent and still provide an integrated spatiotemporal delivery with custom-designed scaffold.

Conventional scaffolds made from artificial materials do not have sufficiently high spatial and temporal resolution required for the formation of tissues with distinct boundaries or interfaces. This can make the engineering of complexes with multiple types of tissue (a common characteristic of many natural body's tissue systems) difficult or impossible.

The potential to regenerate multi-tissue complexes (e.g., within the craniofacial system) using 3D-printed multiphase scaffolds has profound clinical applications. Previous approaches of incorporating biodegradable microspheres (μS) on the surface of scaffolds can be limited by the technical difficulties of achieving even distribution of growth factors, having precise control of spatial distribution, and maintaining the scaffold's original microstructure. Approaches described herein can overcome such obstacles, providing for a 3D-printed scaffold for integrated regeneration of multi-tissue complexes in, e.g., a craniofacial system.

The present disclosure provides, inter alia, a 3D-printing method that can achieve spatial-temporal resolved delivery of growth hormones in a biocompatible scaffold in vitro and in vivo. For example, poly(lactic-co-glycolic acid) (PLGA) microspheres encapsulating an active agent (e.g., a growth factor) can be mixed within a molten polymer (e.g., PCL) and dispensed through a needle, creating micro-sized fibers containing the scaffold and growth fibers that can provide for tissue formation. Such three-dimensional scaffolds can be custom designed through the 3D-printer software or constructed through the deposition of these fibers. As described herein, the concentration of growth factors can be controlled. This ability, in conjunction with a small needle size (e.g., about 50 μm to about 400 μm), can provide a high spatial-temporal resolution to be achieved. By allowing for the precise formation of multiple tissues with distinct characteristics, methods and compositions described herein can allow for ready-to-implant grafts to guide regeneration of multi-tissue interfaces.

As shown in Example 1, methods, systems, and compositions described herein were used to improve the spatiotemporal resolution of the delivery of components of an artificial tissue so as to create multiple tissues with correct tissue interfaces. In brief, CTGF and TGFβ3 growth factors were encapsulated in microspheres (10-400 μm) of poly(lactic-co-glycolic acid) (PLGA). Other growth factors can be used, including but not limited to, CTGF, TGFβs, BMPs (e.g., bone morphogenetic growth factor 2 (BMP2)), SDF, bFGF, IGF, GDF, PDGF, VEGF, or EGF or their isoforms. The microspheres were added to the molten polycarprolactone (PCL) and dispensed via a 3D-printer through a stainless steel needle (diameter range of about 50 μm to about 400 μm), effectively creating microfibers containing both the scaffold and growth factors useful for tissue growth. 3D designs can be made or constructed by performing a layer-by-layer deposition of these microfibers. Such procedures can provide a micro-precise spatiotemporal delivery of multiple growth factors. Furthermore, by modulating the encapsulation agent, the release rate of encapsulated agents (e.g., growth factors) can be controlled. As reported in Example 1, after four weeks of culture with human mesenchymal stem cells, the PCL scaffolds with PLGA encapsulated CTGF and TGFβ3 growth factors successfully produced formation of correct multi-tissue interfaces.

The methods, materials, and resulting scaffold of Example 1 were different than conventional stereolithography or fused filament fabrication (FFF) 3D printing techniques. In conventional stereolithography 3D printing techniques, materials must be photopolymerizable and do not include commonly used materials for tissue engineering, such as PCL, PLLA, or PLGA. Also, conventional stereolithography does not allow for incorporation of multiple growth factors in a single unit of scaffolds. In conventional FFF, fibers are deposited and fused to form a bulk structure. Deposited microfibers of Example 1 followed specific patterns for each layer to form both outer shape as well as internal microchannel structures. Such porosity can be important for tissue engineering scaffolds. Furthermore, Example 1 demonstrates maintenance of a safe level of temperature in microspheres encapsulating an agent, which was confirmed by heat-diffusion analysis and stem cell culture experiment.

Multi tissue interfaces, which can be present in real tissue environments, can require precise spatial-temporal resolution of growth factors. The present disclosure can overcome the lack of spatial or temporal resolution of conventional design methods that may be unable to produce biomaterials that accurately mimic the natural tissue. Methods, systems, and compositions described herein can use 3D-printing to increase the spatiotemporal resolution of tissue design, in some embodiments using specific blends of polymers and growth factors with micron-sized needles to construct a three-dimensional scaffold. The increased resolution of this delivery system can allow for design of multi-tissue complexes with well-defined interfaces. Such technology can provide a powerful technique for the custom design of scaffolds with precise control over the composition of tissue growth factors.

As shown herein, various biomaterial-based scaffolds combined with delivery of growth factors have been tested to support regeneration of connective tissues and their interfaces. Previous scaffold designs, including stratified scaffolds with multiple phases or scaffolds with gradient growth factor/composition, have failed to recapitulate the integrated and micro-scale interfaces between multiple tissues with distinct characteristics, the pivotal features of native structures. Described herein are methods, systems, and compositions that can achieve a micro-precise spatiotemporal delivery of a growth factor(s) embedded in 3D-Printing that has potential to guide regeneration of integrated multi-tissue interfaces.

Methods, systems, and compositions described herein can provide a spatiotemporal delivery system embedded in 3D-Printed scaffolds that can serve as a ready-to-implant grafts to guide regeneration of multi-tissue complexes or interfaces. For example, the spatiotemporal delivery system can include microspheres with an encapsulated growth factor. As another example, multi-tissue complexes or interfaces can include, but are not limited to the musculoskeletal system, craniofacial system, periodontium, cementum (CM)-periodontal ligament (PDL)-alveolar bone (AB) complex, ligament/tendon-to-bone insertion, rotator cuff, supraspinatus tendon-to-bone interface (e.g., between tendon, fibrocartilage, and bone), supraspinatus tendon-fibrocartilage (unmineralized and mineralized)-bone interface, articular cartilage-to-bone junction, anterior cruciate ligament (ACL)-to-bone complex, anterior cruciate ligament-fibrocartilage-bone interface, intervertebral disc (nucleus pulposus-annulus fibrosus-endplates), cementum-periodontal ligament-alveolar bone, muscle-to-tendon, inhomogeneous or anisotropic tissues such as knee meniscus or temporomandibular joint (TMJ) disc, root-periodontium complex, tendon-bone insertion, synovial joints, or fibrocartilaginous tissues.

Methods, systems, or compositions described herein can be used for design of grafts for, inter alia, the regeneration of multi-tissue interfaces such as those found in the musculoskeletal system; grafts for inhomogeneous and anisotropic tissues such as TMJ or knee meniscus; delivery of polymer embedded alloyed materials; or dispensing conducting polymeric materials in a controlled manner.

Multi-Tissue Complex

As described herein, a biocompatible scaffold can form or regenerate a multi-tissue complex. A multi-tissue complex can include a multi-tissue interface. A multi-tissue interface can have regional variance in cell and matrix type, well-defined multi-phase tissues (e.g., ACL-to-bone complex), or inhomogeneous or anisotropic multi-phase tissues (e.g., TMJ, knee meniscus tissues). For example, multi-tissue complexes or interfaces can include, but are not limited to the musculoskeletal system; craniofacial system; periodontium, cementum (CM)-periodontal ligament (PDL)-alveolar bone (AB) complex; ligament/tendon-to-bone insertion; rotator cuff; supraspinatus tendon-to-bone interface (e.g., between tendon, fibrocartilage, or bone); supraspinatus tendon-fibrocartilage (unmineralized and mineralized)-bone interface; articular cartilage-to-bone junction; anterior cruciate ligament (ACL)-to-bone complex; anterior cruciate ligament-fibrocartilage-bone interface; intervertebral disc (nucleus pulposus-annulus fibrosus-endplates); cementum-periodontal ligament-alveolar bone; muscle-to-tendon; inhomogeneous or anisotropic tissues such as knee meniscus or temporomandibular joint (TMJ) disc; root-periodontium complex; tendon-bone insertion; synovial joints; or fibrocartilaginous tissues.

Conventionally, it was thought to be a challenge to achieve functional regeneration of multi-tissue complex with interfaces between distinct tissues, including ligament/tendon-to-bone. It is generally believed that almost all connective tissues function as an integrated unit comprised of multiple tissues with distinct cell population or mechanical properties. Until now, no reliable tool was available for successful regeneration of multi-tissue complex with integrated interface. Because many connective tissues function as an integrated unit, comprising multiple tissues with distinct cell populations and biochemical or mechanical properties, one of the challenges in functional tissue regeneration addressed by the constructs and methods disclosed herein, establishes biochemically and physically integrated multi-tissue complex or multi-tissue construct and inhomogeneous tissue with a regional variance in cell and matrix types. Methods and constructs, as described herein, can be used to regenerate such multiphase tissues.

As an example, a multiphase tissue can be a temporomandibular joint (TMJ) or knee meniscus. TMJ is a multiphase fibrocartilaginous tissue with collagen-rich peripheral bands and fibrocartilage in intermediate zone. A TMJ disc is a heterogeneous fibrocartilaginous tissue positioned between mandibular condyle and glenoid fossa of the temporal bone, with important roles in TMJ functions. Tissue engineering a TMJ disc can be an approach to overcoming limitations of current treatments for TMJ disorders. Similarly, a knee meniscus shows a gradient change from densely aligned collagenous matrix in the outer zone to the avascular cartilaginous matrix in the inner zone.

The regenerated multi-tissue complex can have mechanical properties similar to the corresponding native tissue complex. For example, mechanical properties of the regenerated tissue complex can include tensile modulus, compressive modulus, instantaneous modulus (Ei), relaxation modulus (Er), or coefficient of viscosity (μ). For example, the compressive modulus of a regenerated multi-tissue complex can be more than about 1 MPa to about 60 MPa. As another example, the tensile modulus can be at least about 10 MPa to about 70 MPa. As another example, the instantaneous modulus (Ei) can be at least about 2 MPa to about 25 MPa. As another example, the relaxation modulus (Er) can be at least about 0.5 MPa to about 20 MPa. As another example, the ratio, Er/Ei can be at least about 0.1 MPa to about 1.5 MPa. As another example, the coefficient of viscosity (μ) can be at least about 10 MPa·s to about 50 MPa·s. It is understood that recitation of the above ranges includes discrete values between each recited range.

The regenerated multi-tissue complex can have properties similar to the corresponding native tissue complex. For example, properties can include cartilage thickness, OARSI score, or GAG content. For example, the collagen content can be at least about 2 mg per g of wet scaffold to about 14 mg per g of wet scaffold. As another example, the GAG content can be at least about 0.5 μg per gram of wet scaffold to about 5 μg per gram of wet scaffold. As another example, the OARSI score can be less than 6. As another example, the collagen thickness can be at least about 0.4 mm to about 1 mm. It is understood that recitation of the above ranges includes discrete values between each recited range.

Scaffold

As described herein, a scaffold can be produced according to a three dimensional (3D) printing method such that threads or fibers of the scaffold include one or more microsphere encapsulated agents distributed through all or part of the scaffold. For example, 3D printing can refer to various additive manufacturing processes for fabricating 3D objects via layer-by-layer deposition of materials.

For example, the scaffold can be an integrated 3D printed scaffold with multiphase micro-architecture and regional distribution of a growth factor or multiple growth factors that can provide efficient biochemical/physical scaffolding environment for regeneration of multiphase tissues. For example, μS encapsulated with a growth factor or various growth factors can be incorporated in a 3D printing matrix material prior to 3D printing a scaffold.

As another example, 3D printed scaffolds, as described herein, can be custom-designed with readily tunable microstructure and porosity, and available in a wide range of compatible materials.

The 3D printing technique, as described herein, enabled construction of ready-to-implant scaffolds with native-like microfiber orientation and spatiotemporal GFs delivery, subsequently leading to multi-tissue regeneration and improved healing. For example, the in vivo findings of enhanced disc healing by 3D printed scaffolds can have a significant clinical impact in the treatment for ligament disorders, such as TMJ disorders (see e.g., Example 5).

Previous approaches provided controlled delivery of multiple growth factors in different regions in a 3D printed scaffold, leading to regeneration of integrated multiphase tissues from a single stem/progenitor cells, but incorporation of μS on the surface of microstrands suffered from limitations, including: 1) the efficiency of μS incorporation was highly dependent on microchannel structure, 2) the resolution of the manually controlled spatial μS distribution was low, and 3) the incorporated μS on the microstrands disrupted interconnectivity, surface tomography, and micropattern in scaffolds.

It is currently believed that no previous approach has reconstructed the unique anatomical shape, the heterogeneous biochemical composition/orientation, and the associated anisotropic mechanical properties of the multi-tissue interfaces as described herein (e.g., TMJ disc). Further, previous methods have been limited by low resolution in spatial control, a restricted range of applicable materials and mechanical properties, and lack spatiotemporal release control of more than one bioactive cue (see e.g., Bose, 2013; 16:496-502).

The methods and compositions described herein overcome conventional method limitations by the development of an advanced spatiotemporal delivery system embedded in 3D printed scaffolds. By embedding μS-encapsulating a growth factor or a plurality of growth factors in a polymeric microstrand constituting a 3D structure, micro-precise spatiotemporal delivery in anatomically correct 3D printed scaffolds was achieved. As described herein, the novel 3D printed scaffold embedded with a micro-precise spatiotemporal delivery system can successfully guide formation of multi-tissue interfaces from mesenchymal stem/progenitor cells (MSCs) in a resolution sufficient to recapitulate native tissue interfaces. For example, TMJ disc scaffolds, spatially embedded with connective tissue growth factor (CTGF)- and TGFβ3-μS, significantly improved healing of perforated rabbit TMJ discs with multiphase fibrocartilaginous tissues. It is noted that spatial control of embedded active agent can include the presence of the embedded agent or the absence of the embedded region, e.g., in a region, layer, or other structure of the scaffold.

Various 3D printing methods are summarized in, for example, Sawkins et al. 2013 Recent Patents on Biomedical Engineering 6, 2-13; or Li et al. 2014 International Journal of Polymer Science, Article ID 829145, 1-13. Except as otherwise noted herein, therefore, methods, systems, and compositions described herein can be carried out in accordance with, or adapted to, such processes.

A scaffold can be fabricated with any matrix material recognized as useful by the skilled artisan. Choice of scaffold material can be compatible with the 3D printing method employed. A matrix material can be a biocompatible material that generally forms a porous, microcellular scaffold, which provides a physical support for cells migrating thereto. Such matrix materials can: allow cell attachment or migration; deliver or retain cells or biochemical factors; enable diffusion of cell nutrients or expressed products; or exert certain mechanical or biological influences to modify the behavior of the cell phase. The 3D printed scaffold can be a porous, microcellular scaffold of a biocompatible material that provides a physical support or an adhesive substrate for recruitment or growth of cells during in vitro or in vivo culturing.

Suitable scaffold or matrix materials are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X. For example, matrix materials can be, at least in part, solid xenogenic (e.g., hydroxyapatite) (Kuboki et al. 1995 Connect Tissue Res 32, 219-226; Murata et al. 1998 Int J Oral Maxillofac Surg 27, 391-396), solid alloplastic (polyethylene polymers) materials (Saito and Takaoka 2003 Biomaterials 24 2287-93; Isobe et al. 1999 J Oral Maxillofac Surg 57, 695-8), or gels of autogenous (Sweeney et al. 1995.

J Neurosurg 83, 710-715), allogenic (Bax et al. 1999 Calcif Tissue Int 65, 83-89; Viljanen et al. 1997 Int J Oral Maxillofac Surg 26, 389-393), or alloplastic origin (Santos et al. 1998. J Biomed Mater Res 41, 87-94), or combinations of the above (Alpaslan et al. 1996 Br J of Oral Maxillofac Surg 34, 414-418).

Scaffold materials particularly suited to different 3D printing methods are discussed in, for example, Sawkins et al. 2013 Recent Patents on Biomedical Engineering 6, 2-13; or Li et al. 2014 International Journal of Polymer Science, Article ID 829145, 1-13.

The matrix comprising the scaffold can have an adequate porosity and an adequate pore size so as to facilitate cell recruitment and diffusion throughout the whole structure of both cells and nutrients. The matrix can be biodegradable providing for absorption of the matrix by the surrounding tissues, which can eliminate the necessity of a surgical removal. The rate at which degradation occurs can coincide as much as possible with the rate of tissue or organ formation. Thus, while cells are fabricating their own natural structure around themselves, the matrix can provide structural integrity and eventually break down, leaving the neotissue, newly formed tissue or organ which can assume the mechanical load. The matrix can be an injectable matrix in some configurations. The matrix can be delivered to a tissue using minimally invasive endoscopic procedures.

The scaffold can comprise one or more layers, each with the same or different matrix materials or the same or different microencapsulated active agents. For example, a scaffold can comprises at least two layers, at least three layers, at least four layers, or more. A multi-layer scaffold can contain one or more independently selected microsphere encapsulated growth factors in each of the layers. A multi-layer scaffold can contain one or more independently selected matrix materials in each of the layers. As another example, a scaffold can comprise a first layer comprising a first matrix material and a second layer comprising a second matrix material. As another example, a scaffold can comprise a first layer comprising microspheres encapsulating a first independently selected active agent (e.g., a growth factor) and a second layer comprising microspheres encapsulating a second independently selected active agent (e.g., a second growth factor). It is understand that multiple layers can include the same or difference matrix materials or the same or different microencapsulated active agents. As another example, a scaffold can comprise a first layer comprising microspheres encapsulating CTGF and a second layer comprising microspheres encapsulating TGFβ3.

The scaffold can comprise one or more regions, each with the same or different matrix materials or the same or different microencapsulated active agents. For example, a scaffold can comprise at least two regions, at least three regions, at least four regions, or more. Such regions can be independent, adjacent, non-adjacent, or overlapping. As another example, a scaffold can comprise a first region comprising a first matrix material and a second layer comprising a second matrix material. As another example, a scaffold can comprise a first region comprising microspheres encapsulating a first independently selected active agent (e.g., a growth factor) and a second region comprising microspheres encapsulating a second independently selected active agent (e.g., a second growth factor). As another example, a scaffold can comprise a first region comprising microspheres encapsulating CTGF and a second region comprising microspheres encapsulating TGFβ3. As described above, such regions can be partially overlapping or substantially overlapping. The one or more regions can also have the same, different, or no microencapsulated active agent in the polymeric microfibers.

The scaffold can comprise a matrix material formed of synthetic polymers suitable for the 3D printing process employed. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations or derivatives of the above. Alternatively, the matrix can be formed of naturally occurring biopolymers. Such naturally occurring biopolymers include, but are not limited to, fibrin, fibrinogen, fibronectin, collagen, or other suitable biopolymers. Also, the matrix can be formed from a mixture of naturally occurring biopolymers or synthetic polymers.

The scaffold can include one or more matrix materials including, but not limited to, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, polyacrylate, or a polyethylene oxide-polypropylene glycol block copolymer. Matrices can be produced from proteins (e.g., extracellular matrix proteins such as fibrin, collagen, fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers or other acyl substituted cellulose acetates and derivatives thereof), non-erodible polyurethanes, polystyrenes, polyvinyl chloride, polyvinyl fluoride, poly(vinylimidazole), chlorosulphonated polyolefins, polyethylene oxide, polyvinyl alcohol, Teflon®, or nylon.

In some embodiments, the scaffold can be formed from a matrix material comprising polycaprolactone (PCL). After 3D printing, the resulting polymeric microfiber can also comprises PCL.

The scaffold can further comprise any other agent or bioactive molecule, for example, an antibiotic or an additional growth factor. In some embodiments, the scaffold can be strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation. The concentration of a compound or a composition in the scaffold can vary with the nature of the compound or composition, its physiological role, or desired therapeutic or diagnostic effect. Methods, systems and compositions described herein provide for tailored concentrations of agents throughout the scaffold. Such tailored concentration of an agent can be a therapeutically effective amount. A therapeutically effective amount can be generally a sufficient concentration of therapeutic agent to display the desired effect without undue toxicity. In addition to microencapsulated agents embedded in scaffold threads or fibers as described herein, other agents can be incorporated into the scaffold or matrix material by any known method. For example, microspheres (e.g., PLGA microspheres) encapsulated with GFs can be embedded into microfibers comprised of a matrix material (e.g., PCL microfibers) in the 3D scaffold. In some embodiments, additional agents can be embedded in a gel, e.g., a collagen gel incorporated into the pores of the scaffold or matrix material or applied as a coating over a portion, a substantial portion, substantially all of, or all of the scaffold or matrix material.

Alternatively, chemical modification methods can be used to covalently link a compound or a composition to a matrix material. The surface functional groups of the matrix can be coupled with reactive functional groups of a compound or a composition to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

Channels of the scaffold can be engineered to be of various diameters. As described herein, the present disclosure provides for precise control and placement of micron sized fibers or strands. For example, the channels of the scaffold can have an inter-strand spacing diameter ranging from micrometers to millimeters. Microchannels generally have an average diameter of about 0.1 µm to about 1,000 µm, e.g., about 50 µm to about 500 µm (for example about 100 µm, 150 µm, about 200 µm, about 250 µm, about 300 µm, about 350 µm, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the matrix material(s). It is understood that recitation of the above discrete values includes ranges of values between each recited discrete value. In other embodiments, microchannels are engineered to occur in the matrix materials.

In some embodiments, the scaffold comprises pores. Pores can enhance the release profile of agents incorporated in the scaffold. Pores can be produced on the scaffold by hydrolysis (e.g., with NaOH). Pores can be an inherent property of a given matrix material.

In some embodiments, the scaffold does not comprise a transplanted mammalian cell, e.g., no cell is applied to the scaffold or any cell present in the scaffold migrated into the scaffold. A scaffold is generally understood to be a three-dimensional structure into which cells, tissue, vessels, etc., can grow, colonize, or populate when the scaffold is placed into a tissue site. A scaffold of the method can be as discussed herein.

Fabrication

Figure 2:
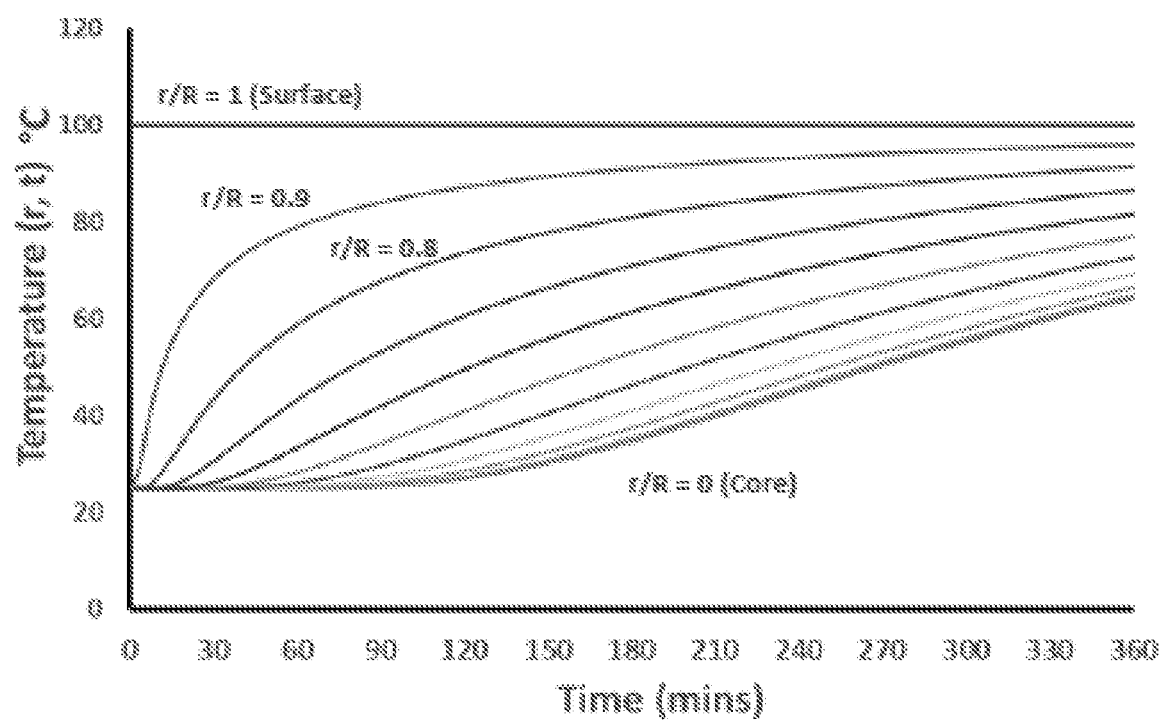
FIG. 2 is a line plot showing estimated temperature distribution within PLGA microspheres upon heating surrounding PCL from 25° C. to 100° C. The heat conduction governing equation (eq. 1) was used for the calculation. Temperature as a function of r (radial position) and t (time) is plotted from 0 to 360 minutes at 10 different depths (surface to core), where R is the radius of microspheres.

As shown herein, a matrix material (e.g., PCL) containing microsphere (e.g., PLGA microsphere) encapsulated active agent (e.g., a growth factor such as CTGF, TGFβ3, or BMP) can be heated up to 100° C. while keeping about 80% of total volume of microspheres lower than about 45° C. (see e.g., Example 1; FIG. 2). Exemplary results showed that 10 mg to 100 mg of PLGA microspheres could be controllably embedded in 1 g of PCL fibers. Ratios of PCL to PLGA µS can be optimized to yield a desired (e.g., an even) distribution of µS throughout the 3D-Printed scaffolds.

Various 3D printing methods are summarized in, for example, Sawkins et al. 2013 Recent Patents on Biomedical Engineering 6, 2-13; or Li et al. 2014 International Journal of Polymer Science, Article ID 829145, 1-13. Except as otherwise noted herein, therefore, methods, systems, and compositions described herein can be carried out in accordance with, or adapted to, such processes. Various devices for deposition of continuous microfibers are known (e.g., 3D Bioplotter® (EnvisionTec, Germany)) and can be adapted for materials and processes described herein.

Figures 1A, 1B:
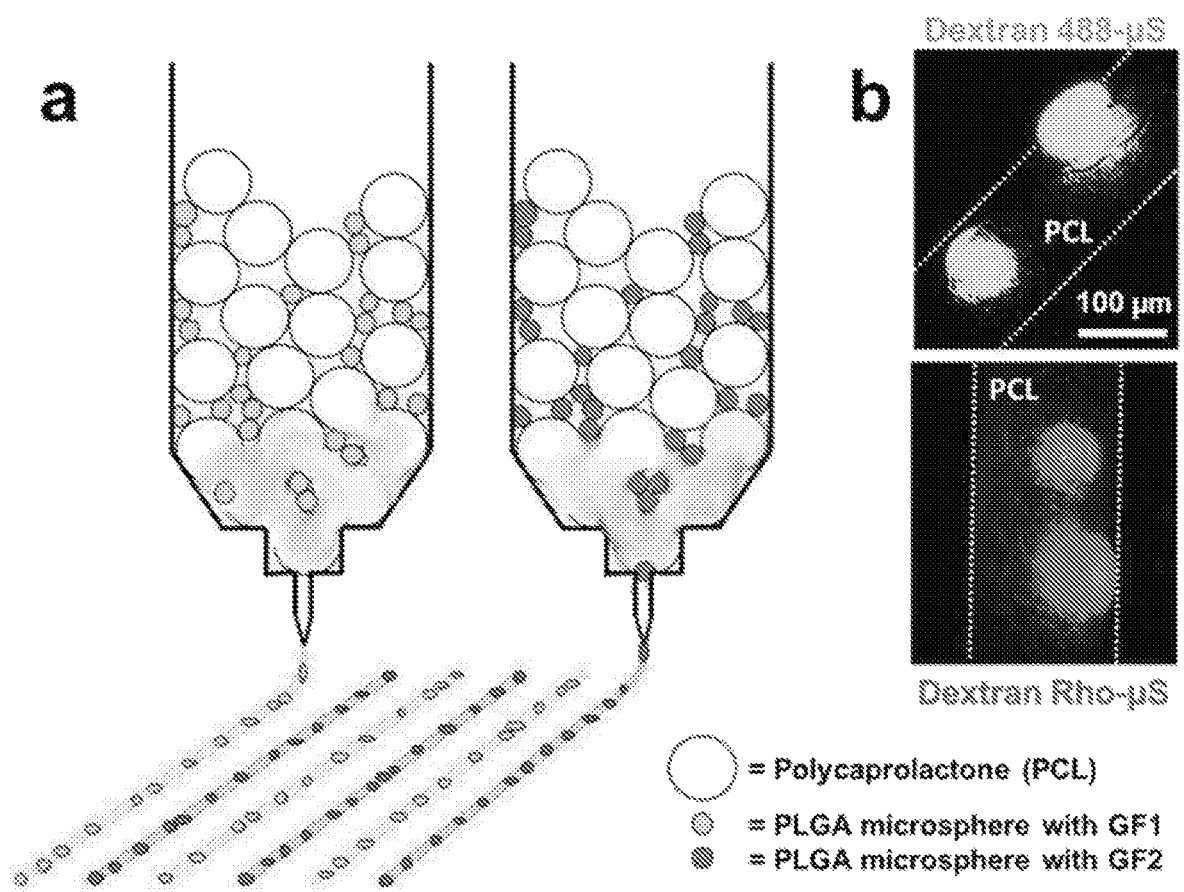

3D printing, also known as additive manufacturing (AM), can refer to various processes used to synthesize a three-dimensional object. Using a 3D printing device, successive layers of material can be formed under computer control to create an object, such as a polymeric fiber or scaffold described herein. These objects can be of almost any shape or geometry and can produced from a 3D model or other electronic data source. A 3D printing device can include a computer having a memory for storing and executing a digital file containing machine-interpretable instructions for forming a 3D scaffold described herein. A 3D printing device can include one or more cartridges for containing a matrix material or microencapsulated active agent to be dispensed (see e.g., FIG. 1A). A 3D printing device can include a heater for heating a matrix material or microencapsulated active agent to a temperature sufficient to be dispersed through the device. A 3D printing device can include a printing needle (see e.g., FIG. 1A) to dispense, e.g., from one or more cartridges, a polymeric microfiber optionally having microencapsulated active agent distributed throughout. Guiding of the printing needle can be according to a digital file containing machine-interpretable instructions for a layer-by-layer deposition of continuous microfibers from the first cartridge through the printing needle so as to form a pre-defined 3D scaffold structure. A 3D printing device can include a gantry optimized for movement in horizontal X and Y directions, with a slow climb in the Z direction as the scaffold is printed. Alternatively, a 3D printing device can use polar coordinates with radial gantry movement to print scaffolds with circular symmetry. A 3D printing device can include a chamber, which can be maintained at a pre-selected temperature (e.g., just below melting point of the matrix material) so as to provide for successful bonding of successive polymeric microfibers.

The 3D printing process can be according to fused filament fabrication, which uses a continuous filament of extruded thermoplastic material, which in view of the present disclosure can be a matrix material. This continuous filament can be fed from a large coil or from a cartridge containing matrix material or microencapsulated active agents, through a moving, heated printer extruder head. In some embodiments, one or more cartridges each contain matrix material (e.g., pellets, chips, or other small particles). In some embodiments, one or more cartridges each contain matrix material (e.g., pellets, chips, or other small particles) and microsphere encapsulated active agents. In some embodiments, (i) one or more cartridges each contain matrix material (e.g., pellets, chips, or other small particles) or (ii) one or more other cartridges each contain matrix material (e.g., pellets, chips, or other small particles) and microsphere encapsulated active agents. The cartridge can contain a heating element and the cartridge contents can be fluidically connected to the extruding nozzle or needle. Molten material, at a temperature at which the matrix material is workable but the encapsulation material does not exceed its melting point, can be forced out of a print head's nozzle or needle and can deposited on the growing scaffold. One or more cartridges can be switched during scaffold deposition to provide for, e.g., changes in matrix material, microencapsulated active agent (including different types or presence or absence), or for temperature regulation (e.g., maintaining microencapsulated active agent at our below a threshold temperature as described further herein). The deposition head (e.g., nozzle or needle) can be moved, under computer control, to define the printed scaffold shape. In some embodiments, the head moves in layers, moving in two dimensions to deposit one horizontal plane at a time, before moving slightly upwards to begin a new slice. The speed of the extruder head can also be controlled, to stop and start deposition and form an interrupted plane without stringing or dribbling between sections, regions, or layers.

The disclosure herein can provide for forming a polymeric fiber having a microencapsulated agent distributed in the polymeric fiber. At least one agent can be encapsulated in a plurality of microspheres. The microencapsulated agent can be combined with a matrix materials compatible with a 3D printing device. The matrix material and microencapsulated agent can be (separately or as a preformed combination) introduced into a first cartridge of a 3D printing device. The matrix material and microencapsulated agent can be heated to a temperature sufficient to allow dispensing of the combination of microspheres and matrix material. This temperature will depend at least in part on the choice of matrix material, the melting point of the microsphere material, or the temperature sensitivity of the active agent. The matrix material and microencapsulated agent can be heated to a temperature sufficient to allow dispensing of the combination of microspheres and matrix material while preventing substantial degradation of the microsphere or the agent encapsulated in the microsphere. The heated combination of matrix material and microencapsulated active agent can be dispensed from the first cartridge, e.g., through a printing needle, to form a fiber, e.g., a polymeric microfiber. Such a polymeric microfiber can have microencapsulated active agent distributed throughout by virtue of being co-dispensed with the matrix material.

The disclosure herein can provide for forming a biocompatible scaffold composed of polymeric fibers having a microencapsulated agent distributed in the polymeric fiber. At least one agent can be encapsulated in a plurality of microspheres. The microencapsulated agent can be combined with a matrix materials compatible with a 3D printing device. The matrix material and microencapsulated agent can be (separately or as a preformed combination) introduced into a first cartridge of a 3D printing device. For example, matrix material pellets (e.g., PCL pellets) and growth factor-encapsulated microspheres can be mixed in a dispensing cartilages of a 3D printing device. The matrix material and microencapsulated agent can be heated to a temperature sufficient to allow dispensing of the combination of microspheres and matrix material. This temperature will depend at least in part on the choice of matrix material, the melting point of the microsphere material, or the temperature sensitivity of the active agent. The matrix material and microencapsulated agent can be heated to a temperature sufficient to allow dispensing of the combination of microspheres and matrix material while preventing substantial degradation of the microsphere or the agent encapsulated in the microsphere. The heated combination of matrix material and microencapsulated active agent can be dispensed from the first cartridge, e.g., through a printing needle, to form a fiber, e.g., a polymeric microfiber. Such a polymeric microfiber can have microencapsulated active agent distributed throughout by virtue of being co-dispensed with the matrix material. A 3D scaffold can be formed by guiding the printing needle to dispense an array of polymeric microfibers having microencapsulated active agent distributed throughout. Guiding of the printing needle can be according to a digital file containing machine-interpretable instructions for a layer-by-layer deposition of continuous microfibers from the first cartridge through the printing needle so as to form a pre-defined 3D scaffold structure.

A 3D printing device can include one or more cartridges for containing a matrix material, microencapsulated active agent, or various combinations thereof. A 3D printing device can include one or more cartridges active concurrently or sequentially. A 3D printing device can include a plurality of cartridges active concurrently or sequentially. A 3D printing device can include a first plurality of cartridges and a second plurality of cartridges active concurrently or sequentially. For example, formation of a 3D printed scaffold described herein can include a plurality of cartridges, each containing independently selected matrix material, microencapsulated active agent, or various combinations thereof. For example, formation of a 3D printed scaffold described herein can include 1, 2, 3, 4, 5 6, 7, 8, 9, 10, or more cartridges, each containing independently selected matrix material, microencapsulated active agent, or various combinations thereof. Multiple cartridges can share or have independent elements such as a heating element or printing needle. For example, multiple cartridges can each contain an independent heating element (e.g., having same or different temperature or melting profiles) or printing needle (e.g., having same or different inner diameter). A 3D printing device can switch cartridges before, during or after polymeric microfiber formation or scaffold formation. For example, printing cartridges containing the same or different matrix materials or microencapsulated active agents or printing needle size can be switched during fabrication of a polymeric microfibril or during fabrication of a layer, region, or other structure of the scaffold so as to provide, e.g., differing spatial compositions of matrix and active agent. As another example, printing cartridges containing the same or different matrix materials or microencapsulated active agents or printing needle size can be switched to control temperature of the microencapsulated active agents, e.g., to maintain the microencapsulated active agents below a threshold temperature (as further described herein).

In some embodiments, the melting point of the encapsulation material is higher than the melting point of the matrix material. For example, the melting point of PLGA is over 200° C., while matrix materials can be selected having lower melting temperatures (e.g., PCL Tm ~100° C.; poly(butylene succinate) (PBS) Tm ~90-120° C.; Poly(ethylene oxide) (PEO) Tm ~65° C.; Poly(hydroxybutyrate-co-hydroxyvalerate) (PHBV) Tm ~108° C.). By ensuring the melting point of encapsulation material is higher (e.g., substantially higher) than the melting point of a matrix material, such microspheres can maintain their original structure during the dispensing process (see e.g., FIG. 1B).

In some embodiments, the matrix material is heated such that the majority of the total volume of microspheres does not exceed a pre-determined threshold of temperature or time such that the active agent is damaged or destroyed. Where an active agent includes a protein (e.g., a protein growth factor), such protein will generally denature when exposed to temperatures over about 65° C. for longer than 30 minutes. As shown herein, a PCL matrix material containing PLGA microsphere encapsulated active agent (e.g., a growth factor such as CTGF, TGFβ3, or BMP) could be heated up to 100° C. for 30 minutes while keeping about 80% of total volume of microspheres lower than about 45° C., thus protecting the encapsulated agent.

In some embodiments, the matrix material is heated to about its melting temperature for a time no longer than would result in the equivalent of about 80% of total volume of microspheres reaching 65° C. for more than 30 minutes.

FIG. 2 shows a temperature of % total volume of PLGA microspheres versus time at 100° C. PCL melting temperature. It is understood that the actual data of FIG. 2 is exemplary and the relationship of % total volume, threshold temperature of microspheres, and time can be adapted to other combinations of matrix materials and encapsulation materials.

For example, the matrix material can be heated according to the temperature and time profile of FIG. 2 for the r/R=0.9 such that 90% of total volume of microspheres do not reach more than 65° C. for more than 30 minutes. As another example, the matrix material can be heated according to the temperature and time profile of FIG. 2 for the r/R=0.8 such that 80% of total volume of microspheres do not reach more than 65° C. for more than 30 minutes. As another example, the matrix material can be heated according to the temperature and time profile of FIG. 2 for the r/R=0.7 such that 70% of total volume of microspheres do not reach more than 65° C. for more than 30 minutes. As another example, the matrix material can be heated according to the temperature and time profile of FIG. 2 for the r/R=0.6 such that 60% of total volume of microspheres do not reach more than 65° C. for more than 30 minutes. As another example, the matrix material can be heated according to the temperature and time profile of FIG. 2 for the r/R=0.5 such that 50% of total volume of microspheres do not reach more than 65° C. for more than 30 minutes. As another example, the matrix material can be heated according to the temperature and time profile of FIG. 2 for the r/R=0.4 such that 40% of total volume of microspheres do not reach more than 65° C. for more than 30 minutes.

As another example, the matrix material can be heated according to the temperature and time profile of FIG. 2 for the r/R=0.3 such that 30% of total volume of microspheres do not reach more than 65° C. for more than 30 minutes. As another example, the matrix material can be heated according to the temperature and time profile of FIG. 2 for the r/R=0.2 such that 20% of total volume of microspheres do not reach more than 65° C. for more than 30 minutes. As another example, the matrix material can be heated according to the temperature and time profile of FIG. 2 for the r/R=0.1 such that 10% of total volume of microspheres do not reach more than 65° C. for more than 30 minutes. It is understood that the matrix material can be heated for longer periods of time where the melting temperature is lower. It is understood that the actual data of FIG. 2 is exemplary and the relationship of % total volume, threshold temperature of microspheres, and time can be adapted to other matrix materials and encapsulation materials.

For example, the matrix material can be heated according to the temperature and time profile of FIG. 2 for the r/R=0.9 such that 90% of total volume of microspheres do not reach more than 60° C. for more than 30 minutes. As another example, the matrix material can be heated according to the temperature and time profile of FIG. 2 for the r/R=0.8 such that 80% of total volume of microspheres do not reach more than 60° C. for more than 30 minutes. As another example, the matrix material can be heated according to the temperature and time profile of FIG. 2 for the r/R=0.7 such that 70% of total volume of microspheres do not reach more than 60° C. for more than 30 minutes. As another example, the matrix material can be heated according to the temperature and time profile of FIG. 2 for the r/R=0.6 such that 60% of total volume of microspheres do not reach more than 60° C. for more than 30 minutes. As another example, the matrix material can be heated according to the temperature and time profile of FIG. 2 for the r/R=0.5 such that 50% of total volume of microspheres do not reach more than 60° C. for more than 30 minutes. As another example, the matrix material can be heated according to the temperature and time profile of FIG. 2 for the r/R=0.4 such that 40% of total volume of microspheres do not reach more than 60° C. for more than 30 minutes.

As another example, the matrix material can be heated according to the temperature and time profile of FIG. 2 for the r/R=0.3 such that 30% of total volume of microspheres do not reach more than 60° C. for more than 30 minutes. As another example, the matrix material can be heated according to the temperature and time profile of FIG. 2 for the r/R=0.2 such that 20% of total volume of microspheres do not reach more than 60° C. for more than 30 minutes. As another example, the matrix material can be heated according to the temperature and time profile of FIG. 2 for the r/R=0.1 such that 10% of total volume of microspheres do not reach more than 60° C. for more than 30 minutes. It is understood that the matrix material can be heated for longer periods of time where the melting temperature is lower.

For example, the matrix material can be heated according to the temperature and time profile of FIG. 2 for the r/R=0.9 such that 90% of total volume of microspheres do not reach more than 55° C. for more than 30 minutes. As another example, the matrix material can be heated according to the temperature and time profile of FIG. 2 for the r/R=0.8 such that 80% of total volume of microspheres do not reach more than 55° C. for more than 30 minutes. As another example, the matrix material can be heated according to the temperature and time profile of FIG. 2 for the r/R=0.7 such that 70% of total volume of microspheres do not reach more than 55° C. for more than 30 minutes. As another example, the matrix material can be heated according to the temperature and time profile of FIG. 2 for the r/R=0.6 such that 60% of total volume of microspheres do not reach more than 55° C. for more than 30 minutes. As another example, the matrix material can be heated according to the temperature and time profile of FIG. 2 for the r/R=0.5 such that 50% of total volume of microspheres do not reach more than 55° C. for more than 30 minutes. As another example, the matrix material can be heated according to the temperature and time profile of FIG. 2 for the r/R=0.4 such that 40% of total volume of microspheres do not reach more than 55° C. for more than 30 minutes. As another example, the matrix material can be heated according to the temperature and time profile of FIG. 2 for the r/R=0.3 such that 30% of total volume of microspheres do not reach more than 55° C. for more than 30 minutes. As another example, the matrix material can be heated according to the temperature and time profile of FIG. 2 for the r/R=0.2 such that 20% of total volume of microspheres do not reach more than 55° C. for more than 30 minutes. As another example, the matrix material can be heated according to the temperature and time profile of FIG. 2 for the r/R=0.1 such that 10% of total volume of microspheres do not reach more than 55° C. for more than 30 minutes. It is understood that the matrix material can be heated for longer periods of time where the melting temperature is lower.

For example, the matrix material can be heated according to the temperature and time profile of FIG. 2 for the r/R=0.9 such that 90% of total volume of microspheres do not reach more than 50° C. for more than 30 minutes. As another example, the matrix material can be heated according to the temperature and time profile of FIG. 2 for the r/R=0.8 such that 80% of total volume of microspheres do not reach more than 50° C. for more than 30 minutes. As another example, the matrix material can be heated according to the temperature and time profile of FIG. 2 for the r/R=0.7 such that 70% of total volume of microspheres do not reach more than 50° C. for more than 30 minutes. As another example, the matrix material can be heated according to the temperature and time profile of FIG. 2 for the r/R=0.6 such that 60% of total volume of microspheres do not reach more than 50° C. for more than 30 minutes. As another example, the matrix material can be heated according to the temperature and time profile of FIG. 2 for the r/R=0.5 such that 50% of total volume of microspheres do not reach more than 50° C. for more than 30 minutes. As another example, the matrix material can be heated according to the temperature and time profile of FIG. 2 for the r/R=0.4 such that 40% of total volume of microspheres do not reach more than 50° C. for more than 30 minutes. As another example, the matrix material can be heated according to the temperature and time profile of FIG. 2 for the r/R=0.3 such that 30% of total volume of microspheres do not reach more than 50° C. for more than 30 minutes. As another example, the matrix material can be heated according to the temperature and time profile of FIG. 2 for the r/R=0.2 such that 20% of total volume of microspheres do not reach more than 50° C. for more than 30 minutes.

As another example, the matrix material can be heated according to the temperature and time profile of FIG. 2 for the r/R=0.1 such that 10% of total volume of microspheres do not reach more than 50° C. for more than 30 minutes. It is understood that the matrix material can be heated for longer periods of time where the melting temperature is lower.

For example, the matrix material can be heated according to the temperature and time profile of FIG. 2 for the r/R=0.9 such that 90% of total volume of microspheres do not reach more than 45° C. for more than 30 minutes. As another example, the matrix material can be heated according to the temperature and time profile of FIG. 2 for the r/R=0.8 such that 80% of total volume of microspheres do not reach more than 45° C. for more than 30 minutes. As another example, the matrix material can be heated according to the temperature and time profile of FIG. 2 for the r/R=0.7 such that 70% of total volume of microspheres do not reach more than 45° C. for more than 30 minutes. As another example, the matrix material can be heated according to the temperature and time profile of FIG. 2 for the r/R=0.6 such that 60% of total volume of microspheres do not reach more than 45° C. for more than 30 minutes. As another example, the matrix material can be heated according to the temperature and time profile of FIG. 2 for the r/R=0.5 such that 50% of total volume of microspheres do not reach more than 45° C. for more than 30 minutes. As another example, the matrix material can be heated according to the temperature and time profile of FIG. 2 for the r/R=0.4 such that 40% of total volume of microspheres do not reach more than 45° C. for more than 30 minutes. As another example, the matrix material can be heated according to the temperature and time profile of FIG. 2 for the r/R=0.3 such that 30% of total volume of microspheres do not reach more than 45° C. for more than 30 minutes. As another example, the matrix material can be heated according to the temperature and time profile of FIG. 2 for the r/R=0.2 such that 20% of total volume of microspheres do not reach more than 45° C. for more than 30 minutes. As another example, the matrix material can be heated according to the temperature and time profile of FIG. 2 for the r/R=0.1 such that 10% of total volume of microspheres do not reach more than 45° C. for more than 30 minutes. It is understood that the matrix material can be heated for longer periods of time where the melting temperature is lower.

For example, the matrix material can be heated according to the temperature and time profile of FIG. 2 for the r/R=0.9 such that 90% of total volume of microspheres do not reach more than 40° C. for more than 30 minutes. As another example, the matrix material can be heated according to the temperature and time profile of FIG. 2 for the r/R=0.8 such that 80% of total volume of microspheres do not reach more than 40° C. for more than 30 minutes. As another example, the matrix material can be heated according to the temperature and time profile of FIG. 2 for the r/R=0.7 such that 70% of total volume of microspheres do not reach more than 40° C. for more than 30 minutes. As another example, the matrix material can be heated according to the temperature and time profile of FIG. 2 for the r/R=0.6 such that 60% of total volume of microspheres do not reach more than 40° C. for more than 30 minutes. As another example, the matrix material can be heated according to the temperature and time profile of FIG. 2 for the r/R=0.5 such that 50% of total volume of microspheres do not reach more than 40° C. for more than 30 minutes. As another example, the matrix material can be heated according to the temperature and time profile of FIG. 2 for the r/R=0.4 such that 40% of total volume of microspheres do not reach more than 40° C. for more than 30 minutes. As another example, the matrix material can be heated according to the temperature and time profile of FIG. 2 for the r/R=0.3 such that 30% of total volume of microspheres do not reach more than 40° C. for more than 30 minutes. As another example, the matrix material can be heated according to the temperature and time profile of FIG. 2 for the r/R=0.2 such that 20% of total volume of microspheres do not reach more than 40° C. for more than 30 minutes. As another example, the matrix material can be heated according to the temperature and time profile of FIG. 2 for the r/R=0.1 such that 10% of total volume of microspheres do not reach more than 40° C. for more than 30 minutes. It is understood that the matrix material can be heated for longer periods of time where the melting temperature is lower.

As another example, the matrix material can be heated to about its melting temperature such that 90%, 80%, 70%, 60%, 50%, 40%, 30%, 20%, or 10% of the total volume of microspheres do not reach more than 60° C. for more than about 10-40 minutes (e.g., 30 minutes). As another example, the matrix material can be heated to about its melting temperature such that 90%, 80%, 70%, 60%, 50%, 40%, 30%, 20%, or 10% of the total volume of microspheres do not reach more than 55° C. for more than about 10-40 minutes (e.g., 30 minutes). As another example, the matrix material can be heated to about its melting temperature such that 90%, 80%, 70%, 60%, 50%, 40%, 30%, 20%, or 10% of the total volume of microspheres do not reach more than 50° C. for more than about 10-40 minutes (e.g., 30 minutes). As another example, the matrix material can be heated to about its melting temperature such that 90%, 80%, 70%, 60%, 50%, 40%, 30%, 20%, or 10% of the total volume of microspheres do not reach more than 45° C. for more than about 10-40 minutes (e.g., 30 minutes). As another example, the matrix material can be heated to about its melting temperature such that 90%, 80%, 70%, 60%, 50%, 40%, 30%, 20%, or 10% of the total volume of microspheres do not reach more than 40° C. for more than about 10-40 minutes (e.g., 30 minutes). It is understood that recitation of the above discrete values (e.g., % total volume) includes ranges between each value. It is understood that recitation of the above ranges (e.g., time) includes discrete values between each range.

Dispensing temperature can be a function on the choice of matrix material and microsphere material. In some embodiments, dispensing temperature is about the melting temperature of the matrix material. For example, a matrix material including PCL can be dispensed at about 100-110° C. As another example, a matrix material including PBS can be dispensed at about 90-120° C. As another example, a matrix material including PEO can be dispensed at about 65-75° C. As another example, a matrix material including PHBV can be dispensed at about 105-110° C. These exemplified matrix material dispensing temperatures can be below, e.g., the 200° C. melting temperature of PLGA microspheres or the 120-130° C. melting temperature of higher molecular weight polyethylene microspheres. It is understood that the present disclosure can be adapted according to the melting point of the chosen microsphere material.

Dispensing time can be a function on the choice of matrix material and microsphere material. In general, the longer a matrix material containing a microsphere encapsulated active agent is dispensed, the higher the temperature the total volume of microspheres can reach.

In some embodiments, the matrix material containing a microsphere encapsulated active agent is heated and dispensed within about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, or about 60 minutes, or more. It is understood that recitation of the above discrete values includes ranges between each value. For example, the matrix material containing a microsphere encapsulated active agent can be heated and dispensed within about 10 minutes to about 45 minutes. As another example, the matrix material containing a microsphere encapsulated active agent can be heated and dispensed within about 15 minutes to about 40 minutes. As another example, the matrix material containing a microsphere encapsulated active agent can be heated and dispensed within about 20 minutes to about 35 minutes. As another example, the matrix material containing a microsphere encapsulated active agent can be heated and dispensed within about 30 minutes. Where relatively loner periods of time are desired or necessary (e.g., greater than 30 minutes) to print a scaffold, multiple printing cartridges can be used so as to avoid excessive heating of one batch combination of matrix material and microencapsulated active agent.

A printing needle of a 3D printing device can be any suitable material (e.g., stainless steel) have a defined inner diameter (e.g., 50 μm to 400 μm). As described herein, inner diameter of the printing nozzle or needle is generally larger than the mean diameter of a polymeric microsphere encapsulating an active agent so as to allow unimpeded, relatively unimpeded, or substantially unimpeded flow of unmelted or undamaged microencapsulated active agent with the molten matrix material. In some embodiments, the inner diameter of the printing needle is larger than the mean diameter of the microspheres (e.g., about 10%, about 20%, about 30%, about 40%, about 50%, about 60%, about 70%, about 80%, about 90%, about 100%, about 150%, about 200%, about 250%, about 300%, about 350%, about 400%, about 450%, about 500%, or more. It is understood that recitation of the above discrete values includes ranges between each value).

The inner diameter of the needle can be selected so as to create micro-sized growth factor/microsphere-embedded fibers of desired thickness. For example, a printing needle can have an inner diameter of about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, or about 500 μm. It is understood that recitation of the above discrete values includes ranges between each value.

Agent

As described herein, an active agent can be encapsulated in a microsphere and incorporated into a scaffold thread or fiber via a 3D printing method.

The active agent can be a growth factor. The active agent can be a growth factor selected from CTGF, TGFβs (e.g., TGFβ3), CTGF, BMPs, SDF, bFGF, IGF, GDF, PDGF, VEGF, EGF, or AM, Ang, autocrine motility factor, BDNF, EGF, EPO, FGFs, FBS, GDNF, G-CSF, GM-CSF, GDF9, HGF, HDGF, IGF, KGF, MSF, GDF-8, NGF, PDGF, TPO, TCGF, TGF-α, TGF-β, TNF-α, VEGF, PGF, Interleukins (ILs), Renalase (RNLS) or their isoforms.

Agents, such as biologic drugs that can be added to compositions and methods as described herein can include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner that enhances a particular desired therapeutic effect, for example, the cytolysis of bacterial cells or the growth of tissue- or organ-specific cells or vascularization. Biologic drugs can also be incorporated directly into the matrix component. Those of skill in the art will know, or can readily ascertain, other substances which can act as suitable non-biologic and biologic drugs.

Compositions described herein can also be modified to incorporate an agent, such as a diagnostic agent, such as a radiopaque agent. The presence of such agents can allow the physician to monitor the progression of wound healing occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents that can be utilized in the compositions can be readily ascertained by those of skill in the art and can include, for example, the use of radiolabeled fatty acids or analogs thereof.

The concentration of an agent in the composition can vary with the nature of the compound, its physiological role, or desired therapeutic or diagnostic effect. A therapeutically effective amount can be generally a sufficient concentration of therapeutic agent to display the desired effect without undue toxicity. A diagnostically effective amount can be generally a concentration of diagnostic agent which can be effective in allowing the monitoring of the integration of the tissue graft, while minimizing potential toxicity. In any event, the desired concentration in a particular instance for a particular compound can be readily ascertainable by one of skill in the art.

Encapsulation

As described herein, an active agent can be encapsulated in a microsphere (μS) and incorporated into a scaffold thread or fiber via a 3D printing method. Such microspheres are useful as slow release compositions. For example, growth factors can be micro-encapsulated to provide for enhanced stability or prolonged delivery. Encapsulation vehicles include, but are not limited to, microparticles, liposomes, microspheres, or the like, or a combination of any of the above to provide the desired release profile in varying proportions. Other methods of controlled-release delivery of agents will be known to the skilled artisan. Moreover, these and other systems can be combined or modified to optimize the integration/release of agents with the scaffold thread or fiber according to the 3D printing method. For example, the agents encapsulated in the microspheres can have a total accumulated release rate of from about 0% to about 50% over the course of at least 42 days. It is understood that recitation of the above range includes discrete values between the recited range. One skilled in the art will understand that the distribution of release rate can have any distribution including a normal distribution or a non-normal distribution.

For example, the polymeric delivery system can be a polymeric microsphere, e.g., a PLGA polymeric microspheres. A variety of polymeric delivery systems, as well as methods for encapsulating a molecule such as a growth factor, are known to the art (see e.g., Varde and Pack 2004 Expert Opin Biol Ther 4, 35-51). Polymeric microspheres can be produced using naturally occurring or synthetic polymers and are particulate systems in the size range of 0.1 to 500 μm. Polymeric microspheres can have a mean diameter of about 0.1 μm, 0.5 μm, 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, or about 500 μm, or more. As described herein the mean diameter of a polymeric microsphere encapsulating an active agent is generally smaller than the inner diameter of the printing nozzle or needle so as to allow unimpeded, relatively unimpeded, or substantially unimpeded flow of unmelted or undamaged microencapsulated active agent with the molten matrix material.

Polymeric micelles and polymeromes are polymeric delivery vehicles with similar characteristics to microspheres and can also facilitate encapsulation and matrix integration of the compounds described herein. Fabrication, encapsulation, and stabilization of microspheres for a variety of payloads are within the skill of the art (see e.g., Varde & Pack (2004) Expert Opin. Biol. 4(1) 35-51). The release rate of the microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme). Selection of an encapsulation agent can depend on the 3D printing method selected.

Progenitor Cells

As described herein, progenitor cells can be cultured with a scaffold described herein so as to form tissues comprising correct multi-tissue interfaces. Also as described, a scaffold (e.g., cellular scaffold or acellular scaffold) can be implanted in a subject so as to induce recruitment or migration of a progenitor cell.

Various compositions and methods described herein provide for implantation of a progenitor cell, recruitment of a progenitor cell, or inducing migration of a progenitor cell. A progenitor cell can be a cell that is undifferentiated or partially undifferentiated, and can divide and proliferate to produce undifferentiated or partially undifferentiated cells or can differentiate to produce at least one differentiated or specialized cell. A progenitor cell can be a pluripotent cell, which means that the cell can be capable of self-renewal and of trans-differentiation into multiple tissue types upon differentiation. Pluripotent progenitor cells include stem cells, such as embryonic stem cells and adult stem cells. A progenitor cell can be a multipotent cell. A progenitor cell can be self-renewing. For example, a progenitor cell can be a stem cell. As another example, a progenitor cell can be an adult stem cell. As another example, a progenitor cell can be a mesenchymal stem cell. As another example, a progenitor cell can be a human mesenchymal stem cell. As another example, a progenitor cell can be a bone marrow derived mesenchymal stem cell.

Progenitor cells can be isolated, purified, or cultured by a variety of means known to the art Methods for the isolation and culture of progenitor cells are discussed in, for example, Vunjak-Novakovic and Freshney (2006) Culture of Cells for Tissue Engineering, Wiley-Liss, ISBN-10 0471629359. For example, mesenchymal stem cells can be isolated from bone marrow and culture-expanded as described in U.S. patent application Ser. No. 13/877,260, published as U.S. Pat Pub No. 2014-0079739, incorporated herein by reference.

A progenitor cell can be comprised of, or derived from, an animal, including, but not limited to, mammals, reptiles, avians, horses, cows, dogs, cats, sheep, pigs, and chickens, or human.

Formulation

As described herein, an agent can be encapsulated into a microsphere and included in a scaffold thread or fiber via 3D printing. Such agent can be a formulated agent. Also described herein, a scaffold of the present disclosure can be implanted in a subject. Such scaffold can include various pharmaceutically acceptable carriers or excipients.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent can be incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a tissue defect in a subject in need of administration of a therapeutically effective amount of scaffold described herein, so as to heal, repair, improve, or prevent a tissue defect.

Treatment of a tissue defect can include regeneration, restoration, or formation of a multi-tissue complex comprising a tissue defect (e.g., musculoskeletal injury, disease, disorder, or condition). For example, treatment of a tissue defect can include functional tendon restoration by regenerating integrated tendon-bone fibrocartilaginous interfaces.

A tissue defect can comprise or be associated with a multi-tissue complex or interface. For example, a multi-tissue complex or interface can include, but is not limited to the musculoskeletal system, craniofacial system, periodontium, cementum (CM)-periodontal ligament (PDL)-alveolar bone (AB) complex, ligament/tendon-to-bone insertion, rotator cuff, supraspinatus tendon-to-bone interface (e.g., between tendon, fibrocartilage, and bone), supraspinatus tendon-fibrocartilage (unmineralized and mineralized)-bone interface, articular cartilage-to-bone junction, anterior cruciate ligament (ACL)-to-bone complex, anterior cruciate ligament-fibrocartilage-bone interface, intervertebral disc (nucleus pulposus-annulus fibrosus-endplates), cementum-periodontal ligament-alveolar bone, muscle-to-tendon, inhomogeneous or anisotropic tissues such as knee meniscus or temporomandibular joint (TMJ) disc, root-periodontium complex, tendon-bone insertion, synovial joints, or fibrocartilaginous tissues. For example, musculoskeletal injuries can be associated with tendons and/or ligaments.

As described herein, a biocompatible scaffold can overcome conventional barriers for meniscus regeneration, such as lack of fibrochondrocytes or complex bio/chemical structure and mechanics.

As an example, a subject in need can have a tissue defect of at least about 5%, about 10%, about 25%, about 50%, about 75%, about 90% or more, and compositions and methods described herein can provide an increase in number or function of tissue. As another example, a subject in need can have damage to a tissue or organ, and the method can provide an increase in biological function of the tissue or organ by at least about 5%, about 10%, about 25%, about 50%, about 75%, about 90%, about 100%, or about 200%, or even by as much as about 300%, about 400%, or about 500%. The above discrete listings of values is understood to include ranges between each of the listed values. As yet another example, the subject in need can have disease, disorder, or condition listed above, and the method provides an engineered scaffold sufficient to recruit progenitor cells and form tissue with multi-tissue interfaces sufficient to ameliorate or stabilize the disease, disorder, or condition. For example, the subject can have a disease, disorder, or condition that results in the loss, atrophy, dysfunction, or death of tissue cells. In a further example, the subject in need can have an increased risk of developing a disease, disorder, or condition that can be delayed or prevented by the method. As yet another example, the subject in need can have experienced death or dysfunction of tissue cells as the result of a side effect of a medication used for the treatment of another disease or disorder.

Methods described herein are generally performed on a subject in need thereof. A subject in need of the therapeutic methods described herein can be a subject having, diagnosed with, suspected of having, or at risk for developing tissue defect. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject. A subject can be an individual subject. A subject can be one or more subjects. A subject can be a plurality of subjects. A subject can be a subject population.

Implantation of an engineered construct is within the skill of the art. The scaffold can be either fully or partially implanted into a tissue or organ of the subject to become a functioning part thereof. The implant can initially attach to and communicate with the host through a cellular monolayer. Over time, endogenous cells can migrate into the scaffold to form tissue. The cells surrounding the engineered tissue can be attracted by biologically active materials, including biological response modifiers, such as polysaccharides, proteins, peptides, genes, antigens, or antibodies, which can be selectively incorporated into the matrix to provide the needed selectivity, for example, to tether the cell receptors to the matrix, stimulate cell migration into the matrix, or both. The scaffold or matrix material can comprise a gelled phase and interconnecting channels that allow for cell migration, augmented by both biological and physical-chemical gradients. For example, cells surrounding the implanted matrix can be attracted by biologically active materials including CTGF, BMP, or TGFβ3. One of skill in the art will recognize and know how to use other biologically active materials that are appropriate for attracting cells to the matrix.

Generally, a safe and effective amount of a scaffold of the present disclosure is, for example, that amount that would cause the desired therapeutic effect in a subject while minimizing undesired side effects. In various embodiments, an effective amount of a scaffold of the present disclosure described herein can substantially heal, repair, improve, or prevent a tissue defect.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a scaffold of the present disclosure, or components thereof (e.g., active agents) can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to heal, repair, improve, or prevent a tissue defect.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects can be the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect can be achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a scaffold can occur as a single event or over a time course of treatment. For example, a scaffold can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a tissue defect.

A scaffold can be administered simultaneously or sequentially with another agent, such as an antibiotic, an anti-inflammatory, or another agent. For example, a scaffold can be administered simultaneously with another agent, such as an antibiotic or an anti-inflammatory. Simultaneous administration can occur through administration of separate compositions, each containing one or more of a scaffold, an antibiotic, an anti-inflammatory, or another agent. Simultaneous administration can occur through administration of one composition containing two or more of a scaffold, an antibiotic, an anti-inflammatory, or another agent. A scaffold can be administered sequentially with an antibiotic, an anti-inflammatory, or another agent. For example, a scaffold can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to non-target tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a scaffold as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Green and Sambrook 2012 Molecular Cloning: A Laboratory Manual, 4th ed., Cold Spring Harbor Laboratory Press, ISBN-10: 1605500569; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein can be merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

In some embodiments the term "substantially" used in the context of describing a particular embodiment (especially in the context of certain of the following claims) can be construed as "being largely but not wholly that which is specified". Further, substantially can used to indicate that a value includes the standard deviation of the mean for the device or method being employed to determine the value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: 3D Printed Biocompatible Scaffold for Multi-Tissue Interface

The following example provides for a 3D printed biocompatible scaffold with spatiotemporal delivery of microsphere encapsulated CTGF and TGFβ3.

Selected growth factors (GF) were encapsulated in poly (lactic-co-glycolic acids) (PLGA) microspheres (μS) for controlled release. Poly(lactic-co-glycolic acid) (PLGA) microspheres (10-400 μm) encapsulating CTGF, TGFβ3, and BMP growth factors, were prepared by double-emulsion technique.

Then 3D scaffolds with custom-designed microstructure and outer shape were constructed using layer-by-layer deposition of continuous PCL microfibers. PCL pellets and growth factor-encapsulated microspheres were mixed in dispensing cartilages of 3D Bioplotter® (EnvisionTec, Germany) and heated up to 100° C., selected from heating diffusion analysis (see e.g., FIG. 1A). Material was dispensed through a fine stainless steel needle (inner diameter 50 μm to 400 μm), creating micro-sized growth factor/microsphere-embedded PCL fibers.

Given the PLGA's melting point over 200° C., microspheres were able to maintain their original structure during the dispensing process, as protecting encapsulated GFs. Fluorescent dextran/μS was used to confirm that PLGA microspheres were successfully embedded with an even distribution in the 3D-deposited PCL microstrands (see e.g., FIG. 1B). The above approach provided for fabrication of a 3D scaffolds with multiple growth factors delivered at desired location by changing dispending cartilage during the printing process, leading to fully integrated 3D custom-designed scaffold.

Results successfully demonstrated that 10 mg to 100 mg of PLGA microspheres were controllably embedded in 1 g of PCL fibers. Ratios of PCL to PLGA μS can be optimized to yield a desired (e.g., an even) distribution of μS throughout the 3D-Printed scaffolds.

Results also showed that encapsulated growth factor in microsphere-embedded PCL scaffold had sustained release over 42 days incubation in vitro (see e.g., FIG. 1E). Because the release rate can be adjusted by using different composition of PLGA, this approach enables spatiotemporal delivery of multiple growth factors.

Temperature distribution within PLGA microspheres was determined upon heating surrounding PCL from 25° C. to 100° C. The heat conduction governing equation (eq. 1) was used for the calculation. Temperature as a function of r (radial position) and t (time) is plotted from 0 to 360 minutes at 10 different depths (surface to core), where R is the radius of microspheres. As shown in FIG. 2, temperature inside the microspheres was maintained lower than 45° C. during the fabrication process when heating the PCL to 100° C. Given the average fabrication time for a scaffold (~30 mins), temperature over 80% of total volume of microspheres is lower than 45° C., which can preserve bioactivity of encapsulated growth factors. Such results are due at least in part to the extremely low heat conductivity in PLGA and its high melting point.

Moreover, bioactivity of the loaded growth factors was confirmed by stem cell differentiation as shown in FIG. 3.

The 3D printing process of this example was different than conventional fused filament fabrication (FFF) techniques. In conventional FFF, fibers are deposited and fused to form a bulk structure whereas deposited microfibers of the present Example followed specific patterns for each layer to form both outer shape as well as internal microchannel structures. Such porosity can be important for tissue engineering scaffolds.

This procedure can provide for: (a) micro-precise spatiotemporal delivery of one or more growth factors in selected locations in the 3D-Printed scaffolds; (b) controlled release rate of each growth factor by changing compositions of PLGA; or (c) region-specific microstructures in an integrated custom-designed scaffold.

Example 2: Growth Factor Delivery in 3D Printed Multi-Tissue Interface Scaffold The following Example demonstrates formation of multi-tissue interfaces in 3D-printed scaffold with spatiotemporal delivered CTGF and TGFβ3. Methods are according to Example 1 except as indicated otherwise.

A single layered rectangular structure was constructed (see e.g., FIG. 3A) with alternative PCL microfibers-embedding CTGF-μS and TGFβ3-μS (see e.g., FIG. 3B). The size of microfibers and interfibers space was 100 μm.

Then human bone marrow derived mesenchymal stem/progenitor cells (MSCs) were delivered in the scaffold's inter-fiber space via fibrin gel. After 4 weeks culture in vitro, alternative depositions of COL-I+ and COL-II+ matrices, corresponding to the pattern of growth factor delivery, forming an integrated interface within the 100-200 μm interfiber zones (see e.g., FIG. 3C).

This demonstrated PCL scaffolds with spatiotemporal delivery of CTGF and TGFβ3 successfully formed native-like micro-scale multi-tissue interfaces, evidencing the potential to regenerate multi-tissue complex such as tendon-bone insertion, synovial joints, fibrocartilaginous tissues, and periodontium.

Example 3: Spatiotemporal Delivery of Growth Factors Embedded in 3D Printed Multi-Tissue Scaffolds The following example will test the efficacy of the spatiotemporal delivery of growth factors (GFs) embedded in 3D printed scaffolds (see e.g., Example 1) for regeneration of multi-tissue complexes.

Scaffolds are first cultured with multiple stem/progenitor cell populations in vitro (see e.g., Example 5, Example 6, and Example 7), followed by in vivo implantation in a relevant animal model (see e.g., Example 5).

Scaffolds are designed with spatiotemporal delivery of growth factors. An anterior cruciate ligament-fibrocartilage-bone interfaces (see e.g., FIG. 4A) and supraspinatus tendon-fibrocartilage (unmineralized and mineralized)-bone interfaces (see e.g., FIG. 4B) are reconstructed in 3D-printed scaffolds with spatiotemporally delivered growth factors.

In a similar way, a cementum (CM)-periodontal ligament (PDL)-alveolar bone (AB) complex is reconstructed (e.g., periodontium) (see e.g., FIG. 4C). The width of each interface component, matrix type, internal microstructure (e.g. pattern, fiber size, or channel width), or delivery of relevant growth factors is applied in an integrated scaffold.

In addition to multi-tissue interfaces, the described spatiotemporal delivery system embedded in 3D-printed scaffolds is applied for recapitulating the gradient matrix distribution and organization in inhomogeneous multiphase tissues, such as TMJ disc and knee meniscus (see e.g., FIG. 4D).

Histology presented in FIG. 4 was adopted from Lu and Thomopoulos 2013 Annu Rev Biomed Eng. 15, 201-26.

Example 4: Spatiotemporal Delivery of Growth Factors Embedded in 3D Printed Rotator Cuff Scaffolds The following example will test the efficacy of the spatiotemporal delivery of growth factors (GFs) embedded in 3D printed scaffolds (see e.g., Example 1) for regeneration of multi-tissue complexes.

Scaffolds are designed with spatiotemporal delivery of growth factors. A supraspinatus tendon (i.e., rotator cuff) to-bone interface (see e.g., FIG. 6) measuring 40 mm×40-70 mm×0.5-1 mm is reconstructed in 3D-printed scaffolds with spatiotemporally delivered growth factors CTGF, CTGF+TGFβ3, and BMP2 and implanted at the tendon to bone interface for rotator cuff regeneration. Example 7 demonstrates in vitro regeneration of rotator cuff (supraspinatus tendon)-to-bone interfaces between tendon, fibrocartilage, and bone (see e.g., FIG. 20). FIG. 21 also shows immunofluorescence images of tendon-to-bone scaffold regenerating tendon-to-bone complex.

Example 5: In Vitro and In Vivo Formation of TMJ Scaffolds Mimic Native Multiphase Fibrocartilage The following example provides for a 3D printed biocompatible scaffold embedded with a spatiotemporal delivery of CTGF and TGFβ3 encapsulated in microspheres.

A micro-precise spatiotemporal delivery system embedded in 3D printed scaffolds was developed. PLGA microspheres (μS)-encapsulated with growth factors (GFs) were embedded inside PCL microfibers that constitute custom-designed 3D scaffolds. Given the substantial difference in the melting points between PLGA and PCL and their low heat conductivity, the microspheres were able to maintain its original structure while protecting the GF's bioactivities. Micro-precise spatial control of multiple GFs was achieved by interchanging dispensing cartridges during a single printing process. Spatially delivered GFs with a prolonged release guided formation of multiple tissues or micro-width multi-tissue interfaces from bone marrow derived mesenchymal stem/progenitor cells (MSCs).

To investigate efficacy of the micro-precise delivery system embedded in 3D printed scaffold, temporomandibular joint (TMJ) disc scaffolds were fabricated with micro-precise spatiotemporal delivery of CTGF and TGFβ3, mimicking native-like multiphase fibrocartilage. In vitro, TMJ disc scaffolds spatially embedded with CTGF/TGFβ3-μS resulted in formation of multiphase fibrocartilaginous tissues from MSCs. In vivo, TMJ disc perforation was performed in rabbits, followed by implantation of CTGF/TGFβ3-μS embedded scaffolds. After 4 weeks, CTGF/TGFβ3-μS embedded scaffolds significantly improved healing of the perforated TMJ disc as compared to the degenerated TMJ disc in the control group with scaffold embedded with empty μS. In addition, CTGF/TGFβ3-μS-embedded scaffolds significantly prevented arthritic changes on TMJ condyles. It was found that micro-precise spatiotemporal delivery system embedded in 3D printing can serve as an efficient tool to regenerate complex and inhomogeneous tissues.

TMJ Disc.

TMJ disc is featured by its region-dependent distribution and/or orientation of collagen fibers and cartilaginous matrix including collagen type II, proteoglycan, and glycosaminoglycan (GAGs). Collagen is the predominant extracellular matrix (ECM) in a TMJ disc, with its dense fibrous structure aligned circumferentially in the peripheral ring and predominantly aligned in anteroposterior direction in the intermediate zone (Allen and Athanasiou 2006a; Kalpakci et al. 2011; Scapino et al. 1996; Willard et al. 2012). Collagen alignment in different regions is primarily attributed to the region-dependent anisotropic tensile properties of TMJ disc (Allen and Athanasiou 2006a; Kalpakci et al. 2011; Scapino et al. 1996). GAGs, a key component of cartilage, are primarily localized in the intermediate zone and its interfaces with anterior/posterior band. Despite the low content (~5%), GAGs can be associated with the regional variance in viscoelastic properties under compression (Lumpkins and McFetridge 2009; Willard et al. 2012). Cell populations in TMJ disc can also be heterogeneous, as 70% are fibroblast-like cells throughout the tissues and 30% are chondrocyte-like cells localized in the intermediate zone (Allen and Athanasiou 2006a; Detamore et al. 2006). The heterogeneous biochemical composition/orientation and the associated anisotropic mechanical properties can be a challenge to TMJ disc regeneration.

TMJ disorders (TMJDs) affect over 10 million Americans and an annual cost for the treatment is estimated at ~$4 B, per NIDCR. TMJ disc is a biconcave fibrocartilaginous tissue positioned between mandibular condyle and glenoid fossa, and its displacement or 'internal derangement' is highly correlated with onset and progress of TMJDs. Discectomy has been often performed in patients with damaged and/or severely displaced TMJ disc to alleviate symptoms, with yet controversial experimental and clinical outcome. Synthetic or alloplastic disc replacements have also failed to reduce pain and restore joint function, frequently leading to further joint degeneration. Accordingly, the scaffolds and methods herein (e.g., TMJ disc regeneration) overcome limitations of the current treatments for ligament disorders, such as TMJ disorders.

Materials and Methods.

(i) Preparation of PLGA μS Encapsulated with GFs

Poly(d-l-lactic-co-glycolic acid) (PLGA) with a PLA/PGA ratio of 75:25 was purchased from Sigma (St. Louis, Mo.). PLGA microspheres (μS) encapsulating recombinant human bone morphogenetic protein 2 (BMP2), connective tissue growth factor (CTGF) and transforming growth factor (TGFβ3) were prepared by a modified double-emulsion technique, a well-established control-delivery vehicle demonstrating preserved bioactivity of GFs. Briefly, 500 mg PLGA was dissolved into 5 mL chloroform followed by adding 250 μL diluted growth factor (GF). This solution was then 146 emulsified (primary emulsion) by ultrasonicating for 5 minutes. The primary emulsion (w/o) was then added to 10 mL 4% (w/v) PVA (poly vinyl alcohol) solution to form the second emulsion (w/o/w) by 2 minutes ultrasonication followed by 1 minute vortexing. This double emulsion solution was then added to 250 mL of 0.3% PVA solution followed by continuous stirring for 2 hours to evaporate the solvent. Finally, the microspheres (μS) were filtered, washed with DI water, resuspended in DI water and then lyophilized. The size of PLGA μS were analyzed using SEM (ZEISS SUPRA 55VP). To confirm the embedding and distribution of μS, dextran conjugated with rhodamine A and dextran Alexa Fluor® 488 (Invitrogen, Eugene, Oreg. USA) were encapsulated in PLGA μS. For GFs encapsulated PLGA μS preparation, 500 mg PLGA was used for each of 5 μg BMP2, 2.5 μg TGFβ3, and 10 μg CTGF, respectively. DI water in the same volume was used for preparing empty μS.

(ii) Fabrication of 3D Printed Scaffolds with Spatiotemporal Delivery of Multiple GFs Scaffolds embedded with micro-precise spatiotemporal delivery system were made by layer-by-layer deposition technique using 3D Bioplotter® (4th generation; EnvisionTec, Germany). Polycaprolactone (PCL) (Polyscience Inc., Warrington, Pa., USA) powder and PLGA-µS were mixed (50 mg µS per 1 g PCL) together and filled into a high temperature cartridge. The cartridge was then heated up to 120° C. and µS-embedded PCL microfibers were dispensed through a micro-needle. Given the high melting point of PLGA over 200° C. and the low heat conductivity, the original structure of PLGA µS and the bioactivity of encapsulated GFs were maintained during the printing process, as described in the result section below. Microfibers strand diameter was controlled by the needle internal diameter (ID). Fluorescence images were taken using an Olympus IX73 microscope (Center Valley Pa., USA) and Maestro™ in-vivo fluorescence imaging system (Cambridge Research & Instrumentation, Inc. (CRi); Woburn, Mass., USA).

Cylindrical scaffolds (5 mm diameter and 5 mm height) with and without µS and single layered square shape (5×5 mm) scaffolds with GFs encapsulated µS were 3D printed for mechanical test and release kinetics, respectively. Compressive modulus and ultimate strength with or without µS were measured at a constant compression rate (1%/min) using an ElectroForce BioDynamic Testing system (Bose Corp., Eden Prairie, Minn., USA). To check if a surface treatment, creating micro/macro pores and cracks, can increase the release rate of the GF delivered in 3D printed scaffolds via µS embedding, these scaffolds were subjected to NaOH (6M) treatment for 4 hours. Morphological and/or structural changes in scaffolds after NaOH treatment were observed under SEM. The difference in release rate between untreated and NaOH treated scaffolds measured by incubating BMP2 encapsulated µS-embedded PCL scaffolds for 56 days in PBS buffer at 37° C.

(iii) MSCs Differentiation and Multi-Tissue Formation in GF/µS-Embedded PCL Scaffolds For multi-tissue formation through MSCs differentiation, scaffolds with a dimension of 5 mm×5 mm×0.5 mm were fabricated with 400 µm microstrands and 600 µm interstrand distance. CTGF, TGFβ3 and BMP2 µS (50 mg/1 g PCL) was delivered in scaffolds to stimulate fibroblastic, chondrogenic, and osteogenic differentiation, respectively. Empty µS embedded group (−GF) served as control. MSCs were isolated from human bone marrow (AllCells, Alameda, Calif.) following an established protocol. P3-5 MSCs at a density of 1×10$^6$ cells/mL were seeded into the scaffolds by infusing the cell suspended fibrin gel (20 mg/ml fibrinogen +20 U/ml thrombin) into microchannels of the scaffolds followed by 1 hour incubation at 37° C. for gel formation. Culture medium (DMEM supplemented with 10% FBS and 1% antibiotics) was added immediately after gel formation, and cultured for 4 weeks with media changes every other day. Differentiation medium was prepared. Briefly, low glucose DMEM was supplemented with 100 nM dexamethasone, 10 mM β-glycerophosphate and 0.05 mM ascorbic acid-2-phosphate for osteogenic differentiation. Ascorbic acid (50 µg/mL) was added to the low glucose DMEM to support fibrogenic differentiation. High glucose DMEM with 1% FBS was supplemented with 1% ITS+1 (Sigma) for chondrogenic differentiation. After 4 weeks culture, the cell seeded scaffolds were fixed in formalin, sectioned in 5 µm thickness, and stained with Picrosirius red (PR), Safranin O (SO), and Alizarin red (AR).

(iv) Engineering Rabbit TMJ Disc with Anatomically GF/µS-Embedded TMJ Disc Scaffolds To test the hypothesis that multi-tissue interface can be formed in a single scaffold by spatially delivered multiple growth factors, single-layered scaffolds (1.5 mm×1.5 mm) were fabricated with parallel oriented PCL microstrands (100 µm) and inter-strand spaces (100 µm), alternatingly embedding CTGF and TGFβ3 µS by changing the dispensing cartridge during the printing process. The combination of CTGF and TGFβ3 were selected given their unique role to induce fibrocartilaginous differentiation of MSCs. Then human bone marrow MSCs (1×10$^6$ cells/mL) were seeded as described previously, followed by culturing with 1:1 mixture of fibrogenic and chondrogenic supplements. After 6 weeks, harvested constructs were fixed and sectioned for histological analysis with PR, AB and immunofluorescence for collagen type I and II. Fluorescence images were taken using Maestro™ imaging system and Olympus IX73 microscope. To engineer rabbit TMJ disc, a scaffold was designed with the anatomic shape and dimension of the native TMJ disc from a 3D laser-scanned contour. Region specific internal architecture of the scaffold was designed to recreate the region-dependent collagen orientation. Briefly, PCL microstrands (200 µm) were oriented circumferentially in the anterior and posterior bands, while oriented in the anteroposterior direction in the intermediate zone with 100-200 µm of interstrand spaces. Both CTGF and TGFβ3 encapsulated µS were embedded in the microfiber strands in intermediate zone, whereas anterior and posterior zones were only embedded with CTGF encapsulated µS. Then MSCs (2×10$^6$ cells/mL) were seeded as described previously and cultured for 6 weeks with 1:1 mixture of fibrogenic and chondrogenic supplements. Fibrocartilaginous tissue formation was evaluated by histological analysis as described above.

(v) In Vivo Implantation of GF/µS-Embedded TMJ Disc Scaffolds

All the animal procedures were followed by IACUC approved protocol with skeletally mature New Zealand White rabbits (3.5-4.0 kg in body weight). Briefly, rabbits were sedated with ketamine (35 mg/ml)/xylazine (5 mg/ml) cocktail, and anesthesia was maintained by 1-5% isofluorane inhalation. Rabbits were placed in the right lateral position to expose the left TMJ on a warm-water flowing heating pad to maintain body temperature. The TMJ region, just posterior to the orbital cavities, was shaved and prepped with povidone iodine/ethanol and draped in a sterile surgical manner. The surgical site was then injected with a local anesthetic, 2% lidocaine with 1:200,000 epinephrine, to minimize discomfort. A 2-3 cm vertical incision between the posterior of the lateral orbital wall and the external acoustic meatus were performed to expose the TMJ disc followed by making a 2.5 mm punch on the disc using a sterile puncher. Pre-made sterile 3D-Printed (3DP) scaffolds in a disc shape with a dimension of 2.5×0.5 mm (diameter×thickness) were implanted using vicryl suture. These scaffolds had CTGF and TGFβ3 µS mixture consisted of 200 µm microstrands and 200-400 µm interstrand spaces. Scaffolds with empty µS served as control. Upon implantation of scaffolds, the skin was sutured continuously with non-absorbable nylon sutures. At 4 weeks post-surgery, rabbits were euthanized by IV injection of a lethal dose of euthasol (100 mg/kg). TMJ discs, condyles and glenoid fossa were harvested after 4 weeks, followed by histomorphological analyses.

(vi) Statistics

For all the quantitative data, following confirmation of normal data distribution, one-way analysis of variance (ANOVA) with post-hoc Tukey HSD tests was used with p value of 0.05. Sample sizes for all quantitative data were determined by power analysis with one-way ANOVA using an a level of 0.05, power of 0.8, and effect size of 1.50 chosen to assess matrix synthesis, gene expressions, and mechanical properties in the regenerated meniscus tissues and controls upon verification of normal data distribution.

Results.

(i) Micro-Precise Spatiotemporal Delivery of Multiple Growth Factors in 3D Printed PCL Scaffolds PCL slurry mixed with PLGA μS-encapsulated with dextran conjugated with Alexa Fluor® 488 or Rhodamine was successfully dispensed through a stainless steel microneedle (100-400 μm of inner diameter) at 120° C. (see e.g., FIG. 1A). Fluorescence microscopic images showed that PLGA μS were embedded inside PCL microstrands, as maintaining their original spherical structure (see e.g., FIG. 1B). Successful embedding of the PLGA μS in the 3D-deposited PCL microstrands were confirmed using fluorescent dextran/μS. Given the PLGA's melting point over 200° C., μS are able to maintain their original structure during the dispensing process, as protecting encapsulated GFs (see e.g., FIG. 1B). This approach enables the fabrication of 3D scaffolds with multiple growth factors delivered at desired location by changing dispending cartilage during the printing process, leading to fully integrated 3D custom-designed scaffold (see e.g., FIG. 1B). Using fluorescent dextran/μS, it was confirmed that PLGA μS were successfully embedded in the 3D-deposited PCL microstrands, with custom designed scaffold structure/pattern (see e.g., FIG. 1C). To facilitate seamless dispensing of PCL blend through micro-needles (50-400 μm in I.D.), the diameter of PLGA μS were reduced by 23±14 μm (see e.g., FIG. 7A-FIG. 7C).

By applying ultrasonication in the double emulsion technique, PLGA μS were prepared in diameters of 22.68±14.89 μm that is sufficiently small to facilitate 3D printing process (see e.g., FIG. 7A-FIG. 7C). There was no significant differences in compressive modulus and ultimate strength between PCL alone and PLGA μS-embedded PCL scaffold (50 mg per 1 g of PCL) (see e.g., FIG. 7D) (n=5 per group). NaOH (6 M) treatment for 4 hours induced micro-pores and cracks on the surface of PCL microstrands (see e.g., FIG. 7E), which led to accelerated release of encapsulated BMP-2 as compared to untreated scaffold (see e.g., FIG. 7F).

Fluorescence images of whole scaffolds from Maestro™ imaging system (PerkinElmer Inc., Waltham, Mass.) showed evenly distributed μS in 3D printed structure (see e.g., FIG. 1D, FIG. 1D).

Mechanical properties of 3D printed scaffolds, including compressive modulus and ultimate strength, were not significantly altered by embedding 50 mg PLGA μS per 1 g in PCL (see e.g., FIG. 7D). By interchanging dispensing cartridges during a printing process, μS encapsulating different dextrans were successfully embedded in desired locations in an integrated 3D PCL structure (see e.g., FIG. 1D). CTGF, TGFβ3, and BMP-2 delivered in PCL scaffolds via μS embedding showed a sustained release up to 42 days in vitro (see e.g., FIG. 1E). Detection of released GFs by ELISA further confirm the preserved biochemical structure of the delivered GFs. Surface treatment with 6 M NaOH for 4 hours resulted in micro-pores on the surface of PCL microstrands (see e.g., FIG. 7E) which in turn significantly accelerated the release rate a growth factor embedded in PCL scaffold via μS embedding in comparison with no surface treatment (see e.g., FIG. 7F).

(ii) MSC Differentiation Guided in GF/μS-Embedded Scaffolds

After 4 weeks culture with MSCs (1 M cells/ml via fibrin gel), GF/μS-embedded scaffolds guided formation of multiple types of tissues depending on the delivered growth factor (see e.g., FIG. 8A-FIG. 8L).

Bioactivity and multi-tissue formation was observed at 4 weeks culture with hMSCs (P4-5, 2 M/mL via collagen gel).

After 4 weeks culture with MSCs, Picrosirius Red (PR) staining (FIG. 8A-FIG. 8D) show dense collagenous matrix formed in CTGF μS-embedded scaffolds (see e.g., FIG. 8B) as compared to BMP-2 (see e.g., FIG. 8D), TGFβ3 (see e.g., FIG. 8C), and control groups (see e.g., FIG. 8A, FIG. 8C, and FIG. 8D).

Similarly, Safranin O (Saf O) staining (see e.g., FIG. 8E-FIG. 8H) showed cartilaginous tissue was formed in TGFβ3 μS-embedded scaffolds (see e.g., FIG. 8G), whereas Alizarin red (AR) staining (see e.g., FIG. 8I-FIG. 8L) showed mineralized matrix formed in BMP-2 μS-embedded scaffolds. For example, TGFβ3-delivered scaffolds led to formation of Saf O-positive cartilaginous matrix (see e.g., FIG. 8H), whereas BMP-2 delivery resulted in Alizarin red (AR)-positive mineralized tissues (see e.g., FIG. 8J), as compared to the control and the other growth factor groups (see e.g., FIG. 8E-FIG. 8G, FIG. 8I, FIG. 8K-FIG. 8L).

The induced differentiation of MSCs in the GF/μS-embedded scaffolds (see e.g., FIG. 8) confirms the preserved bioactivities of the delivered GFs.

(iii) Formation of Multi-Tissue Interfaces by Alternatingly Delivered CTGF and TGFβ3

Single-layered rectangular scaffolds (1.5 mm×1.5 mm) were fabricated with parallel oriented PCL microfibers (100 μm) and inter-fibers channels (100 μm) (see e.g., FIG. 9A). The PCL microfibers were alternatingly embedded with CTGF and TGFβ3 μS (see e.g., FIG. 9B). The size of microfibers and inter-fibers space was 100 μm. Human MSCs were delivered in the scaffold's inter-fiber space via fibrin gel.

After 4 weeks culture with MSCs/fibrin delivered in the inter-strands microchannels, immunofluorescence and histology revealed integrated interfaces of COL-I+ and COL-II+ matrices within the ~100 μm microchannels (see e.g., FIG. 9B, FIG. 9C, FIG. 9D, and FIG. 9E), corresponding to the alternatingly located CTGF and TGFβ3 (see e.g., FIG. 9B).

(iv) Rabbit TMJ Disc Engineering with 3D Printed Scaffolds Embedding CTGF and TGFβ3 μS PR and AB staining demonstrated the anisotropic collagen orientation and regionally variant fibrocartilaginous matrix in native rabbit TMJ discs (see e.g., FIG. 10A). Collagen was distributed throughout the TMJ disc with circumferential and anteroposterior alignment in peripheral bands and intermediate zone, respectively (see e.g., FIG. 10A). AB-positive fibrocartilaginous matrix and rounded chondrocyte-like cells were predominantly distributed in the intermediate zone and its interface with the peripheral bands (see e.g., FIG. 10A). From a 3D laser-scanned native contour data, anatomically correct rabbit TMJ disc scaffolds were fabricated with 100 μm PCL strands and inter-strands microchannels (see e.g., FIG. 10B). PCL microstrands were oriented following the region-dependent collagen alignment. CTGF μS were embedded throughout the scaffolds and TGFβ3 μS were embedded in the intermediate zone. Rhodamine μS was used to show a representative distribution of μS in the TMJ disc scaffolds (see e.g., FIG. 10B).

After 6 weeks culture with MSCs either from human bone marrow or rabbit TMJ synovium, multiphase fibrocartilaginous tissue with densely aligned fibrous matrix was observed in the anterior and posterior bands and fibrocartilaginous matrix in the intermediate zone (see e.g., FIG. 10C).

(v) Improved Healing of TMJ Disc by 3D Printed Scaffolds with Spatiotemporal Delivery of CTGF and TGFβ3

At 6 weeks in vivo, implantation of 3D printed scaffolds embedded with CTGF and TGFβ3 μS successfully improved healing of perforated rabbit TMJ disc. GF/μS-embedded scaffolds resulted in full recovery of the perforated defects with spatially distributed fibrocartilaginous matrix, reminiscent of native TMJ disc (see e.g., FIG. 11A). However, scaffolds without GF led to severe disc degeneration with structural breakdown (see e.g., FIG. 11A). High magnification histology demonstrated that the rounded chondrocyte-like cell population on the surface of native TMJ disc was successfully reconstructed in the regenerated TMJ disc with GF/μS-embedded scaffolds (see e.g., FIG. 11B). Degenerating TMJ disc without GF showed the loss of chondrocyte-like cells, replaced by spindle shaped cells within a relatively loose fibrous matrix (see e.g., FIG. 11B).

Consistently, there was no sign of cartilage defects on the articular surface of TMJ condyle, while scaffold without growth factor resulted in some vertical erosions in cartilage, as compared to native articular cartilage (see e.g., FIG. 12A-FIG. 12C). Quantitatively, the cartilage thickness with no growth factor was significantly thinner than native and the GF/μS-embedded scaffolds (see e.g., FIG. 12D). Similarly, OARSI osteoarthritis score was significantly lower with GF/μS-embedded scaffolds than scaffolds without GF (see e.g., FIG. 12E). The glenoid fossa showed a dense Saf O-positive cartilage layer when GF/μS-embedded scaffolds as compared to the native with no noticeable sign of cartilage defects (see e.g., FIG. 13A-FIG. 13C).

Discussion.

This study demonstrates an important advancement in 3D printing of tissue engineering scaffolds as a control-delivery vehicle for bioactive cues. This study showed the achievement of micro-precise delivery of multiple growth factors in different locations in a 3D printed scaffold with a sustained release over time. The novel 3D printed scaffold embedded with PLGA μS encapsulating CTGF, TGFβ3 and/or BMP-2 successfully led to formation of multiphase tissue constructs by inducing region-specific differentiation of MSCs in a native-level resolution. In addition, profibrogenic CTGF and chondrogenic TGFβ3 were successfully delivered in 3D printed anatomically correct TMJ disc scaffolds in a spatiotemporal manner, mimicking multiphase distribution of fibrocartilaginous matrix in native tissue. Upon in vivo implantation, TMJ disc scaffolds embedded with CTGF/TGFβ3-μS significantly improved healing of perforated TMJ disc in rabbits with native-like multiphase fibrocartilaginous tissue and prevented arthritic changes in the articular surfaces.

A control group with defect only, a likely representative of TMJ perforation under severe TMJ disorders is not shown. Although it is not shown in this study, the identical surgical model of 2.5 mm TMJ disc perforation without a treatment, performed by the same surgeon, showed a failure of disc healing and severe arthritis that validates the in vivo study design to investigate effects of spatiotemporally delivered GFs. Given the surgical difficulty to reconnect whole disc in rabbits, a partial graft was implanted after disc perforation. In addition, the animal model may represent or model TMJ disc perforation caused by prolonged and severe disc dislocation but osteoarthritis.

PCL degradation by hydrolysis is relatively slow. Interestingly, the in vivo implanted PCL based 3D printed scaffolds with and without GF delivery were fully degradated and replaced by newly formed tissues by 4 weeks. There are several potential explanations for the accelerated in vivo degradation, including high surface-to-volume ratio of scaffolds consisted repeats of microstrands and interstrands and the altered intrasynovial biochemical environment upon TMJ disc injury. More likely, embedding PLGA μS within PCL microfibers may increase the degradation rate. The in vitro degradation study in NaOH, PCL scaffold embedded with PLGA μS (50 mg/1 g PCL) exhibited significantly accelerated degradation in comparison with PCL alone (data not shown).

In conclusion, the novel approach to spatiotemporally deliver multiple growth factors in 3D printed scaffolds may represent an efficient tool to develop ready-to-implant bioscaffolds guiding regeneration of complex inhomogeneous tissues. The micrometer-scale resolution in spatial control of sustainably releasing GFs and the customized microstructure in 3D printed scaffolds will also be applicable for stem cell-based regeneration of inhomogeneous tissues and multi-tissue complex, including knee meniscus, tendon/ligament-to-bone interfaces, and periodontium.

Example 6: In Vitro Formation of TMJ Scaffolds

The following example provides for a 3D printed biocompatible TMJ scaffold embedded with a spatiotemporal delivery system (i.e., microspheres) encapsulating CTGF and TGFβ3 mimicking native multi-tissue complex.

This example shows the development of 3D-printed anatomically correct scaffolds with region-variant microstrands alignment, mimicking anisotropic collagen alignment in TMJ disc and corresponding mechanical properties. Connective tissue growth factor (CTGF) and transforming growth factor beta 3 (TGFβ3) were delivered in the scaffolds by spatially embedding CTGF or TGFβ3-encapsulated microspheres (μS) to reconstruct the regionally variant fibrocartilaginous matrix in native TMJ disc. When cultured with human mesenchymal stem/progenitor cells (MSCs) for 6 weeks, 3D-printed scaffolds with CTGF/TGFβ3-μS resulted in a heterogeneous fibrocartilaginous matrix with overall distribution of collagen-rich fibrous structure in the anterior/posterior (AP) bands and fibrocartilaginous matrix in the intermediate zone, reminiscent of native TMJ disc. High dose of CTGF/TGFβ3-μS (100 mg μS/g of scaffold) showed significantly more collagen II and aggrecan in the intermediate zone than a low dose (50 mg μS/g of scaffold). Similarly, high dose of CTGF/TGFβ3-μS yielded significantly higher collagen I expression in the AP bands as compared to the low dose and empty μS. From stress relaxation tests, the ratio of relaxation modulus to instantaneous modulus was significantly smaller with CTGF/TGFβ3-μS than empty μS. Similarly, a significantly higher coefficient of viscosity was achieved with the high dose of CTGF/TGFβ3-μS as compared to the low dose and empty μS, suggesting the dose-effect of CTGF and TGFβ3 on fibrocartilage formation. This example shows an efficient approach to engineering TMJ disc graft with anisotropic scaffold microstructure, heterogeneous fibrocartilaginous matrix, and region-dependent viscoelastic properties.

In this study, a 3D printing technique and spatiotemporal delivery system was developed to construct an anatomically correct TMJ disc scaffold with regionally variant microstructure and the associated mechanical properties. The scaffolds with spatiotemporal delivery of CTGF and TGFβ3 successfully induced the region-dependent fibrocartilaginous differentiation of MSCs, consequently leading to formation of heterogeneous fibrocartilage reminiscent of native TMJ disc. Dose effects of CTGF and TGFβ3 on the viscoelastic properties of the engineered TMJ disc were also investigated with an ultimate goal of developing a ready-to-implant TMJ disc biograft.

Materials and Methods.

(i) Fabrication of 3D-Printed TMJ Disc Scaffolds with Spatiotemporal Delivery of CTGF and TGFβ3

Anatomically correct TMJ disc scaffolds were fabricated with polycaprolactone (PCL) using layer-by-layer deposition technique with 3D Bioplotter® (4th generation; EnvisionTec, Germany) according to Lee et al. 2014. Briefly, the anatomical shape and dimension of TMJ disc were adopted from 3D laser-scanned contour that was reconstructed into a 3D CAD model (see e.g., FIG. 14A), followed by 3D printing scaffolds. TMJ disc scaffolds were constructed with repeating microstrands and interstrand microchannels with their orientation predominantly in the circumferential and anteroposterior directions in the peripheral ring and intermediate zone, respectively (see e.g., FIG. 14B), mimicking native anisotropic collagen alignment. The size of PCL microstrands (300 μm) and microchannels (300 μm) and the relative density of microstrands parallel to versus perpendicular to the alignment direction (2:1) were determined to closely approximate the tensile properties of those of native disc in the circumferential and anteroposterior directions, respectively (see e.g., FIG. 14C).

(ii) Spatiotemporal Delivery of CTGF and TGFβ3

Because a combination of profibrogenic CTGF and chondrogenic TGFβ3 growth factors induce fibrochondrogenic differentiation of MSCs, CTGF and TGFβ3 were spatiotemporally delivered into the 3D-printed scaffolds to guide formation of heterogeneous fibrocartilage reminiscent of native TMJ disc. For a prolonged release, CTGF and TGFβ3 were first encapsulated in 75:25 poly(lactic-co-glycolic acids) (PLGA) microspheres (μS) by double-emulsion technique, according to Lee et al. 2010b and Lee et al. 2014. A single dose of CTGF (10 μg) and TGFβ3 (5 μg) was encapsulated in 500 mg PLGA μS according to Lee et al. 2010b and Lee et al. 2014. CTGF or TGFβ3 encapsulated PLGA μS were then mixed with PCL powder (Polyscience Inc., Warrington, Pa.) (50 mg or 100 mg μS per 1 g PCL) in a high temperature dispensing cartridge of 3D-Bioplotter®. The doses of CTGF and TGFβ3 encapsulation and PLGA μS were pre-optimized. The cartridge was then heated up to 120° C. and μS-embedded PCL microfibers were dispensed through a micro-needle. Given the PLGA's high melting point over 200° C. and low heat conductivity (Qian et al. 2001), PLGA μS were embedded in PCL microstrands constructing 3D scaffolds while maintaining their original structure and preserving encapsulated growth factors (GF) (Tarafder et al. 2016). CTGF μS-embedded and CTGF & TGFβ3 μS-embedded PCL microstrands were constructed into the peripheral bands and the intermediate zone, respectively, to recapitulate the fibrous matrix in the peripheral bands and fibrocartilaginous matrix in the intermediate zone. To confirm the spatial delivery of GFs, dextran conjugated with Alexa Fluor® 488 and 546 were encapsulated in PLGA μS, followed by imaging with Maestro™ in-vivo imaging system (CRi; Woburn, Mass., USA). In vitro release kinetics of the delivered GFs were measured by ELISA up to 42 days by incubating the scaffolds in PBS or 0.1% BSA buffer at 37° C. with gentle agitation, as per Lee et al. 2010b and Lee et al. 2014.

(iii) Human TMJ Disc Engineering with MSCs

Human mesenchymal stem/progenitor cells (MSCs) were isolated from commercially available, fresh whole bone marrow samples of anonymous adult donors (AllCells, Alameda, Calif.) (age range: 20-25 years old) according to Lee et al. 2009; Lee et al. 2010b; and Lee et al. 2014. Passage 3/4 MSCs (2 M cells/mL) were seeded in the 3D-printed TMJ disc scaffolds by infusing the cell suspended neutralized collagen I solution (2 mg/mL) into the scaffold's microchannels, followed by 30 minutes incubation at 37° C. for gel formation. MSC-seeded scaffolds were then cultured for 6 weeks with 1:1 mixture of fibrochondrogenic induction supplement (FIS) (50 μg/mL ascorbic acids) and chondrogenic induction supplements (CIS) (1% 1×ITS+1 solution, 100/ml sodium pyruvate, 50 μg/ml L-ascorbic Acid 2-phosphate, 40 μg/ml L-proline, 0.1 μM dexamethasone) (Lee et al. 2014). Low and high doses (50 mg and 100 mg μS per 1 g PCL) of CTGF/TGFβ3 μS in the 3D-printed scaffolds were tested for TMJ disc engineering with MSCs. Low and high doses of empty μS were applied as controls. Harvested samples after 6 weeks were analyzed using histology with Safranin O (Saf-O) and Picrosirius red (PR) (Lee et al. 2010b; Lee et al. 2014). Total collagen and GAGs contents were measured using Biocolor assay kits (Carrickfergus, UK) following Lee et al. 2010b. Immunofluorescence was performed to evaluate collagen I and II (COL-I & II) and aggrecan (AGC) as per Lee et al. 2014. Relative areas of COL-II and AGC positive matrix in the anterior and posterior (AP) bands and intermediate zone were calculated using an imaging process following Lee et al. 2010a. Expression of COL-I mRNA was measured by qRT-PCR (Lee et al. 2010a; Lee et al. 2014) for the MSC-seeded scaffolds with low and high doses of CTGF/TGFβ3 μS and empty μS.

(iv) Mechanical Property Tests

Mechanical properties of 3D-printed scaffolds and the engineered TMJ disc were evaluated by compression, tensile, and stress relaxation tests as per Lee et al. 2010a and Lee et al. 2014 using BioDynamics® testing system (TA instruments, New Castle, Del.). For tensile tests, scaffolds were prepared in a dog bone shape with length of 25 mm and average thickness of 1 mm. After preconditioning of 15 cycles of 0-10% strain, tensile tests were performed at 1% strain/min. The linear portion of each stress-strain curve was used to determine the tensile modulus. For compression and stress relaxation tests, disc-shaped samples (5×2 mm$^2$) were prepared from the AP bands and intermediate zone of the TMJ disc constructs. Using unconfined compression, samples were preconditioned with 15 cycles of 0-10% compressive strain, followed by compression at 1% strain/min. For stress relaxation, 30% step strain was applied and held until a relaxation plateau was reached. A Kelvin standard solid viscoelastic model was applied to calculate instantaneous modulus ($E_i$), modulus of relaxation ($E_r$), and coefficient of viscosity ($\mu$) using MATLAB curve fitting tool as per Lee et al. 2014. The mechanical properties of engineered TMJ discs were compared with those of native TMJ discs (18~65 year-old) from National Disease Research Interchange (NDRI).

(v) Statistical Analysis

Upon confirmation of normal data distribution, One-way ANOVA with a post-hoc Tukey test were used to compare between the groups with p value<0.05 considered significant.

Results.

(i) Optimal microstructure of scaffolds to achieve initial tensile properties

Tensile properties of scaffolds were affected by sizes of microstrands and microchannels. Among the multiple configurations of microstructure, 300 μm PCL microstrand diameter and 300 μm microchannels with 2:1 ratio of parallel microstrands and perpendicular microstrands showed the tensile modulus of scaffolds most approximately to that of native TMJ discs (see e.g., FIG. 14C).

(ii) Spatiotemporal Delivery of CTGF and TGFβ3 in 3D-Printed TMJ Disc Scaffolds for Generation of Heterogeneous Fibrocartilage Representative fluorescence images with μS-encapsulating Alex Fluora® 488 and 546 demonstrated that CTGF is delivered throughout the scaffolds whereas CTGF and TGFβ3 are delivered in the intermediate zone of the TMJ disc scaffolds (see e.g., FIG. 14D). CTGF and TGFβ3 delivered in the scaffold showed a sustained release up to 42 days in vitro (see e.g., FIG. 14E). When cultured with MSCs (2 M/mL) for 6 weeks, scaffolds with spatiotemporal delivery of CTGF and TGFβ3 formed heterogeneous fibrocartilaginous tissues, featured by COL-I+ fibrous matrix throughout the scaffolds and COL-I+/AGC+ fibrocartilaginous matrix localized in the intermediate zone (see e.g., FIG. 14G) in comparison with empty μS (see e.g., FIG. 14F). Quantitative matrix assays demonstrated that total collagen contents per wet weight were significantly higher both in the intermediate zone (IZ) and the anterior/posterior band (AP) with GF delivery as compared to control without GF (see e.g., FIG. 14H) ($p<0.05$; $n=5$ per group). Similarly, GAGs content was significantly higher with GF delivery as compared to control (see e.g., FIG. 14I) ($p<0.05$; $n=5$ per group). IZ showed significantly higher GAGs content than AP (see e.g., FIG. 14I) ($p<0.05$; $n=5$ per group).

(iii) Dose effect of CTGF and TGFβ3-μS in TMJ disc tissue engineering After 6 weeks culture with MSCs, growth factors (GF; CTGF and TGFβ3) encapsulated μS-embedded scaffolds formed heterogeneous fibrocartilage featured by Saf-O-positive cartilaginous matrix in the intermediate zone and PR-positive denser collagenous tissue in the AP bands (see e.g., FIG. 15A). The high dose (100 mg μS/g PCL) showed likely denser cartilaginous matrix in the intermediate zone as compared to low dose (50 mg μS/g PCL) (see e.g., FIG. 15A). Higher magnification images consistently showed higher density of collagenous tissue in the AP bands and fibrocartilaginous tissue in the intermediate zone with GF/μS-embedded scaffolds, in comparison to empty μS-embedded scaffolds (see e.g., FIG. 15B). Quantitatively, total collagen content in the AP bands were significantly higher with the high dose as compared to low dose of GF/μS and empty/μS (see e.g., FIG. 15C) ($p<0.05$; $n=5$ per group). Total GAGs content in the IZ were significantly higher with the high dose as compared to the low dose of GF/μS and empty/μS (see e.g., FIG. 15D).

Immunofluorescence demonstrated that both high and low doses of GF/μS resulted in COL-II+/AGC+ fibrocartilaginous tissue in the intermediate zone, not in the AP bands (see e.g., FIG. 16A). No COL-II and AGC were found with the empty μS (see e.g., FIG. 16A). Consistently, denser COL-I+ matrix was formed with GF/μS both in high and low doses in the AP bands, in comparison with the empty μS (see e.g., FIG. 16A). Relative areas positive for COL-II and AGC were significantly wider in for the high dose as compared to the low dose (see e.g., FIG. 16B) ($p<0.05$; $n=10$ per group). qRT-PCR showed significantly more COL-I mRNA expression with the GF/μS for high and low doses as compared to empty μS (see e.g., FIG. 16C) ($p<0.05$; $n=5$ per group).

(iv) Mechanical Properties of Engineered TMJ Discs

By 6 weeks culture with MSCs, there was no statistically significant difference in the tensile modulus to the direction of PCL microstrand alignment between GF/μS and empty μS (see e.g., FIG. 17A). The compressive modulus was significantly higher in the high dose (100 mg μS/g PCL) empty μS than the low dose (50 mg μS/g PCL) both in the AP bands (see e.g., FIG. 17B) and the intermediate zone (see e.g., FIG. 17C). The high dose of GF/μS resulted in a significantly lower compressive modulus, closer to that of native tissue, as compared to empty μS (see e.g., FIG. 17B-FIG. 17C).

Instantaneous ($E_i$) and relaxation moduli ($E_r$) were significantly lower in high dose GF/μS than empty μS both in the AP bands (see e.g., FIG. 18A-FIG. 18B) and the intermediate zone (see e.g., FIG. 18E-FIG. 18F). Both $E_i$ and $E_r$ in the GF/μS groups were closer to those of native tissues as compared to the empty μS (see e.g., FIG. 18A, FIG. 18B, FIG. 18E, FIG. 18F). Similarly, the ratio of $E_r$ to $E_i$ was significantly smaller in the high dose GF/μS as compared to all the other groups, more approximating the native property (see e.g., FIG. 18C, FIG. 18G). Coefficient of viscosity ($\mu$) was significantly higher with GF/μS as compared to empty μS both in the AP bands and the intermediate zone (see e.g., FIG. 18D, FIG. 18H). Furthermore, the high dose GF/μS showed a significantly higher coefficient of viscosity ($\mu$), closer to the native level, in comparison with the low dose (see e.g., FIG. 18D, FIG. 18H).

Discussion.

This study's findings represent an efficient approach to engineering TMJ disc mimicking the anisotropic microstructure and heterogeneous fibrocartilage in native tissues. Anatomically correct TMJ scaffolds were fabricated by an advanced 3D-printing technique that enables construction of regionally variant microstructure and spatiotemporal delivery of multiple growth factors. Spatiotemporal delivery of CTGF and TGFβ3 by embedding PLGA μS in PCL microstrands successfully guided formation of native TMJ disc-like heterogeneous fibrocartilage from MSCs. As compared to the low dose, the high dose of GF/μS in the PCL scaffold further improved the quality of the engineered TMJ disc, featured by fibrocartilaginous matrices distribution in a region-dependent manner. In addition, the magnitudes of stress decrease and viscosity in a stress relaxation test were also affected by the dose of GF/μS, likely demonstrating the roles of cartilaginous matrix in the viscoelastic properties of TMJ discs, consistent with other studies (Allen and Athanasiou 2006b; Willard et al. 2012). The instantaneous modulus is determined by both elastic and viscous components, whereas the relaxation modulus is mainly dependent on elastic component in biological tissues. The coefficient of viscosity is the constant of proportionality between the stress and the strain rate. Accordingly, all the three characteristics determine the time-dependent mechanical behaviors of fibrocartilaginous tissues under dynamic loading conditions thus need to be considered key criterion to evaluate engineered TMJ discs.

The scaffolds of this study with the optimized microstructure successfully resulted in the region-variant anisotropic tensile properties. Interestingly, the tensile properties of the harvested samples at 6 weeks were not affected by growth factor delivery in either high or low doses of GF/μS. It is postulated that the aligned PCL microstrands with a higher order of tensile modulus (~300 MPa) play a dominant role in determining the tensile properties of the in vitro engineered constructs rather than newly formed ECM. In contrast, the compressive modulus was highly affected by growth factor delivery in a dose-dependent manner. After 6 weeks in vitro, MSC-seeded scaffolds with the high dose GF/μS resulted in a compressive modulus on par with the native level, which is significantly lower than that with empty μS. Given the higher order of magnitude of the compressive modulus of PLGA than of PCL, the high content of PLGA μS in PCL microstrands may have contributed to the higher compressive modulus of scaffolds. The significant change in the compressive modulus of scaffolds GF/μS-embedded scaffolds cultured with MSCs for 6 weeks is likely due to the accelerated PLGA degradation via biochemical hydrolysis associated with MSC differentiation (Pan and Ding 2012). Estimated volume fractions of PLGA μS in PCL strands from an imaging processing were 12±3.5% and 23±4.2% for low and high doses, respectively. This likely provides an explanation for the higher initial compressive and tensile moduli with higher doses of PLGA μS. Long-term and in vivo follow-up studies will facilitate in the understanding behind the mechanism of the accelerated scaffold degradation related to MSC differentiation and fibrocartilage formation.

This study is primarily focused on development of TMJ disc biograft with design parameters for human tissues.

In conclusion, this example demonstrated a novel and efficient approach to engineering TMJ disc-like construct with heterogeneous fibrocartilaginous matrix and region-dependent viscoelastic properties mimicking native tissues. This study showed 3D-printed scaffolds with spatiotemporal delivery of CTGF and TGFβ3 can serve as an efficient tool in stem cell-based regeneration of TMJ discs.

Example 7: In Vitro Regeneration of Integrated Tendon-Bone Interface and Ligament-Bone Interface This example shows the successful formation or regeneration of integrated tendon-bone interfaces and ligament-bone interfaces with fibrocartilaginous matrix gradient mimicking native multi-tissue complex.

This example shows the development of micro-precise spatiotemporal growth factor (GF) delivery system embedded in the micro-strands of the 3D printed scaffolds for integrative regeneration of multi-tissue complex. Temporally controlled release of the specific GFs from the spatially embedded μS in the micro-strands guide tissue specific differentiation of mesenchymal stem/progenitor cells.

Rotator Cuff.

A rotator cuff disorder or injury can be located in the supraspinatus tendon-fibrocartilage (unmineralized and mineralized)-bone interface. ~2M Americans visit doctors every year because of a rotator cuff injury, with over 100,000 rotator cuff repairs each year. Rotator cuff repairs failure rates can be 20% to 90% depending on the patient age, tear size and chronicity, muscle atrophy and degeneration, tendon quality, repair technique, and the postoperative rehabilitation protocol. Shoulder injuries are frequently caused by athletic activities that involve excessive, repetitive, overhead motion, such as swimming, tennis, pitching, and weightlifting. Injuries can also occur during everyday activities such washing walls, hanging curtains, and gardening. 10% of partial-thickness tears heal and 10% become smaller, but 53% of tears will propagate and 28% progress to full-thickness tears. Full-thickness rotator cuff tears do not heal spontaneously, and may progress with time (Yamanaka & Matsumoto. Clin Orthop 1994; 304:68-73) (see e.g., FIG. 19).

Methods.

Figure 1F:
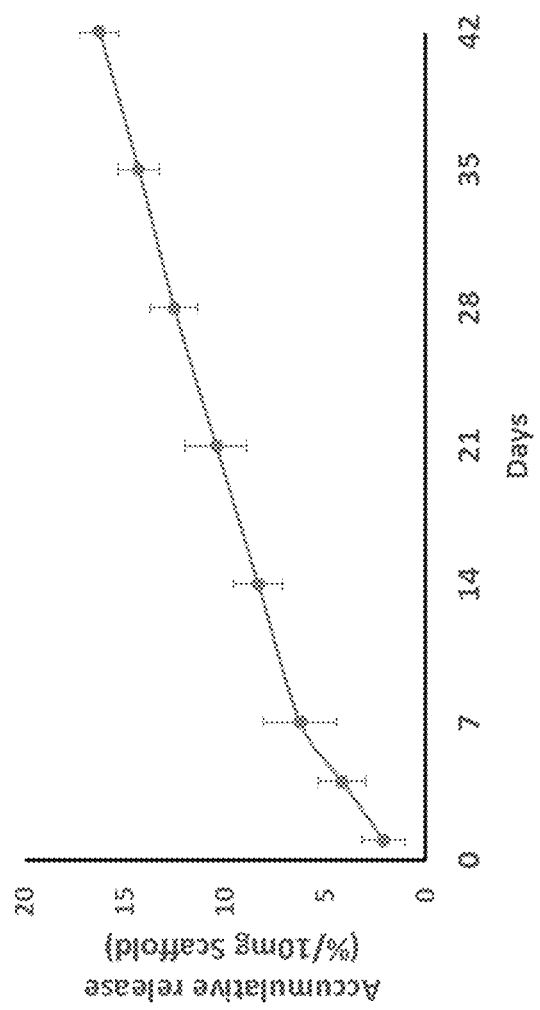
Figure 1G:
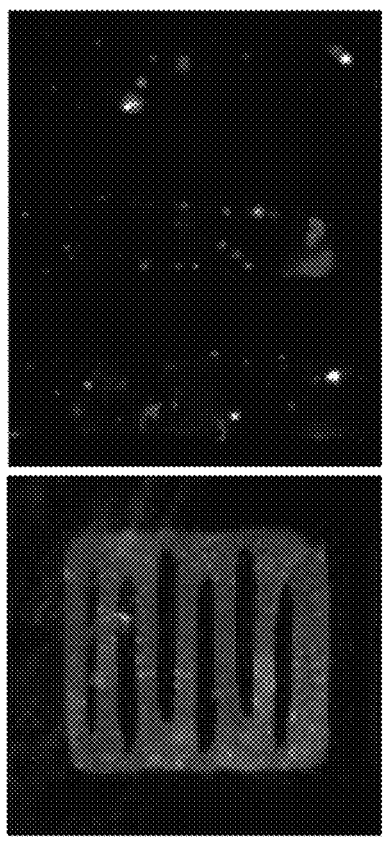
FIG. 1G is a fluorescence image of spatiotemporal delivery of multiple growth factors in 3D printed scaffolds.

(i) Construction of 3D Printed Scaffolds with Spatiotemporal Delivery of Growth Factors Multiple GFs, including connective tissue growth factor (CTGF), transforming growth factor β3 (TGFβ3) and bone morphogenetic growth factor 2 (BMP2), were first encapsulated in PLGA microspheres (μS). GF-encapsulated PLGA μS were mixed with PCL slurry heated up to 100° C. and dispensed through micro-needle to construct a 3D structure using an advanced 3D printer (Bioplotter®; EnvisionTec, Germany). Given the PLGA's melting point over 200° C. and a low heat conductivity, μS are able to maintain its original structure during the dispensing process while protecting bioactivities of encapsulated GFs (data not shown). A fully integrated 3D custom-designed scaffold with multiple GF-μS at desired location was fabricated by changing dispensing cartridge during a printing process (see e.g., FIG. 1A). Fluorescent dextran/μS was used to confirm that PLGA μS were successfully embedded in the 3D-deposited PCL micro-strands (see e.g., FIG. 1B). The delivered GFs showed a sustained release up to 42 days (see e.g., FIG. 1F).

(ii) Multi-Tissue Formation from MSCs

To confirm the bioactivities of the released GFs and its effect to guide multi-tissue interfaces, a single layered rectangular structure was constructed with alternative PCL microfibers-embedding CTGF-μS and TGFβ3-μS with inter-fiber spacing of 100 μm (see e.g., FIG. 3B). Human bone marrow derived mesenchymal stem/progenitor cells (hMSCs) (1 M/mL) were then delivered in the scaffold's inter-fiber space via fibrin gel. After 4 weeks culture, alternative depositions of COL-I+ and COL-II+ matrices were demonstrated by immunolabeling. Similarly, an integrated scaffolds were fabricated comprising of three layers: PCL/CTGF μS, PCL/CTGF+TGFβ3, and PCL/BMP2 μS, for regeneration of rotator cuff (supraspinatus tendon)-to-bone interfaces between tendon, fibrocartilage, and bone (see e.g., FIG. 20). Another scaffold with specified architecture and dimension was designed for ACL-to-bone complex formation with defined interface (see e.g., FIG. 28B). These scaffolds were seeded with hMSCs for 6 weeks and multi-tissue formation was evaluated by histological analyses.

Results.

Immunofluorescence images of tendon-bone scaffolds are shown at 6 weeks with hMSCs (2 M/mL) with and without GF (see e.g., FIG. 21). +GF group induced higher collagen I expression than the –GF group (see e.g., FIG. 21, FIG. 22A-FIG. 22C). –GF group did not show any aggrecan (AGC) expression in the ECM (see e.g., FIG. 23). Only the BMP2 layer in the +GF group showed osteocalcin (OC) expression (see e.g., FIG. 24-FIG. 25). The engineered tissue-bone interface shows integrated Col-I, Col-II, AGC, and OC expression mimicking the tendon-to-bone interface of native tissue (see e.g., FIG. 26A-FIG. 26B).

Immunofluorescence images of tendon-bone scaffolds are shown at 6 weeks with hMSCs (2 M/mL) with and without GF (see e.g., FIG. 27A-FIG. 27D). Dense collagenous tissue was observed to be formed in the +GF groups. OC was shown to be expressed in the bone and interface regions of the +GF groups.

After 4 weeks culture with hMSCs, the scaffolds with alternative delivery of CTGF and TGFβ3 successfully guided formation of integrated COL-I+ and COL-II+ matrices within 100 μm interfaces (see e.g., FIG. 3C). Consistently, the rotator cuff scaffolds with integrated three layers enhanced multiphase tissue formation from MSCs by 6 weeks as compared to scaffold without GF delivery (see e.g., FIG. 28A), demonstrated by H&E and Picrosirius Red (PR) staining. Alizarin red staining demonstrated a localized mineralization in the BMP2 μS-delivered region of the ligament-to-bone scaffolds (see e.g., FIG. 28B), suggesting potential of this approach to guide spatial formation of multi-tissues in an integrated scaffold from a single population of stem/progenitor cells.

Discussion.

The novel spatiotemporal delivery system not only enables fabrication of 3D scaffolds with multiple GFs delivered at desired locations but also custom-designed internal microstructure and outer shape/dimension. These in vitro results show that spatially embedded GFs encapsulated PLGA μS from the scaffolds induced tissue specific differentiation of hMSCs at different regions of the scaffold, which was confirmed by histological and immunohistochemical analyses.

This study has shown the potential of the micro-precise spatiotemporal delivery system embedded in 3D printed scaffolds to regenerate multi-tissue complex such as tendon-bone insertion, synovial joints, fibrocartilaginous tissues, and periodontium.

Summary.

It was shown that temporally controlled release of the specific GFs from the spatially embedded μS in the micro-strands guided tissue specific differentiation of the stem/progenitor cells, consequently leading to the regeneration or formation of functional multi-tissue complex with integrated interface. As such, the micro-precise spatiotemporal delivery of GFs embedded in 3D printed scaffolds provides a novel approach for use in multi-tissue complex formation, leading to functional regeneration or formation of damaged or injured connective tissue interfaces.

REFERENCES

Ahtiainen K, Mauno J, Ella V, Hagstrom J, Lindqvist C, Miettinen S, et al. Autologous adipose stem cells and polylactide discs in the replacement of the rabbit temporomandibular joint disc. Journal of the Royal Society, Interface/the Royal Society. 2013; 10:20130287.

Akkineni A R, Luo Y, Schumacher M, Nies B, Lode A, Gelinsky M. 3D plotting of growth factor loaded calcium phosphate cement scaffolds. Acta biomaterialia. 2015; 27:264-74.

Allen K D, Athanasiou K A 2006a. Tissue Engineering of the TMJ disc: a review. Tissue engineering 12(5):1183-1196.

Allen K D, Athanasiou K A 2006b. Viscoelastic characterization of the porcine temporomandibular joint disc under unconfined compression. Journal of biomechanics 39(2): 312-322.

Bose S, Vahabzadeh S, Bandyopadhyay A. Bone tissue engineering using 3D printing. Materials Today. 2013; 16:496-502.

Brown B N, Chung W L, Almarza A J, Pavlick M D, Reppas S N, Ochs M W, Russell A J, Badylak S F 2012. Inductive, scaffold-based, regenerative medicine approach to reconstruction of the temporomandibular joint disk. Journal of oral and maxillofacial surgery: official journal of the American Association of Oral and Maxillofacial Surgeons 70(11):2656-2668.

Castro N J, O'Brien J, Zhang L G. Integrating biologically inspired nanomaterials and table top stereolithography for 3D printed biomimetic osteochondral scaffolds. Nanoscale. 2015; 7:14010-22.

Detamore M S, Hegde J N, Wagle R R, Almarza A J, Montufar-Solis D, Duke P J, Athanasiou K A 2006. Cell type and distribution in the porcine temporomandibular joint disc. Journal of oral and maxillofacial surgery: official journal of the American Association of Oral and Maxillofacial Surgeons 64(2):243-248.

Dimitroulis G. A critical review of interpositional grafts following temporomandibular joint discectomy with an overview of the dermis-fat graft. International journal of oral and maxillofacial surgery. 2011; 40:561-8.

Embree M C, Iwaoka G M, Kong D, Martin B N, Patel R K, Lee A H, et al. Soft tissue ossification and condylar cartilage degeneration following TMJ disc perforation in a rabbit pilot study. Osteoarthritis and cartilage/OARS, Osteoarthritis Research Society. 2015.

Estabrooks L N, Fairbanks C E, Collett R J, Miller L. A retrospective evaluation of 301 TMJ Proplast-Teflon implants. Oral surgery, oral medicine, and oral pathology. 1990; 70:381-6.

Hagandora C K, Almarza A J 2012. TMJ disc removal: comparison between pre-clinical studies and clinical findings. Journal of dental research 91(8):745-752.

Hagandora C K, Gao J, Wang Y, Almarza A J 2013. Poly (glycerol sebacate): a novel scaffold material for temporomandibular joint disc engineering. Tissue engineering Part A 19(5-6):729-737.

Henry C H, Wolford L M. Treatment outcomes for temporomandibular joint reconstruction after Proplast-Teflon implant failure. Journal of oral and maxillofacial surgery: official journal of the American Association of Oral and Maxillofacial Surgeons. 1993; 51:352-8; discussion 9-60.

Jeong C G, Atala A. 3D Printing and Biofabrication for Load Bearing Tissue Engineering. Advances in experimental medicine and biology. 2015; 881:3-14.

Kalpakci K N, Willard V P, Wong M E, Athanasiou K A. An interspecies comparison of the temporomandibular joint disc. Journal of dental research. 2011; 90:193-8.

Kamath M S, et al., Polycaprolactone scaffold engineered for sustained release of resveratrol: therapeutic enhancement in bone tissue engineering Scaffolds with microspheres, Int. J. Nanomed. 9:183-195, 2014.

Lam C X, Savalani M M, Teoh S H, Hutmacher D W. Dynamics of in vitro polymer degradation of polycaprolactone-based scaffolds: accelerated versus simulated physiological conditions. Biomedical materials. 2008; 3:034108.

Lai W F, Tsai Y H, Su S J, Su C Y, Stockstill J W, Burch J G 2005. Histological analysis of regeneration of temporomandibular joint discs in rabbits by using a reconstituted collagen template. International journal of oral and maxillofacial surgery 34(3):311-320.

Lee C H, Marion N W, Hollister S, Mao J J. Tissue formation and vascularization in anatomically shaped human joint condyle ectopically in vivo. Tissue engineering Part A. 2009; 15:3923-30.

Lee C H, Cook J L, Mendelson A, Moioli E K, Yao H, Mao J J 2010a. Regeneration of the articular surface of the rabbit synovial joint by cell homing: a proof of concept study. Lancet 376(9739):440-448.

Lee C H, Shah B, Moioli E K, Mao J J 2010b. CTGF directs fibroblast differentiation from human mesenchymal stem/stromal cells and defines connective tissue healing in a rodent injury model. The Journal of clinical investigation 120(9):3340-3349.

Lee C H, Hajibandeh J, Suzuki T, Fan A, Shang P, Mao J J. Three-dimensional printed multiphase scaffolds for regeneration of periodontium complex. Tissue engineering Part A. 2014a; 20:1342-51.

Lee C H, Rodeo S A, Fortier L A, Lu C, Erisken C, Mao J J 2014b. Protein-releasing polymeric scaffolds induce fibrochondrocytic differentiation of endogenous cells for knee meniscus regeneration in sheep. Science translational medicine 6(266):266ra171.

Li X, et al., Nanofiber scaffolds with gradations in mineral content for mimicking the tendon-to-bone insertion site. Nano Lett. 9(7):2763-2768, 2009.

Lumpkins S B, McFetridge P S 2009. Regional variations in the viscoelastic compressive properties of the temporomandibular joint disc and implications toward tissue engineering. Journal of biomedical materials research Part A 90(3):784-791.

MacBarb R F, Chen A L, Hu J C, Athanasiou K A. Engineering functional anisotropy in fibrocartilage neotissues. Biomaterials. 2013; 34:9980-9.

Moioli E K, Hong L, Guardado J, Clark P A, Mao J J. Sustained release of TGFbeta3 from PLGA microspheres and its effect on early osteogenic differentiation of human mesenchymal stem cells. Tissue engineering. 2006; 12:537-46.

National Health Interview Survey 2012. http://orthoinfo.aaos.org/topic.cfm?topic=a00327.

Pan Z, Ding J 2012. Poly(lactide-co-glycolide) porous scaffolds for tissue engineering and regenerative medicine. Interface focus 2(3):366-377.

Poldervaart M T, Wang H, van der Stok J, Weinans H, Leeuwenburgh S C, Oner F C, et al. Sustained release of BMP-2 in bioprinted alginate for osteogenicity in mice and rats. PloS one. 2013; 8:e72610.

Qian F, Szymanski A, Gao J. Fabrication and characterization of controlled release poly(D,L-lactide-co-glycolide) millirods. Journal of biomedical materials research. 2001; 55:512-22.

Richardson T R, et al., Polymeric system for dual growth factor delivery, Nat Biotech. 19:1029-1034, 2001.

Scapino R P, Canham P B, Finlay H M, Mills D K 1996. The behaviour of collagen fibres in stress relaxation and stress distribution in the jaw-joint disc of rabbits. Archives of oral biology 41(11):1039-1052.

Shim J H, Kim S E, Park J Y, Kundu J, Kim S W, Kang S S, et al. Three-dimensional printing of rhBMP-2-loaded scaffolds with long-term delivery for enhanced bone regeneration in a rabbit diaphyseal defect. Tissue engineering Part A. 2014a; 20:1980-92.

Shim J H, Yoon M C, Jeong C M, Jang J, Jeong S I, Cho D W, et al. Efficacy of rhBMP-2 loaded PCL/PLGA/beta-TCP guided bone regeneration membrane fabricated by 3D printing technology for reconstruction of calvaria defects in rabbit. Biomedical materials. 2014b; 9:065006.

Shin Yokoya et al., Rotator Cuff Regeneration Using a Bioabsorbable Material With Bone Marrow-Derived Mesenchymal Stem Cells in a Rabbit Model, (http://ajs.sagepub.com/content/40/6/1259).

Singh M, et al., Microsphere-based scaffolds for cartilage tissue engineering: using subcritical $CO(2)$ as a sintering agent. Acta Biomater. 6:137-143, 2010.

Stankovic S, Vlajkovic S, Boskovic M, Radenkovic G, Antic V, Jevremovic D 2013. Morphological and biomechanical features of the temporomandibular joint disc: an overview of recent findings. Archives of oral biology 58(10):1475-1482.

Tanaka E, van Eijden T. Biomechanical behavior of the temporomandibular joint disc. Critical reviews in oral biology and medicine: an official publication of the American Association of Oral Biologists. 2003; 14:138-50.

Tarafder S, Brito J A, Jun Y, Lee C H Spatiotemporal Delivery of Multiple Growth Factors in 3D Printed Scaffolds for Engineering Integrated Soft Tissue-To-Bone Interfaces From Stem/Progenitor Cells. Orthopaedic Research Society 2016, Orlando, Fla.

The Burden of Musculoskeletal Diseases in the United States.

Willard V P, Kalpakci K N, Reimer A J, Athanasiou K A. The regional contribution of glycosaminoglycans to temporomandibular joint disc compressive properties. Journal of biomechanical engineering. 2012; 134:011011.

Yamanaka & Matsumoto. Clin Orthop 1994; 304:68-73.

Yilgor P, Hasirci N, Hasirci V. Sequential BMP-2/BMP-7 delivery from polyester nanocapsules. Journal of biomedical materials research Part A. 2010; 93: 528-36.

What is claimed is:

1. A method of forming a polymeric microfiber, the method comprising: (i) encapsulating at least one agent in a plurality of microspheres; (ii) combining the plurality of microspheres and a matrix material, the matrix material being suitable for forming a scaffold via 3D printing; (iii) heating the microspheres and matrix material sufficiently to allow dispensing of the microspheres and matrix material while preventing substantial degradation of the microsphere or the agent encapsulated in the microsphere; and (iv) dispensing the heated microspheres and matrix material to form the polymeric microfiber, wherein the microspheres are combined with the polymeric microfiber, wherein the matrix material is introduced into a first cartridge of a 3D printing device, and the matrix material is dispensed from the cartridge through a printing needle to form the polymeric microfiber, wherein the microspheres are introduced into a second cartridge of a 3D printing device, and the microspheres are dispensed from the cartridge, wherein the microspheres are inserted into or onto the matrix material when forming the polymeric microfiber.

2. The method of claim 1, wherein the matrix material and microencapsulated active agent is heated such that 80% of the total volume of microspheres do not reach more than 45° C. for more than about 30 minutes.

3. The method of claim 2, wherein the scaffold is formed from a plurality of microfibers.

* * * * *